(12) United States Patent
Wagner et al.

(10) Patent No.: US 11,999,960 B2
(45) Date of Patent: Jun. 4, 2024

(54) METHOD OF PRODUCING TOBACCO PLANTS WITH INCREASED SUCROSE ESTER CONTENT

(71) Applicant: University of Kentucky Research Foundation, Lexington, KY (US)

(72) Inventors: George Wagner, Lexington, KY (US); Antoaneta Borissova Mahaylova-Kroumova, Lexington, KY (US); Guiliang Tang, Houghton, MI (US); Erming Wang, Newtonville, MA (US)

(73) Assignee: University of Kentucky Research Foundation, Lexington, KY (US)

( * ) Notice: Subject to any disclaimer, the term of this patent is extended or adjusted under 35 U.S.C. 154(b) by 736 days.

(21) Appl. No.: 16/484,042

(22) PCT Filed: Feb. 6, 2018

(86) PCT No.: PCT/US2018/016963
§ 371 (c)(1),
(2) Date: Aug. 6, 2019

(87) PCT Pub. No.: WO2018/148169
PCT Pub. Date: Aug. 16, 2018

(65) Prior Publication Data
US 2019/0352657 A1 Nov. 21, 2019

Related U.S. Application Data

(60) Provisional application No. 62/455,850, filed on Feb. 7, 2017.

(51) Int. Cl.
| | |
|---|---|
| C12N 15/82 | (2006.01) |
| A24B 3/12 | (2006.01) |
| A24B 13/00 | (2006.01) |
| A24B 15/18 | (2006.01) |
| A24B 15/20 | (2006.01) |

(52) U.S. Cl.
CPC ............ *C12N 15/8218* (2013.01); *A24B 3/12* (2013.01); *A24B 13/00* (2013.01); *A24B 15/183* (2013.01); *A24B 15/20* (2013.01); *C12N 15/8245* (2013.01)

(58) Field of Classification Search
CPC ........ C12N 15/8218; A24B 3/12; A24B 13/00
See application file for complete search history.

(56) References Cited

U.S. PATENT DOCUMENTS

| | | | |
|---|---|---|---|
| 2,162,738 | A | 6/1939 | McCoy |
| 6,002,071 | A | 12/1999 | Chappell et al. |
| 6,342,380 | B1 | 1/2002 | Colby et al. |
| 8,129,514 | B2 | 3/2012 | Ronen et al. |
| 9,115,366 | B2 | 8/2015 | Tissier et al. |

| | | | |
|---|---|---|---|
| 2008/0281135 | A1 | 11/2008 | Tissier et al. |
| 2010/0297722 | A1 | 11/2010 | Anterola et al. |
| 2016/0100546 | A1* | 4/2016 | Nielsen ................ A24B 15/10 800/260 |

FOREIGN PATENT DOCUMENTS

| | | |
|---|---|---|
| AU | 2004244732 B2 | 12/2004 |
| EP | 0120516 A2 | 10/1984 |
| EP | 0242246 A1 | 10/1987 |
| EP | 0449375 A2 | 10/1991 |
| EP | 1828380 B1 | 5/2010 |
| EP | 2565265 A1 | 3/2013 |
| GB | 2197653 A | 5/1988 |
| GB | 2515502 A | 12/2014 |
| JP | 2015165798 A | 9/2015 |
| KR | 20120051429 A | 5/2012 |
| RU | 2479582 C1 | 4/2013 |
| WO | 9720056 A2 | 6/1997 |
| WO | 0208269 A2 | 1/2002 |
| WO | 2005111217 A2 | 11/2005 |
| WO | 2006040479 A3 | 4/2006 |
| WO | 2006091194 A1 | 8/2006 |
| WO | 2006138005 A2 | 12/2006 |
| WO | 2008007031 A1 | 1/2008 |
| WO | 2008034648 A1 | 3/2008 |
| WO | 2009064771 A2 | 5/2009 |
| WO | 2010097623 A1 | 9/2010 |
| WO | 2011154385 A1 | 12/2011 |

(Continued)

OTHER PUBLICATIONS

Ennajdaoui, Hanane, et al. "Trichome specific expression of the tobacco (*Nicotiana sylvestris*) cembratrien-ol synthase genes is controlled by both activating and repressing cis-regions." Plant molecular biology 73.6 (2010): 673-685. (Year: 2010).*
GenBank: AF401234.1, extracted from www.ncbi.nlm.nih.gov/nuccore/AF401234.1 (Year: 2001).*
GenBank: HM241151.1, extracted from www.ncbi.nlm.nih.gov/nuccore/HM241151.1 (Year: 2010).*
Xiao, Yue-Hua, et al. "Direct amplification of intron-containing hairpin RNA construct from genomic DNA." Biotechniques 41.5 (2006): 548-552. (Year: 2006).*

(Continued)

*Primary Examiner* — Weihua Fan
(74) *Attorney, Agent, or Firm* — McKee, Voorhees & Sease, PLC

(57) ABSTRACT

The present invention provides a method for increasing the sucrose ester content of a tobacco plant or tobacco cell culture, the method comprising modifying said tobacco plant or tobacco cell culture by inhibiting the activity or expression of a diterpene synthesis gene. The present invention also provides for the use of a diterpene synthesis gene for increasing the sucrose ester content of a tobacco plant or tobacco cell culture, as well as tobacco cells, tobacco plants, tobacco plant propagation materials, harvested leaves, processed tobaccos, or tobacco products obtainable in accordance with the invention.

18 Claims, 17 Drawing Sheets

Specification includes a Sequence Listing.

(56) References Cited

FOREIGN PATENT DOCUMENTS

| WO | 2012058636 A1 | 5/2012 |
|---|---|---|
| WO | 2012085806 A1 | 6/2012 |
| WO | 2013029799 A1 | 3/2013 |
| WO | 2013034459 A1 | 3/2013 |
| WO | 2015169925 A1 | 11/2015 |

OTHER PUBLICATIONS

Wang, Erming, and George J. Wagner. "Elucidation of the functions of genes central to diterpene metabolism in tobacco trichomes using posttranscriptional gene silencing." Planta 216.4 (2003): 686-691. (Year: 2003).*
Chang, Aixia, et al. "Characterization of trichome-specific BAHD acyltransferases involved in acylsugar biosynthesis in Nicotiana tabacum." Journal of Experimental Botany (2022). (Year: 2022).*
Wagner, George J., and Antoaneta B. Kroumova. "The use of RNAi to elucidate and manipulate secondary metabolite synthesis in plants." Current perspectives in microRNAs (miRNA) (2008): 431-459. (Year: 2008).*
Ennajdaoui et al., "Trichome specific expression of the tobacco (*Nicotianna sylvestris*) cembratrien-ol genes is controlled by both activating and repressing cis-regions", Plant Mol Biol, vol. 73, pp. 673-685, May 1, 2010.
Kandra et al., "Modified branched-chain amino acid pathways give rise to acyl acids of sucrose esters exuded from tobacco leaf trichomes", Eur. J. Biochem., vol. 188, pp. 385-391 1990.
Tissier et al., "Tobacco Trichomes as a Platform for Terpenoid Biosynthesis Engineering", Isoprenoid Synthesis in Plants and Microorganisms: New Concepts and Experiments Approaches, Chapter 18, pp. 271-283, 2012.
Wang et al., "Elucidation of the functions of genes central to diterpene metabolism in tobacco trichomes using post-transcriptional gene silencing", Planta, vol. 216, pp. 686-691, 2003.
University of Kentucky Research Foundation, Application No. PCT/US2018/016963, filed Feb. 6, 2018, "The International Search Report and The Written Opinion of the International Searching Authority, or the Declaration" dated May 16, 2018, 15 pages.
Wagner et al., "The Use of RNAi to Elucidate and Manipulate Secondary Metabolite Synthesis in Plants", Current Perspectives in microRNAs, pp. 431-459, Sep. 2008.
Wagner, George, "Secreting Glandular Trichomes: More than Just Hairs", Plant Physiol., vol. 96, pp. 675-679, 1991.
Wang et al., "Transgenic Nicotiana Tabacum L. with enhanced trichome exudate cembratrieneols has reduced aphid infestation in the field", Molecular Breeding, vol. 13, pp. 49-57, 2004.
Wang et al., "Suppression of a P450 hydroxylase gene in plant trichome glands enhances natural-product-based aphid resistance", Biotech Nature, vol. 19, pp. 371-374, Apr. 2001.
Warner et al., "Isolation of an asparagus intracellular PR gene (AoPR1) wound-responsive promoter by the inverse polymerase chain reaction and its characterization in transgenic tobacco", The Plant Journal, 3(2), pp. 191-201, 1993.
Zhang et al., "Analysis of Rice Act1 5' region Activity in Transgenic Rice Plants", The Plant Cell, vol. 3, pp. 1155-1165, Nov. 1991.
Wang et al., NCBI GenBank AAK95517, 2 pages, Jul. 20, 2001.
Wang et al., NCBI GenBank AAS46038, 2 pages, Dec. 4, 2003.
Wang et al., NCBI GenBank AF401234, 2 pages, Jul. 20, 2001.
Chen et al., NCBI GenBank AF502128, 2 pages, Apr. 12, 2002.
Wang et al., NCBI GenBank AY049090, 2 pages, Jul. 31, 2001.
Wang et al., NCBI GenBank AY495694, 2 pages, Dec. 4, 2003.
Wang et al., NCBI GenBank AY528645, 2 pages, Jan. 16, 2004.
Ennajdaoui et al., NCBI GenBank NP_001289493, 2 pages, 2010.
Ennajdaoui et al., NCBI GenBank NP_001289541, 2 pages, 2010.
Ennajdaoui et al., NCBI GenBank NP_001289542, 2 pages, 2010.
Unknown, NCBI GenBank XP_006365530, 2 pages, Jan. 5, 2016.
Unknown, NCBI GenBank XP_006365934, 2 pages, Jan. 5, 2016.
Unknown, NCBI GenBank XP_006367561, 2 pages, Jan. 5, 2016.
Unknown, NCBI GenBank XP_006367836, 2 pages, Jan. 5, 2016.
Unknown, NCBI GenBank XP_009594549, 2 pages, Oct. 19, 2016.
Unknown, NCBI GenBank XP_009609204, 2 pages, Oct. 19, 2016.
Unknown, NCBI GenBank XP_009782439, 2 pages, Oct. 21, 2014.
Unknown, NCBI GenBank XP_009793508, 2 pages, Oct. 21, 2014.
Unknown, NCBI GenBank XP_009803139, 2 pages, Oct. 21, 2014.
Unknown, NCBI GenBank XP_015077699, 2 pages, Jan. 28, 2019.
Unknown, NCBI GenBank XP_015077799, 2 pages, Jan. 28, 2019.
Unknown, NCBI GenBank XP_015078050, 2 pages, Jan. 28, 2019.
Unknown, NCBI GenBank XP_015078923, 2 pages, Jan. 28, 2019.
Unknown, NCBI GenBank XP_015161133, 2 pages, Jan. 5, 2016.
European Patent Office in connection with EP0249637, 5 pages, completed on Mar. 10, 1988.
Altschul et al., "Basic Local Alignment Search Tool", J. Mol. Biol., vol. 215, pp. 403-410, 1990.
An et al., "Binary vectors", Plant Molecular Biology Manual, A3, pp. 1-19, 1988.
An et al., "New Cloning vehicles for transformation of higher plants", The EMBO Journal, vol. 4, No. 2, pp. 277-284, 1985.
An et al., "Transformation of Tobacco, Tomato, Potato, and *Arabidopsis thaliana* Using a Binary Ti Vector System", Plant Physiol., vol. 81, pp. 301-305, 1986.
Arrendale et al., "Characterization of the Sucrose Ester Fraction from Nicotiana glutinosa", J. Agric. Food, vol. 38, pp. 75-85, 1990.
Ashraf-Khorassani et al., "Isolation, Fractionation, and Identification of Sucrose Esters from Various Oriental Tobaccos Employing Supercritical Fluids", Beitrage zur Tabakforschung International/Contributions to Tobacco Research, vol. 23, No. 1, 14 pages, Apr. 2008.
Ausubel et al., Short Protocols in Molecular Biology, Fourth Edition, Bioinformatics, Chapter18, pp. 1-25, 1999.
Ausubel et al., Short Protocols in Molecular Biology, Fourth Edition, Homology Searching, Chapter 7, pp. 56-60, 1999.
Beaucage et al., "Deoxynucleoside Phosphoramidites—a new class of key intermediates for deoxypolynucleotide synthesis", Tetrahedron Letters, vol. 22, No. 20, pp. 1859-1862, 1981.
Benfey et al., "Regulated Genes in Transgenic Plants", Science, vol. 244, pp. 174-181, Apr. 14, 1989.
Bevan, M.: "Binary Agrobacterium vectors for plant transformation", Nucleic Acids Research, vol. 12, No. 22, pp. 8711-8721. 1984.
Butcher et al., "The role of tissue culture in the study of crown-gall tumorigenesis", Tissue Culture Methods for Plant Pathologists, pp. 203-208, 1980.
Caruthers et al, "New chemical methods for synthesizing polynucleotides", Nucleic Acids Research, Symposium Series 7, pp. 215-223, 1980.
Christou, Paul, "Genetic engineering of crop legumes and cereals: current status and recent advances", Agro-Food Industry Hi-Tech, pp. 17-27, Mar. 1994.
Clough et al., "Floral dip: a simplified method for Agrobacterium-mediated transformation of *Arabidopsis thaliana*", The Plant Journal, vol. 16, No. 6, pp. 735-743, 1998.
Cornejo et al., "Activity of a maize ubiquitin promoter in transgenic rice", Plant Molecular Biology, vol. 23, pp. 567-581, 1993.
Falara et al., "The Tomato Terpene Synthase Gene Family", Plant Physiology, vol. 157, pp. 770-789, Oct. 2011.
Foulds et al., "Effect of smokeless tobacco (snus) on smoking and public health in Sweden", Tobacco Control., vol. 12, pp. 349-359, 2003.
Fraley et al., "Genetic Transformation in Higher Plants", Critical Review Plant Science, vol. 4, Issue 1, pp. 1-46, 1986.
Frame et al., "Production of fertile transgenic maize plants by silicon carbide whisker-mediated transformation", The Plant Journal, vol. 6, pp. 941-948, 1994.
Gan et al., "Making sense of senescence, Molecular Genetic Regulation and Manipulation of Leaf Senescence", Plant Physiol., vol. 113, pp. 313-319, 1997.
Gatz, Christiane, "Novel Inducible/Repressible Gene Expression Systems", Methods in Cell Biology, vol. 50, pp. 411-424, 1995.
Gepstein et al., "Large-scale identification of leaf senescence-associated genes", The Plant Journal, vol. 36, pp. 629-642, 2003.
Hale & Marham, "The Harper Collins Dictionary of Biology", Harper Perennial, 576 pages, Mar. 1, 1991.

(56) References Cited

OTHER PUBLICATIONS

Higgins et al., "CLUSTAL: a package for performing multiple sequence alignment on a microcomputer", Gene, vol. 73, pp. 237-244, 1988.
Hoekema et al., "Non-Oncogenic T-Region Derived Plant Vectors in the Agrobacterium Binary System", Chapter V, pp. 63-71, 1985.
Horn et al., "Synthesis of oligonucleotides on cellulose. Part II: design and synthetic strategy to the synthesis of 22 oligodeoxynucleotides coding for Gastric Inhibitory Polypeptide (GIP)", Nucleic Acids Research, Symposium Series, No. 7, p. 225-232, 1980.
Horsch, et al., "A Simple and General Method for Transferring Genes into Plants", Science, pp. 1229-1231 1985.
Horwell, David C., "The 'peptoid' approach to the design of non-peptide, small molecule agonists and antagonists of neuropeptides", Trends in Biotechnology, vol. 13, pp. 132-134, Apr. 1995.
Hull et al., "The sequence of carnation etched ring virus DNA: comparison with cauliflower mosaic virus and retroviruses", The EMBO Journal, vol. 5, No. 12, pp. 3083-3090, 1986.
Kandra et al., "Studies of the Site and Mode of Biosynthesis of Tobacco Trichome Exudate Components", Archives of Biochemistry and Biophysics, vol. 265, No. 2, pp. 425-432, Sep. 1988.
Karrer et al., "Analysis of Sucrose Fatty Acid Esters by High Temperature Gas Chromatography", Journal of High Resolution Chromatography, vol. 15, No. 9, pp. 585-589, 1992.
Kay et al., "Duplication of CaMV 35S Promoter Sequences Creates a Strong Enhancer for Plant Genes", Science, vol. 236, No. 4806, pp. 1299-1302, Jun. 5, 1987.
Mahmoud et al. "Metabolic engineering of essential oil yield and composition in mint by altering expression of deoxyxylulose phosphate reductoisomerase and menthofuran synthase", PNAS, vol. 98, No. 15, pp. 8915-8920, Jul. 17, 2001.
Matthes et al., "Simultaneous rapid chemical synthesis of over one hundred oligonucleotides on a microscale", EMBO Journal, vol. 3, No. 4, pp. 801-805, 1984.
Meyer et al., "The use of African cassava mosaic virus as a vector system for plants", Gene, vol. 110, pp. 213-217, 1992.
Odell et al., "Identification of DNA sequences required for activity of the cauliflower mosaic virus 35S promoter", Nature Publishing Group, vol. 313, pp. 810-812, Feb. 28, 1985.
Potrykus et al., "Gene transfer to plants: Assessment of Published Approaches and Results", Annual Review Plant Physiology & Plant Molecular Biology, vol. 42, pp. 205-225, 1991.
Sallaud et al., "Characterization of two genes for the biosynthesis of the labdane diterpene Z-abienol in tobacco (*Nicotiana tabacum*) glandular trichomes", The Plant Journal, vol. 72, pp. 1-17, May 23, 2012.
Sambrook et al., "Molecular Cloning, A Laboratory Manual", Cold Spring Harbor Laboratory Press, Second Edition, 30 pages, 1989.
Severson et al., "Isolation and Characterization of the Sucrose Esters of the Cuticular Waxes of Green Tobacco Leaf", J. Agric. Food Chem., vol. 33(5), pp. 870-875, 1985.
Silva et al., "Meganucleases and Other Tools for Targeted Genome Engineering: Perspectives and Challenges for Gene Therapy", Current Gene Therapy, vol. 11, pp. 11-27, 2011.
Simon et al., "Peptoids: A modular approach to drug discovery", Proc. Natl. Acad. Sci. USA, vol. 89, pp. 9367-9371, Oct. 1992.
Singleton et al., Dictionary of Microbiology and Molecular Biology, Wiley-Blackwell, 895 pages, Dec. 16, 1987.
Slocombe et al., "Transcriptomic and Reverse Genetic Analyses of Branched-Chain Fatty Acid and Acyl Sugar Production in Solanum pennellii and Nicotiana benthamiana", Plant Physiology, vol. 148, pp. 1830-1846, Dec. 2008.
Tatusova et al., "BLAST 2 Sequences, a new tool for comparing protein and nucleotide sequences", FEMS Microbiology Letters, vol. 174, pp. 247-250, 1999.
Tatusova et al., Erratum to "BLAST 2 Sequences, a new tool for comparing protein and nucleotide sequences", FEMS Microbiology Letters, vol. 177, pp. 187-188, 1999.
Van Der Hoeven et al., "Genetic control and Evolution of Sesquiterpene Biosynthesis in Lycopersicon esculentum and L hirsutum", The Plant Cell, vol. 12, pp. 2283-2294, Nov. 2000.
Wagner et al., "New Approaches for Studying and Exploiting an Old Protuberance, the Plant Trichome", Annals of Botany, vol. 93, pp. 3-11, 2004.
Wagner et al., "Transfer of Gene Knockdown Constructs into Elite Tobacco Lines to Alter Tobacco Organoleptic Properties", Kentucky Tobacco Research & Development Center, Annual Report, Organoleptic Properties, pp. 303-305, Jul. 1, 2012.
Cane, "Nature as organic chemist", The Journal of Antibiotics, 2016, vol. 69, pp. 473-485.
Bohlmann et al., "Plant terpenoid synthases: Molecular biology and phylogenetic analysis," Proceedings of the National Academy of Sciences of the United States of America, Apr. 1998, vol. 95, pp. 4126-4133.

* cited by examiner

Sucrose Ester

Figure 6.

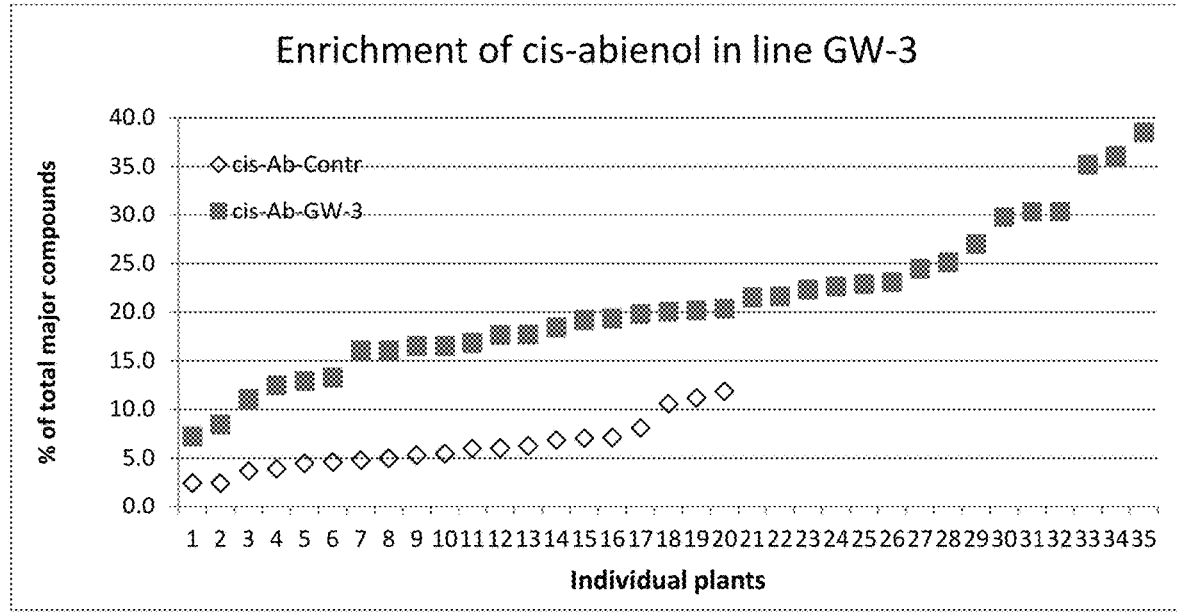

Figure 7A SEQ ID NO:1

```
   1 ccttatattt atccaccact tgagctactt tctataacca attaaagtaa gtccaattct
  61 aacattgtat gctgtgctgc ccttattttt ggctacaaaa ctcgaaagca aaggaactag
 121 aaaactcgtc tggcgagaga aagagagatg agtcaatcaa tttctccaat ctttcctcgc
 181 tttgcaaaat ttcagtcgaa tatttggagg tgcagtactt ttgaactcag agttatacac
 241 tcatcatatg cctctattgg agggaggaga aaagagagag aaagaagaat gaagcgagca
 301 atgaatcctt cttcaagctc gcgtcatttg gcagattttc actcaaccat ttggggtgac
 361 catttctct cctacaattc tgaaataaca gtaggtcaca tacatatgta atcacatgct
 421 tatattctat ttgaatttgt tatctaaatg tttaaaggaa taaagatgtt ataattttat
 481 tagagacagg atcaagcatt taaacttgga aggtttaacc tttaagattg gtctttatcg
 541 tacttttgaa attatgagtt tgaaatttaa tactccatcc gtctcaataa agaatgaata
 601 ttttactatc tagggagtca aacaagattt tctcaaccct ttttttcgca aatgcatttt
 661 aaaaattttg aaattttttaa ttgttgtgac ttacaactac cttcttatgt acttcctaaa
 721 tgtgtaaatc tcattttcaa aaaatttacg gaatatatat tcgtcacatt gaaaatattt
 781 aatttgaccc tcatactccg aaaaggttca aataaattga aacgaatgga atagtactat
 841 tttgtaaaaa cttatgtaga ttttcactat atatctaata agtattcaaa actaataaat
 901 aatgatcaac atatgcggat ctaagattta aattttttgg gttcacctt aaggatctgt
 961 tacaatttta gtagaatgtt accataaatt tgtgctccgt gaaatgtatt gagtcagatg
1021 aacctggtat tatacatgcg gatacgctcc tgatgctcaa tttctgcctg caggaaatta
```

Figure 7B

```
1081 ctacccaaga gaaaaatgaa catgaaatgc taaaagaaat agttcggaaa atgttggtag
1141 aaactccaga taatagtaca caaaaactag tcttgattga cacaattcaa agattgggat
1201 tagcatatca tttcaatgat gagattgaaa actccattca aaacatcttt aatttgtctc
1261 aaaatagtga aaatgacaat gaacacaacc tttatgttgc tgctcttcgt tttcgacttg
1321 cgaggcaaca aggatattac atgtcttcag gtaccttaca tttctgccct ttcccgcaca
1381 gcttcatttt ttttcgttgt taaaggcagc tcggcgtata aaatatctcg tgtatacgca
1441 gggtcaggac ggaaccgccc ccaaggggtg taaagtatgc aacctaccct aatactaaat
1501 atctcgtgtt atacacaggg tcaggacaag tcgcacccaa gaggtgtaat gtaggcaact
1561 tacccctaatg ctagcattag taactgattt tatggctcaa acacataaat tgtaggtcac
1621 acagtaacaa ctttatcgtt ctcaaagact cgccttcctc ttttttttagt tatcgcacct
1681 tatttgttgc aaagaatagc aagtttcgag atctgcttct atataaaaaa cttctgtatt
1741 atactttttt attttgtcct tctgcttaaa aatagtaaaa aactataatg tggaaattgt
1801 aaatttctta actagctgtg aaatcaaata gttattatag gaatataatt tagactccac
1861 ttatggaaaa ccactgggtt gccgttgtta ttgtcaataa taacttgggg tacgatttac
1921 ttcttttttcc atggctgtcc acgactatat ttctattaac caatgttgtg actatgcttt
1981 cccttgagtc gaggatctat tgataacagg ctcttcgatc tttaacaagg taaaagtaat
2041 gtctgcgtac acactctact ccgcagaccc acttgtagga tttcattgaa tttttttttt
2101 tgttgttgtt gttgtaataa cttagggttt agtttcttga tgctgatgaa attcagttct
2161 ttcaactata aacatggtgt tcaccagatg tgttcaagca attcactaac catgacggaa
2221 aattcaagga aaatcatatt aatgatattc aaggattact aagtttgtat gaagcaacac
2281 atatgagagt gcacgacgag gaaattctag aagaagctct tatctttacc accactcatc
2341 tcgagtccat gatcccaaat ttgagcaact cgcttaaggt acaagttact gaagcctcaa
2401 accaacctat tcgcaaaact ataccgaggg tgggatcaag gaaatacata tacatatatg
2461 aaaacattgg aacacataat gatttgcttg tgaaatttgc aaagttggac tttaacatgt
2521 tacaagagct tcatcgaaaa gagctcaacg agctaacaag gtacatctac tattcttatc
2581 attttcatag ttatggtaca gtcagatctc tctataaaat ccatccttta taacaacggt
2641 tcaccataac ggtcatgttt tctttagaac taatctttta tgttaccaaa aaatttcgaa
2701 acaattgaga ctattataga gatgtttgat ggtaactcgc gctaattaat aacacctaaa
2761 gtttaagtat gttaatgttg ttgtgttatc tatagctggt ggaaagaaat ggattttgca
2821 acaaatttcc aatatgcaaa gggcagattg gtagaagctt acttttggat ggtgggaata
2881 tattttgaac ctcaatatag tcgttcaaga agaatgataa cacaagtagt caacatgaac
2941 tccatcattg atgacactta tgatgctttt gcaacttttg atgagcttat gcttttcacg
3001 gatgcgatcc aaaggtaatc tttctataac aactgcattt gttctgataa ttttttaaga
3061 tgctatttga agtgttgtta tagagaaata tattatgaca acttagactt tgcagatggg
3121 atgtaggtgc catggattca ttaccggcat atttgagacc tatttatcaa ggccttctcg
3181 acgttttcaa tgaaatggaa gaagtaatgg ccaaagaagg taagcagat cgcatctact
3241 atgcgaaaaa agaggtaatc cttgattaag ttacattaat tactacttaa taagttaatt
3301 aagtaaacca agttgtaggg aagaatcaca attttgaact attagtactt tttctgttac
3361 ttttttagat gaaaaagttg gtggcagcct attttaagga agttgaatgg ttgaatgcta
```

Figure 7C

```
3421 actacattcc aaaatgtgag gagtatatga aaaatggagt tgtaagttgt accggtagat
3481 gtatggaaca atttgctttg gttgttatcg aggaaattat aacaaaagag gcttttgaat
3541 ggttggcaaa tgaacctttg attcctcgag ctgcatcaac aatctgtaga ttaatggatg
3601 atattgttga tcatgaatta agtataacaa tataatttcc attttatata acaattagtc
3661 atcctaattc acaaattttg tccctaaata catacaaaaa caactacaat aacagaaaca
3721 acatatccag tgtattccta tagtacgggt ctgggcagag agatgtgtat gaagatctta
3781 ccctatcttg tggaggtaga aaggttgttt cccgatagac cctcgactca aaaaaacatt
3841 tctcaatctg atttcgagtc taggtggcac ttttgcatga tataataaat agacatgctt
3901 gataaattac aacttcaatg agcacattta cataaagtga tttatggaac tttagaaacg
3961 aactgattaa aatggtaaaa tattgtataa tattaatgaa gatattgaaa tatattatgt
4021 gtaggttgaa caacaaagag gacatgttgc ttcatttgtt gagtactaca tgaaagaata
4081 tggaacttca aagcaagaag catatgttga gatgtggaaa aagatcacaa atgcgtggaa
4141 agacataaat aaggaactcc tgcgcgctac tgcagtacca atgtttgtcc tcgaacgaac
4201 tttagattat acaagattgg ttgatacatg tttcaaagat gatgatggtt acacaaatcc
4261 caaatccaaa gtgaaagaca tgattgcttt gttgtttgtc gaatctatcg acatatgatg
4321 atatataaca atgcagatgc accttcaacc gagtattcag agcaaatatg gaagcatttt
4381 gtatggttct gtatgaccta taggtcatat gttcgagtca tggaagcatc cattaatact
4441 tgcattaggg taggctgtct atatcatact tattagggtg cgacccttcc cctgactctg
4501 catgaatgca ggatgctttg tgcgctcagc tgcctttttt tactatttcg ctgtcagtta
4561 tgtttgagaa gggacaatac ttgatttgat tcatgcagtc ttgtctccag gtttgattcc
4621 tatg
```

Figure 8. SEQ ID NO: 2

MSQSISPIFPRFAKFQSNIWRCSTFELRVIHSSYASIGGRRKER

ERRMKRAMNPSSSSRHLADFHSTIWGDHFLSYNSEITEITTQEKNEHEMLKEIVRKML

VETPDNSTQKLVLIDTIQRLGLAYHFNDEIENSIQNIFNLSQNSENDNEHNLYVAALR

FRLARQQGYYMSSDVFKQFTNHDGKFKENHINDIQGLLSLYEATHMRVHDEEILEEAL

IFTTTHLESMIPNLSNSLKVQVTEASNQPIRKTIPRVGSRKYIYIYENIGTHNDLLVK

FAKLDFNMLQELHRKELNELTSWWKEMDFATNFQYAKGRLVEAYFWMVGIYFEPQYSR

SRRMITQVVNMNSIIDDTYDAFATFDELMLFTDAIQRWDVGAMDSLPAYLRPIYQGLL

DVFNEMEEVMAKEGKADRIYYAKKEMKKLVAAYFKEVEWLNANYIPKCEEYMKNGVVS

CTGRCMEQFALVVIEEIITKEAFEWLANEPLIPRAASTICRLMDDIVDHEVEQQRGHV

ASFVEYYMKEYGTSKQEAYVEMWKKITNAWKDINKELLRATAVPMFVLERTLDYTRLV

DTCFKDDDGYTNPKSKVKDMIALLFVESIDI

Figure 9. SEQ ID NO: 3

```
   1 tgcagccaca gtactgcttc atcaatggaa gaggcaaagg agagaataag ggaaacattt
  61 ggaaaaatag agctatctcc ttcttcctat gacacagcat gggtagctat ggtcccttca
 121 agatattcta tgaaccaacc atgttttcct cagtgcttag attggattct tgaaaatcaa
 181 agagaagatg gatcttgggg cctaaatcct agccatccat tgcttgtaaa agactccctt
 241 tcttccactc tagcatcttt gcttgcccct cgcaaatgga gaattggaga taaccaagtc
 301 caaagaggcc ttggctttat tgaaacgcat ggttgggcag tcgataacaa ggatcagatt
 361 tcacctttag gatttgaaat tatatttccc tgcatgacca actatgcaga gaaacttaat
 421 ttggatctac ctttggatcc taaccttgta aatatgatgc tctgcgaacg tgaattaaca
 481 attgaaagag ccttaaagaa tgaattcgag gggaatatgg caaatgtaga atattttgct
 541 gaaggactcg gtgaatcatg tcattggaaa gagatgatgc ttcgtcagag acacaacggg
 601 tcgctctttg attccagc cactactgca gctgccttga tttaccatca gtacgatgag
 661 aaatgctttg ggtacttgaa ctcaatcttg aaactgcacg ataattgggt ccacactatt
 721 tgccctacaa agatacattc aaatctcttc ttagttgatg cccttcaaaa tcttggagta
 781 gatcggtatt ttaaaacaga agtcaaaaga gtactagatg aaatatacag gctttggcta
 841 gaaaagaatg aagaaatttt ttcagacgtt gctcattgtg ccatggcgtt tcgacttta
 901 cggatgaata actatgaagt ttcctcagaa gaacttgaag gatttgtcga ccaagaacat
 961 ttctttacaa catcaagtgg gaaacttatg aatcacgttg caattctcga acttcaccga
1021 gcttcacagg tggctattca tgaaaggaaa gatcacattt tagataaaat aagtacttgg
1081 acaaggaatt ttatggagca aaaactcttg gacaagcaca tccctgatag gtcaaagaag
1141 gagatggaat ttgctatgag gaaatttat ggcacatttg atcgagtgga aactagacgt
1201 tacatcgagt catacaaaat ggacagtttt aagatcttaa aagcggctta caggtcttcc
1261 ggtattaaca acatagactt gctaaagttc tcagaacacg attttaactt gtgccaaacc
1321 cgacacaaag aagaacttca acagatgaaa aggtggttca cagattgcaa actcgaacaa
1381 gtaggattat cacaacagta cttatacact agttacttca taattgctgc tatactcttt
1441 gaacctgaat atgctgatgc tcgtctagca tatgcaaagt acgccataat aataacagcg
1501 gtggatgatt tcttcgattg tttatttgc aaagaagaac tgcaaaacat catcgaatta
1561 gtagagagat gggagggata ctcaaccgtc ggattccgtt cagagagggt tagaattttc
1621 ttttttggcac tttacaaaat ggtagaggaa attgcggcaa aggcggaaac taagcaaggt
1681 cgatgtgtca aagatcacct tattaacttg tggattgata tgttgaagtg tatgctagtg
1741 gaattggacc tttggaaaat taaatcaact accccaagca tagaggagta cttgtctgtt
1801 gcatgtgtaa ctattggtgt tccatgtttt gttctcacat cactatatct tcttggacca
1861 aaactgtcca aggatgtcat agaaagttct gaggtcagtg ccttatgcaa ttgtacagct
1921 gctgtggccc gattgattaa tgatatacac agttacaaga gagaacaagc agaaagttca
1981 acaaatatgg tatcaatatt aataacacaa agtcaggaa ctatctctga agaagaggct
2041 ataagacaga taaaggaaat gatggaaagt aagagaagag agttgctagg gatggttcta
2101 caaataaag aaagccaatt gccacaagtg tgcaaggatc ttttttggac gacaatcaac
2161 gcagcagctt attctataca tacacatggg cgatgggtat cgcttcccag aggaattcaa
2221 gaaccatatc aacgatgtaa tttacaaacc actcaatcaa tattccccat aatatgcctt
2281 aaatctttta caatatgtta ctaatctttg gaacttggtt gtgatattat tagatgcatg
2341 gacgaattgt acttctttta tgttgtgcac aataatgtac aactgttact atgggaaaaa
2401 cttacttaca ctgctaaaaa aaaaaaaaaa aaa
```

Figure 10. SEQ ID NO: 4

MEEAKERIRETFGKIELSPSSYDTAWVAMVPSRYSMNQPCFPQC

LDWILENQREDGSWGLNPSHPLLVKDSLSSTLASLLALRKWRIGDNQVQRGLGFIETH

GWAVDNKDQISPLGFEIIFPCMTNYAEKLNLDLPLDPNLVNMMLCERELTIERALKNE

FEGNMANVEYFAEGLGESCHWKEMMLRQRHNGSLFDSPATTAAALIYHQYDEKCFGYL

NSILKLHDNWVHTICPTKIHSNLFLVDALQNLGVDRYFKTEVKRVLDEIYRLWLEKNE

EIFSDVAHCAMAFRLLRMNNYEVSSEELEGFVDQEHFFTTSSGKLMNHVAILELHRAS

QVAIHERKDHILDKISTWTRNFMEQKLLDKHIPDRSKKEMEFAMRKFYGTFDRVETRR

YIESYKMDSFKILKAAYRSSGINNIDLLKFSEHDFNLCQTRHKEELQQMKRWFTDCKL

EQVGLSQQYLYTSYFIIAAILFEPEYADARLAYAKYAIIITAVDDFFDCFICKEELQN

IIELVERWEGYSTVGFRSERVRIFFLALYKMVEEIAAKAETKQGRCVKDHLINLWIDM

LKCMLVELDLWKIKSTTPSIEEYLSVACVTIGVPCFVLTSLYLLGPKLSKDVIESSEV

SALCNCTAAVARLINDIHSYKREQAESSTNMVSILITQSQGTISEEEAIRQIKEMMES

KRRELLGMVLQNKESQLPQVCKDLFWTTINAAAYSIHTHGRWVSLPRGIQEPYQRCNL

QTTQSIFPIICLKSFTICY

Figure 11. SEQ ID NO: 5 ctcgtttggcgagagaaagagagagatgagtcaatcaatttctccattaatgttttctcactttgcaaaatttcagtcgaatatttggagatgcaatactt
ctcaactcagagttatacactcatcatatgcctcttttggagggagaagaaaagagagagtaagaagaatgaatcgagcaatggatcttcttcaagc
tctcgtcatttggcagattttccctcaacaatttggggtgaccattttctctcctacaattctgaaataacagaaattactacccaagagaaaaatgaac
atgaaatgctaaaagaaatagttcggaaaatgttggtagaaactccagataatagtacacaaaaactagtcttgattgacacaattcaaagattggg
attagcatatcatttcaatgatgagattgaaaactccattcaaaacatctttaatttgtctcaaaatagtgaagatgacgatgaacacaacctttatgtt
gctgctcttcgttttcgacttgcgaggcaacaaggatattacatgtcttcagatgtgttcaagcaattcactaaccatgacggaaaattcaaggaaaatc
atactaatgatgttcaaggattattgagtttgtatgaagcagcacatatgagagtgcacgacgagga<u>gatatctacccgcttcgcgtcggcatccggtc</u>
<u>agtggcagtgaagggcgaacagttcctgattaaccacaaaccgttctactttactggctttggtcgtcatgaagatgcggacttgcgtggcaaaggatt</u>
<u>cgataacgtgctgatggtgcacgaccacgcattaatggactggattggggccaactcctaccgtacctcgcattacccttacgctgaagagatgctcga</u>
<u>ctgggcagatgaacatggcatcgtggtgattgatgaaactgctgctgtcggctttaacctctctttaggcattggtttcgaagcgggcaacaagccgaa</u>
<u>agaactgtacagcgaagaggcagtcaacggggaaactcagcaagcgcacttacaggcgattaaagagctgatagcgcgtgacaaaaaccacccaa</u>
<u>gcgtggtgatgtggagtattgccaacgaaccggatacccgtccgcaaggtgcacgggaatatttcgcgccactggcggaggcaacgcgtaaactcga</u>
<u>cccgacgcgtccgatcacctgcgtcaatgtaatgttctgcgacgctcacaccgataccatcagcgatctctttgatgtgctgtcctgaaccgttattacg</u>
<u>gatggtatgtccaaagcggcgatttggaaacggcagagaaggtactggaaaaagaacttctggcctggcaggagaaactgcatcagccgattatcat</u>
<u>caccgaatacggcgtggatacgttagccgggctgcactcaatgtacaccgacatgtggagtgaagagtatcagtgtgcatggctggatatgtatcacc</u>
<u>gcgtctttgatcgcgtcagcgccgtcgtcggtgaacaggtatggaatttcgccgattttgcgacctcgcaaggcatattgcgcgttggcggtaacaaga</u>
<u>aagggatcttcactcgcgaccgcaaaccgaagtcggcggcttttctgctgcaaaaacgctggactggcatgaacttcggtgaaaaaccgcagcaggg</u>
<u>aggcaaacaatgatcctcgtcgtgcactctcatatgtgctgcttcatacaaactcaataatccttgaacatcattagtatgattttccttgaattttccgtc</u>
atggttagtgaattgcttgaacacatctgaagacatgtaatatccttgttgcctcgcaagtcgaaaacgaagagcagcaacataaaggttgtgttcatc
gtcatcttcactattttgagacaaattaaagatgttttgaatggagttttcaatctcatcattgaaatgatatgctaatcccaatctttgaattgtgtcaat
caagactagtttttgtgtactattatctggagtttctaccaacattttccgaactatttctttagcatttcatgttcattttctcttgggtagtaatttctgtt
atttcagaattgtaggagagaaaatggtcaccccaaattgttgagggaaaatctgccaaatgacgagagcttgaagaaagatccattgctcgattcat
tcttcttactctctcttttcttctccctccaaaagaggcatatgatgagtgtataactctgagttgagaagtattgcatctccaaatattcgactgaaatttt
gcaaagtgagaaaacattaatggagaaattgattgactcatctctctctttctctcgccaaacgag Figure 12. SEQ ID NO: 6 gaagcttacttttggatggtgggaatatattttgaacctcaatatagtcgttcaagaagaatgataacacaagtagtcaacatgaactccatcattga
tgacacttatgatgcttttgcaacttttgatgagcttatgcttttcacggatgcgatccaaag*gtaatctttctataacaactgcatttgttctgataa*
*tttttttaagatgctatttgaagtgttgttatagagaaatatattatgacaacttagactttgcag*atgggatgtaggtgccatggattcattacc
ggcatatttgagacctatttatcaaggccttctcgacgttttcaatgaaatggaagaagtaatggccaaagaaggtaaagcagatcgcatctactat
gcgaaaaaagag*gtaatccttgattaagttacattaattactacttaataagttaattaagtaaaccaagttgtagggaagaatcacaattt*
*tgaactattagtacttttttctgttactttttttag*atgaaaaagttggtggcagcctattttaaggaagttgaatggttgaatgctaactacattccaaa
atgtgaggagtatatgaaaaatggagttgtaagttgtaccggtagatgtatggaacaatttgctttggttgttatcgaggaaattataacaaaagag
gcttttgaatggttggcaaatgaacctttgattcctcgagctgcatcaacaatctgtagattaatggatgatattgttgatcatgaat*taagtataac*
*aatataatttccatttttatataacaattagtcatcctaattcacaaattttgtccctaaatacatacaaaaacaactacaataacagaaaca*
*acatatccagtgtattcctatagtacgggtctgggcagagagatgtgtatgaagatcttaccctatcttgtggaggtagaaaggttgtttcc*
*cgatagaccctcgactcaaaaaaacatttctcaatctgatttcgagtctaggtggcacttttgcatgatataataaatagacatgcttgata*
*aattacaacttcaatgagcacatttacataaagtgatttatggaactttagaaacgaactgattaaaatggtaaaatattgtataatatta*
*atgaagatattgaaatatattatgtgtag*gttgaacaacaaagaggacatgttgcttcatttgttgagtactacatgaaagaatatggaacttca
aagcaagaagcatatgttgagatgtggaaaaagatcacaaatgcgtggaaagacataaataaggaactcctgcgcgctactgcagtgatatctac
ccgcttcgcgtcggcatccggtcagtggcagtgaagggcgaacagttcctgattaaccacaaaccgttctactttactggctttggtcgtcatgaaga
tgcggacttgcgtggcaaaggattcgataacgtgctgatggtgcacgaccacgcattaatggactggattggggccaactcctaccgtacctcgcat
tacccttacgctgaagagatgctcgactgggcagatgaacatggcatcgtggtgattgatgaaactgctgctgtcggctttaacctctctttaggcatt
ggtttcgaagcgggcaacaagccgaaagaactgtacagcgaagaggcagtcaacggggaaactcagcaagcgcacttacaggcgattaaagag
ctgatagcgcgtgacaaaaaccacccaagcgtggtgatgtggagtattgccaacgaaccggatacccgtccgcaaggtgcacgggaatatttcgcg
ccactggcggaggcaacgcgtaaactcgacccgacgcgtccgatcacctgcgtcaatgtaatgttctgcgacgctcacaccgataccatcagcgat
ctctttgatgtgctgtgcctgaaccgttattacggatggtatgtccaaagcggcgatttggaaacggcagagaaggtactggaaaaagaacttctgg
cctggcaggagaaactgcatcagccgattatcatcaccgaatacggcgtggatacgttagccgggctgcactcaatgtacaccgacatgtggagtg
aagagtatcagtgtgcatggctggatatgtatcaccgcgtctttgatcgcgtcagcgccgtcgtcggtgaacaggtatggaatttcgccgattttgcg
acctcgcaaggcatattgcgcgttggcggtaacaagaaagggatcttcactcgcgaccgcaaaccgaagtcggcggcttttctgctgcaaaaacgc
tggactggcatgaacttcggtgaaaaaccgcagcagggaggcaaacaatgaattcctgcagtagcgcgcaggagttccttatttatgtctttccacg
catttgtgatcttttttccacatctcaacatatgcttcttgctttgaagttccatattctttcatgtagtactcaacaaatgaagcaacatgtcctcttttgttg
ttcaacctacacataatatatttcaatatcttcattaatattatacaatattttaccattttaatcagttcgtttctaaagttccataaatcactttatgta
aatgtgctcattgaagttgtaatttatcaagcatgtctatttattatatcatgcaaaagtgccacctagactcgaaatcagattgagaaatgttttttg
agtcgagggtctatcgggaaacaacctttctacctccacaagatagggtaagatcttcatacacatctctctgcccagacccgtactataggaatac
actggatatgttgtttctgttattgtagttgtttttgtatgtatttagggacaaaatttgtgaattaggatgactaattgttatataaaatggaaattatat
tgttatacttaattcatgatcaacaatatcatccattaatctacagattgttgatgcagctcgaggaatcaaaggttcatttgccaaccattcaaaagc
ctcttttgttataatttcctcgataacaaccaaagcaaattgttccatacatctaccggtacaacttacaactccatttttcatatactcctcacattttg
gaatgtagttagcattcaaccattcaacttccttaaaataggctgccaccaacttttctatctaaaaaagtaacagaaaaagtactaatagttcaaaa
ttgtgattcttccctacaacttggtttacttaattaacttattaagtagtaattaatgtaacttaatcaaggattacctcttttttcgcatagtagatgcga
tctgctttaccttcttggccattacttcttccatttcattgaaaacgtcgagaaggccttgataaataggtctcaaatatgccggtaatgaatccatgg
cacctacatcccatctgcaaagtctaagttgtcataatatatttctctataacaacacttcaaatagcatcttaaaaaattatcagaacaaatgcagtt
gttatagaaagattacctttggatcgcatccgtgaaaagcataagctcatcaaaagttgcaaaagcatcataagtgtcatcaatgatggagttcatg
ttgactacttgtgttatcattcttcttgaacgactatattgaggttcaaaatatattcccaccatccaaaagtaagcttc-

Figure 13. SEQ ID NO: 7

CTTCCCTCTTCTCTTTCTTCATAACCCTGTCTAAAGGGATTATTATGATAGTAGAGTC
TCACCATCGGGCTCGGAT*TCCGTAAAAGTCGAAACGCC*ACCAATTCGGCTGACACAGC
CTCGTGACATTTAAATCTTTATTGGTTTGTGAGCAGGGATTGG*AGGCGTTTTGACTTTT*
*AGGGG*ATCGGATCCTCGAGGTGTAAAAAACTCGTAAATCCTATCAGATCTGGAAG
ATTTCTACGCTTCTCCTTCTTTATATTCGTTTTCTTATGCTTTTTATTTTGATATAACC
TAGAAAAAGGCTTTTTATATCTTTGAATCCGAAATTGTTTGTTTTAGAATATTGTATA
TCTGATTTTTATCCCTTTTTATATTTGAATGTTCTTTAGTCTCCTTTTGTTTGCCCAAA
TGTTGAAT

Figure 14A SEQ ID NO: 8

```
   1 ctcgtttggc gagagaaaga gagagatgag tcaatcaatt tctccattaa tctgttctca 61 ctttgcgaaa tttcagtcga atatttggag atgcaatact tctcaactca gagttataca 121 ctcatcatat gcctcttttg gagggagaag aaaagagaga gtaagaagaa tgaatcgagc 181 aatggatctt tcttcaagct ctcgtcattt ggcagatttt ccctcaacaa tttggggtga 241 ccatttctc tcctacaatt ctgaaataac agtaagtcac aatcccatgc ttatattcta 301 ccgtcaaact tctctataac aactccattt gttgcgatcg ttttttattg ttatagtgaa 361 gtgttgttat agagattata tattataata taacatagta atcggttccg agaaaacttg 421 attctttagt gaatgactgt tatatgggga tgttatagag aggtctgact gtgttaccta 481 aatgaataat gaagatgtta taattttatt agagatggat gaagcattta aacatgaaag 541 attcaagctt taagattggt ctttatcgta cttttgaaat tatgagtttg gaatttaata 601 cttcctccgt ctcaaaaaag aatgaatctt ttactatatg gggtcaaata agattttctt 661 tggccatatt ttttgcaaat gcatttcaaa tattttgaat ttttaattgt gtgacttaca 721 ataccttta tgcagtttct aaatgtgtaa aatatatttc aaactttaa agaatattat 781 gtcatcacat taaaaatatt gaacttgact ctcatgctcc gacaggttaa ataatgaaac 841 gaatggaata ttactatttt gtaaaaactt aggtaggttt tcactatata tttaataatg 901 tattcaaact cataaataat gatcaaaagg agctttgacg ggaggtcacg ggttcgagcc 961 gtggaaacaa cctcttgcaa aaatgtaagg taagactgca tacaatagac tcttgtggtc 1021 cgccccttct ccggaccccg cacatagcgg aagcttattg cactaggctg ccctttttag
```

Figure 14B 1081 tgattaacat atgtggatct aggatttaaa ttttttgggt tcaaccttta aggatctgtt 1141 acaattttag tagaatgtta cacataaatt tgtgctccgt gaatgtattg agtcagatga 1201 acctggtatt atacatgcgg atacgctcct gatgctcaat ttctgcctgc aggaaattac 1261 tacccaagag aaaaatgaac atgaaatgct aaaagaaata gttcggaaaa tgttggtaga 1321 aactccagat aatagtacac aaaaactagt cttgattgac acaattcaaa gattgggatt 1381 agcatatcat ttcaatgatg agattgaaaa ctccattcaa aacatcttta atttgtctca 1441 aaatagtgaa gatgacgatg aacacaacct ttatgttgct gctcttcgtt ttcgacttgc 1501 gaggcaacaa ggatattaca tgtcttcagg taccttacat ttctgccctt tcccgcacag 1561 cttcattttt tttcgttgtt aaaagacagt tcggcgcata aaatatctca tgtatacgcc 1621 agggtcagga cgaaccgccc ccaaggggtg taaagtatgc aacttaccct aatactaaat 1681 atctcgtgta tacacagggt caggacaagt cgcacccaag gggtgtaatg tagacaactt 1741 atcctaatgc tattagtaac tgattttatg gctcgaacac ataaattata ggtcacacag 1801 taacaacttt accgttgctc aaagactcgc cttcctcttt ttttagttat cgcaccttat 1861 ttgtgcagag aatagcaagt ttcgagatct gcttctatat agaagacttc tgtattatac 1921 tttttttattt tgtccttctg cttaaaaata gtaaaaaact atagtgtgga aattgtaaat 1981 ttcttaacta gctgtgaaat caaatagtta ttataggaat attatttaag actccactta 2041 tggaaaacca ctgggttgtt gttgttattg tcaataataa cttggggtac gatttacttc 2101 tttttccatg gcttgtccac gactatattt ctattaacaa tgttgtgact atgctttctt 2161 tgagtcgagg gtctattgat aacaggctct cgatctttac aaggtaaaag taatgtctgc 2221 gtacaccact ctactccgca gactccactt gtaggatttc actgaatatt ttttgttgtt 2281 gttgttgttg taataactta gggtttaatt tcttgatgct aatgaaattc atttctttca 2341 aaatataaac atggtgttca accagatgtg ttcaagcaat tcactaacca tgacggaaaa 2401 ttcaaggaaa atcatactaa tgatgttcaa ggattattga gtttgtatga agcagcacat 2461 atgagagtgc acgacgagga aattctagaa gaagctctta tctttaccac gactcatctc

Figure 14C 2521 gagtccgtga tcccgaattt gagcaactcg cttaaggtac aagttactga agccttaagc 2581 catcctattc gcaaagctat accaagggtg ggagcaagga aatacataca catatatgaa 2641 aacattggaa cacataatga tttacttttg aaatttgcaa agttggactt caacatgtta 2701 caaaagcttc atcgaaaaga gcttaacgag ctaacaaggt acatctacta ttcttgtcat 2761 cttcataatt atggtacaat cagacctctc tctataaaat acatccttta taacaacagt 2821 tcactataac ggtcaagttt tctttaaaat caatgtttta tgttaccaaa ttattttgaa 2881 agaaatgtga ctattataga gaggtttgac tgtaactcgc gctaattaat aacacctaaa 2941 gtttaagtat gttaatgctg ttatgatatc tatagctggt ggaaagattt ggatcgtgca 3001 aacaaatttc catatgcaaa ggacagatta gtagaagctt acttttggac ggtgggaata 3061 tattttgaac ctcaatatag tcgttcaaga agtttggtaa caaaagtagt caaaatgaac 3121 tccattattg atgacactta tgatgcttat gcaacttttg atgagcttgt gcttttcacg 3181 gatgcgatcc aaaggtaaaa ttatatataa taaaatcttt ctataacaac gtcatttatt 3241 ctgatatttt tttaagatgc tatagtgaag tattgttata tagaaatata ttatgacaac 3301 ttagactttg cagatgggac gaaggtgcca tggatttatt accgacatat ctgagaccta 3361 tttatcaagg ccttctcgac gttttcaatg aaatggaaga agtattggcc aaagaaggta 3421 aagcagatca catctactat gcgaaaaaag aggtaatcct tgattaagtt acattaatta 3481 ctacttaata gttaattaag taaaccaagt tgtagggaag aatcgcaatt ttgaactatt 3541 agtacatttt ctgttacttt tttagatgaa aaaggtggcg gaagtctatt ttaaggaagc 3601 tgaatggttg aatgctaact acattccaaa atgcgaggag tatatgaaaa atggacttgt 3661 aagctctacc ggtccgatgt atggaataat ttctttggtt gttatggagg aaattataac 3721 aaaagaggct tttgaatggt tgacaaatga acctttgatt cttcgagctg catcaacaat 3781 ttgtagatta atggatgata tggctgatca tgaagtaagt ataacaatat aattttcatt 3841 ttatataaca atagccatcg taattcgcga attttgtccc taaatacaat acaaaaacaa 3901 ctacaataac aaaaacaaca tatccaatat attcctacag tacgggtcta ggaagagaga

Figure 14D 3961 tgtgtacgca gatcttaccc taccttatag aggtagaaat gttgttcccg atagaccctc 4021 gactcaaaaa aagcatttct cagtctgatt tcgagtctag gtggcacttt tgcatgataa 4081 aataaataga catgcttgat aaattacaac ttcaatgatc acatttactt aaactgaatt 4141 atggaacttt agaaacggct gattaaaatg gtaaaatatt gtaataat gaagaaattg 4201 aaatatatta tgttgtaggt tgaacaacaa agaggacatg ttgcttcatt tgttgagtgc 4261 tacatgaaag aatatggagt ttcaaagcaa gaaacatatg ttgagatgcg gaaaaaaatc 4321 acaaatgcgt ggaaagatat aaataaggaa ctcttgcgcc ctactgcagt accaatgttt 4381 atcctcgaac gatctttaaa tttttcaaga ttggccgata catttttgaa agatgatgat 4441 ggatacacaa atcccaaatc caaagttaaa gacttgattg cttcgttgtt tgtcgaatct 4501 gtcgacatat gattatatat aacaatgcag a Figure 15A SEQ ID NO: 9

1 gctgccttt ttttttttgg gctacaaaac tctaaagtaa aggaactaga aaactcgttt 61 ggcgagagaa agagagagat gagtcaatca atttctccat taatgttttc tcactttgca 121 aaatttcagt cgaatatttg gagatgcaat acttctcaac tcagagttat acactcatca 181 tatgcctctt ttggagggag aagaaaagag agagtaagaa gaatgaatcg agcaatggat 241 ctttcttcaa gctctcgtca tttggcagat tttccctcaa caatttgggg tgaccatttt 301 ctctcctaca attctgaaat aacagaaatt actacccaag agaaaaatga acatgaaatg 361 ctaaaagaaa tagttcggaa aatgttggta gaaactccag ataatagtac acaaaaacta 421 gtcttgattg acacaattca aagattggga ttagcatatc atttcaatga tgagattgaa 481 aactccattc aaaacatctt taatttgtct caaaatagtg aagatgacga tgaacacaac 541 ctttatgttg ctgctcttcg ttttcgactt gcgaggcaac aaggatatta catgtcttca 601 gatgtgttca agcaattcac taaccatgac ggaaaattca aggaaaatca tactaatgat 661 gttcaaggat tattgagttt gtatgaagca gcacatatga gagtgcacga cgaggaaatt

Figure 15B

```
 721 ctagaagaag ctcttatctt taccacgact catctcgagt ccgtgatccc gaatttgagc 781 aactcgctta aggtacaagt tactgaagcc ttaagccatc ctattcgcaa agctatacca 841 agggtgggag caaggaaata catacacata tatgaaaaca ttggaacaca taatgattta 901 cttttgaaat ttgcaaagtt ggacttcaac atgttacaaa agcttcatcg aaaagagctt 961 aacgagctaa caagctggtg gaaagatttg gatcgtgcaa acaaatttcc atatgcaaag 1021 gacagattag tagaagctta cttttggacg gtgggaatat attttgaacc tcaatatagt 1081 cgttcaagaa gtttggtaac aaaagtagtc aaaatgaact ccattattga tgacacttat 1141 gatgcttatg caacttttga tgagcttgtg cttttcacgg atgcgatcca agatgggac 1201 gaaggtgcca tggatttatt accgacatat ctgagaccta tttatcaagg ccttctcgac 1261 gttttcaatg aaatggaaga agtattggcc aaagaaggta agcagatca catttactat 1321 gcgaaaaaag agatgaaaaa ggtggcggaa gtctatttta aggaagctga atggttgaat 1381 gctaactaca ttccaaaatg cgaggagtat atgaaacatg gacttgtaag ctctaccggt 1441 ccgatgtatg gaataatttc tttggttgtt atggaggaaa ttataacaaa agaggctttt 1501 gaatggttga caaatgaacc tttgattctt cgacctgcat caacaatttg tagattaatg 1561 gatgatatgg ctgatcatga agttgaacaa caaagaggac atgttgcttc atttgttgag 1621 tgctacatga aagaatatgg agtttcaaag caagaagcat atgttgagat gcggaaaaaa 1681 atcacaaatg cgtggaaaga tataaataag gaactcttgc gccctactgc agtaccaatg 1741 tttatcctcg aacgatcttt aaattttttca agattggccg atacatttt gaaagatgat 1801 gatggataca caaatcccaa atccaaagtt aaagacttga ttgcttcgtt gtttgtcgaa 1861 tctgtcgaca tatgattata tataacaatg cagacacacc ttcaaagctg agtatttgga 1921 gcaaatatgg aagcattttg tattgtccat gtaaccctat aagtcacgtg tttgggcaat 1981 ggcaacattt actaatattt gcattatggt aggttgttta catcacacct attgggggcg 2041 acccttccta aaacctgaca tgaatgtgtg atgctttgtg cacctggcgg ctcattttta 2101 ctatttcact gttacaactt atttggacgg ttgttaacct attgaatcat gtagtattgt
```

Figure 15C

2161 tacttaaata caatgtttat tttaattatt acttaaattt tattctatca tatcgttaaa 2221 tccatcatta cgtaacaaaa aaaaaaaaaa a

Figure 16. SEQ ID NO: 10

MSQSISPLMFSHFAKFQSNIWRCNTSQLRVIHSSYASFGGRRKE

RVRRMNRAMDLSSSSRHLADFPSTIWGDHFLSYNSEITEITTQEKNEHEMLKEIVRKM

LVETPDNSTQKLVLIDTIQRLGLAYHFNDEIENSIQNIFNLSQNSEDDDEHNLYVAAL

RFRLARQQGYYMSSDVFKQFTNHDGKFKENHTNDVQGLLSLYEAAHMRVHDEEILEEA

LIFTTTHLESVIPNLSNSLKVQVTEALSHPIRKAIPRVGARKYIHIYENIGTHNDLLL

KFAKLDFNMLQKLHRKELNELTSWWKDLDRANKFPYAKDRLVEAYFWTVGIYFEPQYS

RSRSLVTKVVKMNSIIDDTYDAYATFDELVLFTDAIQRWDEGAMDLLPTYLRPIYQGL

LDVFNEMEEVLAKEGKADHIYYAKKEMKKVAEVYFKEAEWLNANYIPKCEEYMKHGLV

SSTGPMYGIISLVVMEEIITKEAFEWLTNEPLILRPASTICRLMDDMADHEVEQQRGH

VASFVECYMKEYGVSKQEAYVEMRKKITNAWKDINKELLRPTAVPMFILERSLNFSRL

ADTFLKDDDGYTNPKSKVKDLIASLFVESVDI

Figure 17. SEQ ID NO: 11

CTTCCCTCTTCTCTTTCTTCATAACCCTGTCTAAAGGGATTATTATGATAGTAGAGTCTCACCATCGGGCTCGGAT*TC*
*GAAGAAATCATCCACCGCT*CCAATTCGGCTGACACAGCCTCGTGACATTTAAATCTTTATTGGTTTGTGAGCAGGG
ATTGG*AGCGGTGGAGGATTTCTTAGT*ATCGGATCCTCGAGGTGTAAAAAAACTCGTAAATCCTATCAGATCTGGA
AGATTTCTACGCTTCTCCTTCTTTATATTCGTTTTCTTATGCTTTTTATTTTTGATATAACCTAGAAAAGGCTTTTTAT
ATCTTTGAATCCGAAATTGTTTGTTTTAGAATATTGTATATCTGATTTTTATCCCTTTTTATATTTGAATGTTCTTTAGT
CTCCTTTTGTTTGCCCAAATGTTGAAT

SEQUENCE LISTING

```
<160> NUMBER OF SEQ ID NOS: 11

<210> SEQ ID NO 1
<211> LENGTH: 4624
<212> TYPE: DNA
<213> ORGANISM: Nicotiana tabacum

<400> SEQUENCE: 1
ccttatattt atccaccact tgagctactt tctataacca attaaagtaa gtccaattct      60
aacattgtat gctgtgctgc ccttattttt ggctacaaaa ctcgaaagca aaggaactag     120
aaaactcgtc tggcgagaga aagagagatg agtcaatcaa tttctccaat ctttcctcgc     180
tttgcaaaat ttcagtcgaa tatttggagg tgcagtactt ttgaactcag agttatacac     240
tcatcatatg cctctattgg agggaggaga aaagagagag aaagaagaat gaagcgagca     300
atgaatcctt cttcaagctc gcgtcatttg gcagattttc actcaaccat ttggggtgac     360
```

```
cattttctct cctacaattc tgaaataaca gtaggtcaca tacatatgta atcacatgct    420
tatattctat ttgaatttgt tatctaaatg tttaaaggaa taaagatgtt ataattttat    480
tagagacagg atcaagcatt taaacttgga aggtttaacc tttaagattg gtctttatcg    540
tacttttgaa attatgagtt tgaaatttaa tactccatcc gtctcaataa agaatgaata    600
ttttactatc tagggagtca acaagatttt tctcaacctt ttttttcgca aatgcatttt    660
aaaaattttg aaattttaa ttgttgtgac ttacaactac cttcttatgt acttcctaaa    720
tgtgtaaatc tcattttcaa aaatttacg gaatatatat tcgtcacatt gaaaatattt    780
aatttgaccc tcatactccg aaaaggttca aataaattga aacgaatgga atagtactat    840
tttgtaaaaa cttatgtaga ttttcactat atatctaata agtattcaaa actaataaat    900
aatgatcaac atatgcggat ctaagattta aattttttgg gttcaccttt aaggatctgt    960 tacaattta gtagaatgtt accataaatt tgtgctccgt gaaatgtatt gagtcagatg    1020
aacctggtat tatacatgcg gatacgctcc tgatgctcaa tttctgcctg caggaaatta    1080
ctacccaaga gaaaaatgaa catgaaatgc taaaagaaat agttcggaaa atgttggtag    1140
aaactccaga aatagtaca caaaaactag tcttgattga cacaattcaa agattgggat    1200
tagcatatca tttcaatgat gagattgaaa actccattca aaacatcttt aatttgtctc    1260
aaaatagtga aaatgacaat gaacacaacc tttatgttgc tgctcttcgt tttcgacttg    1320
cgaggcaaca aggatattac atgtcttcag gtaccttaca tttctgccct ttcccgcaca    1380
gcttcatttt ttttcgttgt taaaggcagc tcggcgtata aatatctcg tgtatacgca    1440 gggtcaggac ggaaccgccc ccaaggggtg taaagtatgc aacctaccct aatactaaat    1500
atctcgtgtt atacacaggg tcaggacaag tcgcacccaa gaggtgtaat gtaggcaact    1560
taccctaatg ctagcattag taactgattt tatggctcaa acacataaat tgtaggtcac    1620
acagtaacaa ctttatcgtt ctcaaagact cgccttcctc tttttttagt tatcgcacct    1680
tatttgttgc aaagaatagc aagtttcgag atctgcttct atataaaaaa cttctgtatt    1740
atactttttt attttgtcct tctgcttaaa aatagtaaaa aactataatg tggaaattgt    1800
aaattcttta actagctgtg aaatcaaata gttattatag gaatataatt tagactccac    1860
ttatggaaaa ccactgggtt gccgttgtta ttgtcaataa taacttgggg tacgatttac    1920 ttcttttcc atggctgtcc acgactatat ttctattaac caatgttgtg actatgcttt    1980
cccttgagtc gaggatctat tgataacagg ctcttcgatc tttaacaagg taaaagtaat    2040
gtctgcgtac acactctact ccgcagaccc acttgtagga tttcattgaa ttttttttt    2100 tgttgttgtt gttgtaataa cttagggttt agtttcttga tgctgatgaa attcagttct    2160
ttcaactata aacatggtgt tcaccagatg tgttcaagca attcactaac catgacggaa    2220
aattcaagga aaatcatatt aatgatattc aaggattact aagtttgtat gaagcaacac    2280
atatgagagt gcacgacgag gaaattctag aagaagctct tatctttacc accactcatc    2340
tcgagtccat gatcccaaat ttgagcaact cgcttaaggt acaagttact gaagcctcaa    2400
accaacctat tcgcaaaact ataccgaggg tgggatcaag gaaatacata tacatatatg    2460
aaaacattgg aacacataat gatttgcttg tgaaatttgc aaagtggac tttaacatgt    2520 tacaagagct tcatcgaaaa gagctcaacg agctaacaag gtacatctac tattcttatc    2580
attttcatag ttatggtaca gtcagatctc tctataaaat ccatccttta taacaacggt    2640
tcaccataac ggtcatgttt tctttagaac taatctttta tgttaccaaa aaatttcgaa    2700
acaattgaga ctattataga gatgtttgat ggtaactcgc gctaattaat aacacctaaa    2760
```

```
gtttaagtat gttaatgttg ttgtgttatc tatagctggt ggaaagaaat ggattttgca    2820
acaaatttcc aatatgcaaa gggcagattg gtagaagctt acttttggat ggtgggaata    2880
tattttgaac ctcaatatag tcgttcaaga agaatgataa cacaagtagt caacatgaac    2940
tccatcattg atgacactta tgatgctttt gcaacttttg atgagcttat gcttttcacg    3000
gatgcgatcc aaaggtaatc tttctataac aactgcattt gttctgataa ttttttaaga    3060
tgctatttga agtgttgtta tagagaaata tattatgaca acttagactt tgcagatggg    3120
atgtaggtgc catggattca ttaccggcat atttgagacc tatttatcaa ggccttctcg    3180
acgttttcaa tgaaatggaa gaagtaatgg ccaaagaagg taaagcagat cgcatctact    3240
atgcgaaaaa agaggtaatc cttgattaag ttacattaat tactacttaa taagttaatt    3300
aagtaaacca agttgtaggg aagaatcaca attttgaact attagtactt tttctgttac    3360 tttttttagat gaaaaagttg gtggcagcct attttaagga agttgaatgg ttgaatgcta    3420
actacattcc aaaatgtgag gagtatatga aaaatggagt tgtaagttgt accggtagat    3480
gtatggaaca atttgctttg gttgttatcg aggaaattat aacaaaagag gcttttgaat    3540
ggttggcaaa tgaaccttg attcctcgag ctgcatcaac aatctgtaga ttaatggatg    3600
atattgttga tcatgaatta agtataacaa tataatttcc attttatata caattagtc    3660 atcctaattc acaaattttg tccctaaata catacaaaaa caactacaat aacagaaaca    3720
acatatccag tgtattccta tagtacgggt ctgggcagag agatgtgtat gaagatctta    3780
ccctatcttg tggaggtaga aaggttgttt cccgatagac cctcgactca aaaaaacatt    3840
tctcaatctg atttcgagtc taggtggcac ttttgcatga tataataaat agacatgctt    3900
gataaattac aacttcaatg agcacatttta cataaagtga tttatggaac tttagaaacg    3960
aactgattaa aatggtaaaa tattgtataa tattaatgaa gatattgaaa tatattatgt    4020
gtaggttgaa caacaaagag gacatgttgc ttcatttgtt gagtactaca tgaaagaata    4080
tggaacttca aagcaagaag catatgttga gatgtggaaa aagatcacaa atgcgtggaa    4140
agacataaat aaggaactcc tgcgcgctac tgcagtacca atgtttgtcc tcgaacgaac    4200
tttagattat acaagattgg ttgatacatg tttcaaagat gatgatggtt acacaaatcc    4260
caaatccaaa gtgaaagaca tgattgcttt gttgtttgtc gaatctatcg acatatgatg    4320
atatataaca atgcagatgc accttcaacc gagtattcag agcaaatatg gaagcatttt    4380
gtatggttct gtatgaccta taggtcatat gttcgagtca tggaagcatc cattaatact    4440
tgcattaggg taggctgtct atatcatact tattagggtg cgacccttcc cctgactctg    4500
catgaatgca ggatgctttg tgcgctcagc tgcctttttt tactatttcg ctgtcagtta    4560
tgtttgagaa gggacaatac ttgatttgat tcatgcagtc ttgtctccag gtttgattcc    4620
tatg                                                                4624
```

<210> SEQ ID NO 2
<211> LENGTH: 597
<212> TYPE: PRT
<213> ORGANISM: Nicotiana tabacum

<400> SEQUENCE: 2

Met Ser Gln Ser Ile Ser Pro Ile Phe Pro Arg Phe Ala Lys Phe Gln
1               5                   10                  15

Ser Asn Ile Trp Arg Cys Ser Thr Phe Glu Leu Arg Val Ile His Ser
            20                  25                  30

```
Ser Tyr Ala Ser Ile Gly Gly Arg Arg Lys Glu Arg Arg Met
        35              40              45
Lys Arg Ala Met Asn Pro Ser Ser Ser Arg His Leu Ala Asp Phe
50                      55                  60
His Ser Thr Ile Trp Gly Asp His Phe Leu Ser Tyr Asn Ser Glu Ile
65                  70              75                  80
Thr Glu Ile Thr Thr Gln Glu Lys Asn Glu His Glu Met Leu Lys Glu
                85                  90                  95
Ile Val Arg Lys Met Leu Val Glu Thr Pro Asp Asn Ser Thr Gln Lys
            100                 105                 110
Leu Val Leu Ile Asp Thr Ile Gln Arg Leu Gly Leu Ala Tyr His Phe
            115                 120                 125
Asn Asp Glu Ile Glu Asn Ser Ile Gln Asn Ile Phe Asn Leu Ser Gln
130                 135                 140
Asn Ser Glu Asn Asp Asn Glu His Asn Leu Tyr Val Ala Ala Leu Arg
145                 150                 155                 160
Phe Arg Leu Ala Arg Gln Gln Gly Tyr Tyr Met Ser Ser Asp Val Phe
                165                 170                 175
Lys Gln Phe Thr Asn His Asp Gly Lys Phe Lys Glu Asn His Ile Asn
            180                 185                 190
Asp Ile Gln Gly Leu Leu Ser Leu Tyr Glu Ala Thr His Met Arg Val
            195                 200                 205
His Asp Glu Glu Ile Leu Glu Glu Ala Leu Ile Phe Thr Thr Thr His
            210                 215                 220
Leu Glu Ser Met Ile Pro Asn Leu Ser Asn Ser Leu Lys Val Gln Val
225                 230                 235                 240
Thr Glu Ala Ser Asn Gln Pro Ile Arg Lys Thr Ile Pro Arg Val Gly
                245                 250                 255
Ser Arg Lys Tyr Ile Tyr Ile Tyr Glu Asn Ile Gly Thr His Asn Asp
                260                 265                 270
Leu Leu Val Lys Phe Ala Lys Leu Asp Phe Asn Met Leu Gln Glu Leu
            275                 280                 285
His Arg Lys Glu Leu Asn Glu Leu Thr Ser Trp Trp Lys Glu Met Asp
            290                 295                 300
Phe Ala Thr Asn Phe Gln Tyr Ala Lys Gly Arg Leu Val Glu Ala Tyr
305                 310                 315                 320
Phe Trp Met Val Gly Ile Tyr Phe Glu Pro Gln Tyr Ser Arg Ser Arg
                325                 330                 335
Arg Met Ile Thr Gln Val Val Asn Met Asn Ser Ile Ile Asp Asp Thr
            340                 345                 350
Tyr Asp Ala Phe Ala Thr Phe Asp Glu Leu Met Leu Phe Thr Asp Ala
            355                 360                 365
Ile Gln Arg Trp Asp Val Gly Ala Met Asp Ser Leu Pro Ala Tyr Leu
370                 375                 380
Arg Pro Ile Tyr Gln Gly Leu Leu Asp Val Phe Asn Glu Met Glu Glu
385                 390                 395                 400
Val Met Ala Lys Glu Gly Lys Ala Asp Arg Ile Tyr Tyr Ala Lys Lys
                405                 410                 415
Glu Met Lys Lys Leu Val Ala Ala Tyr Phe Lys Glu Val Glu Trp Leu
            420                 425                 430
Asn Ala Asn Tyr Ile Pro Lys Cys Glu Glu Tyr Met Lys Asn Gly Val
            435                 440                 445
Val Ser Cys Thr Gly Arg Cys Met Glu Gln Phe Ala Leu Val Val Ile
```

| | | | | | | | | | | | | |
|---|---|---|---|---|---|---|---|---|---|---|---|---|
| | | 450 | | | | 455 | | | | 460 | | |
| Glu | Glu | Ile | Ile | Thr | Lys | Glu | Ala | Phe | Glu | Trp | Leu | Ala | Asn | Glu | Pro |
| 465 | | | | | 470 | | | | | 475 | | | | | 480 |
| Leu | Ile | Pro | Arg | Ala | Ala | Ser | Thr | Ile | Cys | Arg | Leu | Met | Asp | Asp | Ile |
| | | | | 485 | | | | | 490 | | | | | 495 | |
| Val | Asp | His | Glu | Val | Glu | Gln | Gln | Arg | Gly | His | Val | Ala | Ser | Phe | Val |
| | | | 500 | | | | | 505 | | | | | 510 | | |
| Glu | Tyr | Tyr | Met | Lys | Tyr | Gly | Thr | Ser | Lys | Gln | Glu | Ala | Tyr | Val | |
| | | | | 515 | | | | | 520 | | | | | 525 | |
| Glu | Met | Trp | Lys | Lys | Ile | Thr | Asn | Ala | Trp | Lys | Asp | Ile | Asn | Lys | Glu |
| | | | 530 | | | | | 535 | | | | | 540 | | |
| Leu | Leu | Arg | Ala | Thr | Ala | Val | Pro | Met | Phe | Val | Leu | Glu | Arg | Thr | Leu |
| 545 | | | | | 550 | | | | | 555 | | | | | 560 |
| Asp | Tyr | Thr | Arg | Leu | Val | Asp | Thr | Cys | Phe | Lys | Asp | Asp | Asp | Gly | Tyr |
| | | | | 565 | | | | | 570 | | | | | 575 | |
| Thr | Asn | Pro | Lys | Ser | Lys | Val | Lys | Asp | Met | Ile | Ala | Leu | Leu | Phe | Val |
| | | | 580 | | | | | 585 | | | | | 590 | | |
| Glu | Ser | Ile | Asp | Ile | | | | | | | | | | | |
| | | | | 595 | | | | | | | | | | | |

```
<210> SEQ ID NO 3
<211> LENGTH: 2433
<212> TYPE: DNA
<213> ORGANISM: Nicotiana tabacum

<400> SEQUENCE: 3
tgcagccaca gtactgcttc atcaatggaa gaggcaaagg agagaataag ggaaacattt      60
ggaaaaatag agctatctcc ttcttcctat gacacagcat gggtagctat ggtcccttca     120
agatattcta tgaaccaacc atgttttcct cagtgcttag attggattct tgaaaatcaa     180
agagaagatg gatcttgggg cctaaatcct agccatccat tgcttgtaaa agactccctt     240
tcttccactc tagcatcttt gcttgccctt cgcaaatgga gaattggaga taaccaagtc     300
caaagaggcc ttggctttat tgaaacgcat ggttgggcag tcgataacaa ggatcagatt     360
tcacctttag gatttgaaat tatatttccc tgcatgacca actatgcaga gaaacttaat     420
ttggatctac ctttggatcc taaccttgta aatatgatgc tctgcgaacg tgaattaaca     480
attgaaagag cctaaagaa tgaattcgag gggaatatgg caaatgtaga atattttgct     540
gaaggactcg gtgaatcatg tcattggaaa gagatgatgc ttcgtcagag acacaacggg     600
tcgctctttg attcaccagc cactactgca gctgccttga tttaccatca gtacgatgag     660
aaatgctttg ggtacttgaa ctcaatcttg aaactgcacg ataattgggt ccacactatt     720
tgccctacaa agatacattc aaatctcttc ttagttgatg cccttcaaaa tcttggagta     780
gatcggtatt ttaaaacaga agtcaaaaga gtactagatg aaatatacag gctttggcta     840
gaaaagaatg aagaaatttt ttcagacgtt gctcattgtg ccatggcgtt tcgactttta     900
cggatgaata actatgaagt ttcctcagaa gaacttgaag gatttgtcga ccaagaacat     960
ttctttacaa catcaagtgg gaaacttatg aatcacgttg caattctcga acttcaccga    1020
gcttcacagg tggctattca tgaaggaaa gatcacattt tagataaaat aagtacttgg    1080
acaaggaatt ttatggagca aaaactcttg gacaagcaca tccctgatag gtcaaagaag    1140
gagatggaat tgctatgag gaaatttat ggcacatttg atcgagtgga aactagacgt    1200
tacatcgagt catacaaaat ggacagtttt aagatcttaa aagcggctta caggtcttcc    1260
```

-continued

```
ggtattaaca acatagactt gctaaagttc tcagaacacg attttaactt gtgccaaacc   1320
cgacacaaag aagaacttca acagatgaaa aggtggttca cagattgcaa actcgaacaa   1380
gtaggattat cacaacagta cttatacact agttacttca taattgctgc tatactcttt   1440
gaacctgaat atgctgatgc tcgtctagca tatgcaaagt acgccataat aataacagcg   1500
gtggatgatt tcttcgattg ttttatttgc aaagaagaac tgcaaaacat catcgaatta   1560
gtagagagat gggagggata ctcaaccgtc ggattccgtt cagagagggt tagaattttc   1620
ttttttggcac tttacaaaat ggtagaggaa attgcggcaa aggcggaaac taagcaaggt   1680
cgatgtgtca agatcacct tattaacttg tggattgata tgttgaagtg tatgctagtg   1740
gaattggacc tttggaaaat taaatcaact accccaagca tagaggagta cttgtctgtt   1800
gcatgtgtaa ctattggtgt tccatgtttt gttctcacat cactatatct tcttggacca   1860
aaactgtcca aggatgtcat agaaagttct gaggtcagtg ccttatgcaa ttgtacagct   1920
gctgtggccc gattgattaa tgatatacac agttacaaga gaacaagc agaaagttca   1980
acaaatatgg tatcaatatt aataacacaa agtcaggaa ctatctctga agaagaggct   2040
ataagacaga taaaggaaat gatggaaagt aagagaagag agttgctagg gatggttcta   2100
caaaataaag aaagccaatt gccacaagtg tgcaaggatc ttttttggac gacaatcaac   2160
gcagcagctt attctataca tacacatggg cgatgggtat cgcttcccag aggaattcaa   2220
gaaccatatc aacgatgtaa tttacaaacc actcaatcaa tattccccat aatatgcctt   2280
aaatctttta caatatgtta ctaatctttg gaacttggtt gtgatattat tagatgcatg   2340
gacgaattgt acttctttta tgttgtgcac aataatgtac aactgttact atgggaaaaa   2400
cttacttaca ctgctaaaaa aaaaaaaaaa aaa                                2433
```

<210> SEQ ID NO 4
<211> LENGTH: 759
<212> TYPE: PRT
<213> ORGANISM: Nicotiana tabacum

<400> SEQUENCE: 4

```
Met Glu Glu Ala Lys Glu Arg Ile Arg Glu Thr Phe Gly Lys Ile Glu
1               5                   10                  15

Leu Ser Pro Ser Ser Tyr Asp Thr Ala Trp Val Ala Met Val Pro Ser
            20                  25                  30

Arg Tyr Ser Met Asn Gln Pro Cys Phe Pro Gln Cys Leu Asp Trp Ile
        35                  40                  45

Leu Glu Asn Gln Arg Glu Asp Gly Ser Trp Gly Leu Asn Pro Ser His
    50                  55                  60

Pro Leu Leu Val Lys Asp Ser Leu Ser Ser Thr Leu Ala Ser Leu Leu
65                  70                  75                  80

Ala Leu Arg Lys Trp Arg Ile Gly Asp Asn Gln Val Gln Arg Gly Leu
                85                  90                  95

Gly Phe Ile Glu Thr His Gly Trp Ala Val Asp Asn Lys Asp Gln Ile
            100                 105                 110

Ser Pro Leu Gly Phe Glu Ile Ile Phe Pro Cys Met Thr Asn Tyr Ala
        115                 120                 125

Glu Lys Leu Asn Leu Asp Leu Pro Leu Asp Pro Asn Leu Val Asn Met
    130                 135                 140

Met Leu Cys Glu Arg Glu Leu Thr Ile Glu Arg Ala Leu Lys Asn Glu
145                 150                 155                 160

Phe Glu Gly Asn Met Ala Asn Val Glu Tyr Phe Ala Glu Gly Leu Gly
```

```
                165                 170                 175
Glu Ser Cys His Trp Lys Glu Met Met Leu Arg Gln Arg His Asn Gly
            180                 185                 190

Ser Leu Phe Asp Ser Pro Ala Thr Thr Ala Ala Leu Ile Tyr His
        195                 200                 205

Gln Tyr Asp Glu Lys Cys Phe Gly Tyr Leu Asn Ser Ile Leu Lys Leu
    210                 215                 220

His Asp Asn Trp Val His Thr Ile Cys Pro Thr Lys Ile His Ser Asn
225                 230                 235                 240

Leu Phe Leu Val Asp Ala Leu Gln Asn Leu Gly Val Asp Arg Tyr Phe
                245                 250                 255

Lys Thr Glu Val Lys Arg Val Leu Asp Glu Ile Tyr Arg Leu Trp Leu
            260                 265                 270

Glu Lys Asn Glu Glu Ile Phe Ser Asp Val Ala His Cys Ala Met Ala
        275                 280                 285

Phe Arg Leu Leu Arg Met Asn Asn Tyr Glu Val Ser Ser Glu Glu Leu
    290                 295                 300

Glu Gly Phe Val Asp Gln Glu His Phe Phe Thr Thr Ser Ser Gly Lys
305                 310                 315                 320

Leu Met Asn His Val Ala Ile Leu Glu Leu His Arg Ala Ser Gln Val
                325                 330                 335

Ala Ile His Glu Arg Lys Asp His Ile Leu Asp Lys Ile Ser Thr Trp
            340                 345                 350

Thr Arg Asn Phe Met Glu Gln Lys Leu Leu Asp Lys His Ile Pro Asp
        355                 360                 365

Arg Ser Lys Lys Glu Met Glu Phe Ala Met Arg Lys Phe Tyr Gly Thr
    370                 375                 380

Phe Asp Arg Val Glu Thr Arg Arg Tyr Ile Glu Ser Tyr Lys Met Asp
385                 390                 395                 400

Ser Phe Lys Ile Leu Lys Ala Ala Tyr Arg Ser Ser Gly Ile Asn Asn
                405                 410                 415

Ile Asp Leu Leu Lys Phe Ser Glu His Asp Phe Asn Leu Cys Gln Thr
            420                 425                 430

Arg His Lys Glu Glu Leu Gln Gln Met Lys Arg Trp Phe Thr Asp Cys
        435                 440                 445

Lys Leu Glu Gln Val Gly Leu Ser Gln Gln Tyr Leu Tyr Thr Ser Tyr
    450                 455                 460

Phe Ile Ile Ala Ala Ile Leu Phe Glu Pro Glu Tyr Ala Asp Ala Arg
465                 470                 475                 480

Leu Ala Tyr Ala Lys Tyr Ala Ile Ile Thr Ala Val Asp Asp Phe
                485                 490                 495

Phe Asp Cys Phe Ile Cys Lys Glu Leu Gln Asn Ile Ile Glu Leu
            500                 505                 510

Val Glu Arg Trp Glu Gly Tyr Ser Thr Val Gly Phe Arg Ser Glu Arg
        515                 520                 525

Val Arg Ile Phe Phe Leu Ala Leu Tyr Lys Met Val Glu Glu Ile Ala
    530                 535                 540

Ala Lys Ala Glu Thr Lys Gln Gly Arg Cys Val Lys Asp His Leu Ile
545                 550                 555                 560

Asn Leu Trp Ile Asp Met Leu Lys Cys Met Leu Val Glu Leu Asp Leu
                565                 570                 575

Trp Lys Ile Lys Ser Thr Thr Pro Ser Ile Glu Glu Tyr Leu Ser Val
            580                 585                 590
```

```
Ala Cys Val Thr Ile Gly Val Pro Cys Phe Val Leu Thr Ser Leu Tyr
        595                 600                 605

Leu Leu Gly Pro Lys Leu Ser Lys Asp Val Ile Glu Ser Ser Glu Val
    610                 615                 620

Ser Ala Leu Cys Asn Cys Thr Ala Ala Val Ala Arg Leu Ile Asn Asp
625                 630                 635                 640

Ile His Ser Tyr Lys Arg Glu Gln Ala Glu Ser Ser Thr Asn Met Val
                645                 650                 655

Ser Ile Leu Ile Thr Gln Ser Gln Gly Thr Ile Ser Glu Glu Glu Ala
            660                 665                 670

Ile Arg Gln Ile Lys Glu Met Met Glu Ser Lys Arg Arg Glu Leu Leu
        675                 680                 685

Gly Met Val Leu Gln Asn Lys Glu Ser Gln Leu Pro Gln Val Cys Lys
    690                 695                 700

Asp Leu Phe Trp Thr Thr Ile Asn Ala Ala Ala Tyr Ser Ile His Thr
705                 710                 715                 720

His Gly Arg Trp Val Ser Leu Pro Arg Gly Ile Gln Glu Pro Tyr Gln
                725                 730                 735

Arg Cys Asn Leu Gln Thr Thr Gln Ser Ile Pro Ile Ile Cys Leu
            740                 745                 750

Lys Ser Phe Thr Ile Cys Tyr
        755
```

<210> SEQ ID NO 5
<211> LENGTH: 2352
<212> TYPE: DNA
<213> ORGANISM: Artificial Sequence
<220> FEATURE:
<223> OTHER INFORMATION: ddRNAiDNA construct (GW1) insert sequence

<400> SEQUENCE: 5

```
ctcgtttggc gagagaaaga gagagatgag tcaatcaatt tctccattaa tgttttctca      60
ctttgcaaaa tttcagtcga atatttggag atgcaatact tctcaactca gagttataca     120
ctcatcatat gcctcttttg gagggagaag aaaagagaga gtaagaagaa tgaatcgagc     180
aatggatctt tcttcaagct ctcgtcattt ggcagatttt ccctcaacaa tttggggtga     240
ccatttctc tcctacaatt ctgaaataac agaaattact cccaagaga aaatgaaca      300
tgaaatgcta aagaaatag ttcggaaaat gttggtagaa actccagata atagtacaca     360
aaaactagtc ttgattgaca caattcaaag attgggatta gcatatcatt tcaatgatga     420
gattgaaaac tccattcaaa acatctttaa tttgtctcaa aatagtgaag atgacgatga     480
acacaacctt tatgttgctg ctcttcgttt tcgacttgcg aggcaacaag gatattacat     540
gtcttcagat gtgttcaagc aattcactaa ccatgacgga aaattcaagg aaaatcatac     600
taatgatgtt caaggattat tgagtttgta tgaagcagca catatgagag tgcacgacga     660
ggagatatct acccgcttcg cgtcggcatc cggtcagtgg cagtgaaggg cgaacagttc     720
ctgattaacc acaaaccgtt ctactttact ggctttggtc gtcatgaaga tgcggacttg     780
cgtggcaaag gattcgataa cgtgctgatg gtgcacgacc acgcattaat ggactggatt     840
ggggccaact cctaccgtac ctcgcattac ccttacgctg aagagatgct cgactgggca     900
gatgaacatg gcatcgtggt gattgatgaa actgctgctg tcggctttaa cctctctta      960
ggcattggtt tcgaagcggg caacaagccg aaagaactgt acagcgaaga ggcagtcaac    1020
ggggaaactc agcaagcgca cttacaggcg attaagagc tgatagcgcg tgacaaaaac    1080
```

-continued

```
cacccaagcg tggtgatgtg gagtattgcc aacgaaccgg ataccgtcc gcaaggtgca   1140 cgggaatatt tcgcgccact ggcggaggca acgcgtaaac tcgacccgac gcgtccgatc   1200
acctgcgtca atgtaatgtt ctgcgacgct cacaccgata ccatcagcga tctctttgat   1260
gtgctgtgcc tgaaccgtta ttacggatgg tatgtccaaa gcggcgattt ggaaacggca   1320
gagaaggtac tggaaaaaga acttctggcc tggcaggaga aactgcatca gccgattatc   1380
atcaccgaat acgcgtgga tacgttagcc gggctgcact caatgtacac cgacatgtgg   1440
agtgaagagt atcagtgtgc atggctggat atgtatcacc gcgtctttga tcgcgtcagc   1500
gccgtcgtcg gtgaacaggt atggaatttc gccgattttg cgacctcgca aggcatattg   1560
cgcgttggcg gtaacaagaa agggatcttc actcgcgacc gcaaaccgaa gtcggcggct   1620
tttctgctgc aaaaacgctg gactggcatg aacttcggtg aaaaaccgca gcagggaggc   1680
aaacaatgat cctcgtcgtg cactctcata tgtgctgctt catacaaact caataatcct   1740
tgaacatcat tagtatgatt tccttgaat tttccgtcat ggttagtgaa ttgcttgaac   1800
acatctgaag acatgtaata tccttgttgc ctcgcaagtc gaaaacgaag agcagcaaca   1860
taaaggttgt gttcatcgtc atcttcacta ttttgagaca aattaaagat gttttgaatg   1920
gagttttcaa tctcatcatt gaaatgatat gctaatccca atctttgaat tgtgtcaatc   1980
aagactagtt tttgtgtact attatctgga gtttctacca acattttccg aactatttct   2040
tttagcattt catgttcatt tttctcttgg gtagtaattt ctgttatttc agaattgtag   2100
gagagaaaat ggtcaccca aattgttgag ggaaaatctg ccaaatgacg agagcttgaa   2160
gaaagatcca ttgctcgatt cattcttctt actctctctt ttcttctccc tccaaaagag   2220
gcatatgatg agtgtataac tctgagttga gaagtattgc atctccaaat attcgactga   2280
aattttgcaa agtgagaaaa cattaatgga gaaattgatt gactcatctc tctctttctc   2340
tcgccaaacg ag   2352
```

<210> SEQ ID NO 6
<211> LENGTH: 3675
<212> TYPE: DNA
<213> ORGANISM: Artificial Sequence
<220> FEATURE:
<223> OTHER INFORMATION: ddRNAiDNA construct (GW3) insert sequence

<400> SEQUENCE: 6

```
gaagcttact tttggatggt gggaatatat tttgaacctc aatatagtcg ttcaagaaga   60
atgataacac aagtagtcaa catgaactcc atcattgatg acacttatga tgcttttgca   120
acttttgatg agcttatgct tttcacggat gcgatccaaa ggtaatcttt ctataacaac   180
tgcatttgtt ctgataattt tttaagatgc tatttgaagt gttgttatag agaaatatat   240
tatgacaact tagactttgc agatgggatg taggtgccat ggattcatta ccggcatatt   300
tgagacctat ttatcaaggc cttctcgacg ttttcaatga aatggaagaa gtaatggcca   360 agaaggtaa agcagatcgc atctactatg cgaaaaaaga ggtaatcctt gattaagtta   420
cattaattac tacttaataa gttaattaag taaaccaagt tgtagggaag aatcacaatt   480
ttgaactatt agtactttt ctgttacttt tttagatgaa aaagttggtg gcagcctatt   540
ttaaggaagt tgaatggttg aatgctaact acattccaaa atgtgaggag tatatgaaaa   600 atggagttg aagttgtacc ggtagatgta tggaacaatt tgctttggtt gttatcgagg   660
aaattataac aaaagaggct tttgaatggt tgcaaatga acctttgatt cctcgagctg   720
```

```
catcaacaat ctgtagatta atggatgata ttgttgatca tgaattaagt ataacaatat    780
aatttccatt ttatataaca attagtcatc ctaattcaca aattttgtcc ctaaatacat    840
acaaaaacaa ctacaataac agaaacaaca tatccagtgt attcctatag tacgggtctg    900
ggcagagaga tgtgtatgaa gatcttaccc tatcttgtgg aggtagaaag gttgtttccc    960
gatagaccct cgactcaaaa aaacatttct caatctgatt tcgagtctag gtggcacttt   1020
tgcatgatat aataaataga catgcttgat aaattacaac ttcaatgagc acatttacat   1080
aaagtgattt atggaacttt agaaacgaac tgattaaaat ggtaaaatat tgtataatat   1140
taatgaagat attgaaatat attatgtgta ggttgaacaa caaagaggac atgttgcttc   1200
atttgttgag tactacatga aagaatatgg aacttcaaag caagaagcat atgttgagat   1260
gtggaaaaag atcacaaatg cgtggaaaga cataaataag gaactcctgc gcgctactgc   1320
agtgatatct acccgcttcg cgtcggcatc cggtcagtgg cagtgaaggg cgaacagttc   1380
ctgattaacc acaaaccgtt ctactttact ggctttggtc gtcatgaaga tgcggacttg   1440
cgtggcaaag gattcgataa cgtgctgatg gtgcacgacc acgcattaat ggactggatt   1500
ggggccaact cctaccgtac ctcgcattac ccttacgctg aagagatgct cgactgggca   1560
gatgaacatg catcgtggt gattgatgaa actgctgctg tcggctttaa cctctcttta   1620
ggcattggtt tcgaagcggg caacaagccg aaagaactgt acagcgaaga ggcagtcaac   1680
ggggaaactc agcaagcgca cttacaggcg attaaagagc tgatagcgcg tgacaaaaac   1740
cacccaagcg tggtgatgtg gagtattgcc aacgaaccgg ataccgtcc gcaaggtgca   1800 cgggaatatt tcgcgccact ggcggaggca acgcgtaaac tcgacccgac gcgtccgatc   1860
acctgcgtca atgtaatgtt ctgcgacgct cacaccgata ccatcagcga tctctttgat   1920
gtgctgtgcc tgaaccgtta ttacggatgg tatgtccaaa gcggcgattt ggaaacggca   1980
gagaaggtac tggaaaaaga acttctggcc tggcaggaga aactgcatca gccgattatc   2040
atcaccgaat acggcgtgga tacgttagcc gggctgcact caatgtacac cgacatgtgg   2100
agtgaagagt atcagtgtgc atggctggat atgtatcacc gcgtctttga tcgcgtcagc   2160
gccgtcgtcg gtgaacaggt atggaatttc gccgattttg cgacctcgca aggcatattg   2220
cgcgttggcg gtaacaagaa agggatcttc actcgcgacc gcaaaccgaa gtcggcggct   2280
tttctgctgc aaaaacgctg gactggcatg aacttcggtg aaaaaccgca gcgggaggc   2340 aaacaatgaa ttcctgcagt agcgcgcagg agttccttat ttatgtcttt ccacgcattt   2400
gtgatctttt tccacatctc aacatatgct tcttgctttg aagttccata ttctttcatg   2460
tagtactcaa caaatgaagc aacatgtcct ctttgttgtt caacctacac ataatatatt   2520
tcaatatctt cattaatatt atacaatatt ttaccatttt aatcagttcg tttctaaagt   2580
tccataaatc actttatgta aatgtgctca ttgaagttgt aatttatcaa gcatgtctat   2640
ttattatatc atgcaaaagt gccacctaga ctcgaaatca gattgagaaa tgttttttg   2700 agtcgagggt ctatcgggaa caaccttc tacctccaca agatagggta agatcttcat   2760
acacatctct ctgcccagac ccgtactata ggaatacact ggatatgttg tttctgttat   2820
tgtagttgtt tttgtatgta tttagggaca aaatttgtga attaggatga ctaattgtta   2880
tataaaatgg aaattatatt gttatactta attcatgatc aacaatatca tccattaatc   2940
tacagattgt tgatgcagct cgaggaatca aaggttcatt tgccaaccat tcaaaagcct   3000
cttttgttat aatttcctcg ataacaacca aagcaaattg ttcctacat ctaccggtac   3060 aacttacaac tccattttc atatactcct cacatttggg aatgtagtta gcattcaacc   3120
```

| | |
|---|---|
| attcaacttc cttaaaatag gctgccacca acttttttcat ctaaaaaagt aacagaaaaa | 3180 |
| gtactaatag ttcaaaattg tgattcttcc ctacaacttg gtttacttaa ttaacttatt | 3240 |
| aagtagtaat taatgtaact taatcaagga ttacctcttt tttcgcatag tagatgcgat | 3300 |
| ctgctttacc ttctttggcc attacttctt ccatttcatt gaaaacgtcg agaaggcctt | 3360 |
| gataaatagg tctcaaatat gccggtaatg aatccatggc acctacatcc catctgcaaa | 3420 |
| gtctaagttg tcataatata tttctctata acaacacttc aaatagcatc ttaaaaaatt | 3480 |
| atcagaacaa atgcagttgt tatagaaaga ttacctttgg atcgcatccg tgaaaagcat | 3540 |
| aagctcatca aaagttgcaa aagcatcata agtgtcatca atgatggagt tcatgttgac | 3600 |
| tacttgtgtt atcattcttc ttgaacgact atattgaggt tcaaaatata ttcccaccat | 3660 |
| ccaaaagtaa gcttc | 3675 |

\<210\> SEQ ID NO 7
\<211\> LENGTH: 416
\<212\> TYPE: DNA
\<213\> ORGANISM: Artificial Sequence
\<220\> FEATURE:
\<223\> OTHER INFORMATION: ddRNAiDNA construct (GW2) insert sequence

\<400\> SEQUENCE: 7

| | |
|---|---|
| cttccctctt tctttcttc ataaccctgt ctaaagggat tattatgata gtagagtctc | 60 |
| accatcgggc tcggattccg taaaagtcga acgccacca attcggctga cacagcctcg | 120 |
| tgacatttaa atctttattg gtttgtgagc agggattgga ggcgttttga cttttagggg | 180 |
| atcggatcct cgaggtgtaa aaaaactcgt aaatcctatc agatctggaa gatttctacg | 240 |
| cttctccttc tttatattcg ttttcttatg ctttttattt ttgatataac ctagaaaaag | 300 |
| gcttttata tctttgaatc cgaaattgtt tgttttagaa tattgtatat ctgattttta | 360 |
| tccctttta tatttgaatg ttctttagtc tccttttgtt tgcccaaatg ttgaat | 416 |

\<210\> SEQ ID NO 8
\<211\> LENGTH: 4531
\<212\> TYPE: DNA
\<213\> ORGANISM: Nicotiana tabacum

\<400\> SEQUENCE: 8

| | |
|---|---|
| ctcgtttggc gagagaaaga gagagatgag tcaatcaatt tctccattaa tctgttctca | 60 |
| ctttgcgaaa tttcagtcga atatttggag atgcaatact tctcaactca gagttataca | 120 |
| ctcatcatat gcctcttttg gagggagaag aaaagagaga gtaagaagaa tgaatcgagc | 180 |
| aatggatctt tcttcaagct ctcgtcattt ggcagatttt ccctcaacaa tttggggtga | 240 |
| ccattttctc tcctacaatt ctgaaataac agtaagtcac aatcccatgc ttatattcta | 300 |
| ccgtcaaact tctctataac aactccattt gttgcgatcg tttttttattg ttatagtgaa | 360 |
| gtgttgttat agagattata tattataata taacatagta atcggttccg agaaaacttg | 420 |
| attctttagt gaatgactgt tatatgggga tgttatagag aggtctgact gtgttaccta | 480 |
| aatgaataat gaagatgtta taattttatt agagatggat gaagcattta acatgaaag | 540 |
| attcaagctt taagattggt cttttatcgta cttttgaaat tatgagtttg gaatttaata | 600 |
| cttcctccgt ctcaaaaaag aatgaatctt ttactatatg gggtcaaata agattttctt | 660 |
| tggccatatt ttttgcaaat gcattttcaaa tattttgaat ttttaattgt gtgacttaca | 720 |
| atacctttta tgcagtttct aaatgtgtaa aatatatttc aaacttttaa agaatattat | 780 |

| | |
|---|---|
| gtcatcacat taaaaatatt gaacttgact ctcatgctcc gacaggttaa ataatgaaac | 840 |
| gaatggaata ttactatttt gtaaaaactt aggtaggttt tcactatata tttaataatg | 900 |
| tattcaaact cataaataat gatcaaaagg agctttgacg ggaggtcacg ggttcgagcc | 960 |
| gtggaaacaa cctcttgcaa aaatgtaagg taagactgca tacaatagac tcttgtggtc | 1020 |
| cgccccttct ccggaccccg cacatagcgg aagcttattg cactaggctg ccctttttag | 1080 |
| tgattaacat atgtggatct aggatttaaa ttttttgggt tcaaccttta aggatctgtt | 1140 |
| acaattttag tagaatgtta cacataaatt tgtgctccgt gaatgtattg agtcagatga | 1200 |
| acctggtatt atacatgcgg atacgctcct gatgctcaat ttctgcctgc aggaaattac | 1260 |
| tacccaagag aaaaatgaac atgaaatgct aaaagaaata gttcggaaaa tgttggtaga | 1320 |
| aactccagat aatagtacac aaaaactagt cttgattgac acaattcaaa gattgggatt | 1380 |
| agcatatcat ttcaatgatg agattgaaaa ctccattcaa acatctttta atttgtctca | 1440 |
| aaatagtgaa gatgacgatg aacacaacct ttatgttgct gctcttcgtt ttcgacttgc | 1500 |
| gaggcaacaa ggatattaca tgtcttcagg taccttacat ttctgccctt tcccgcacag | 1560 |
| cttcatttttt tttcgttgtt aaaagacagt tcggcgcata aaatatctca tgtatacgcc | 1620 |
| agggtcagga cgaaccgccc ccaaggggtg taaagtatgc aacttaccct aatactaaat | 1680 |
| atctcgtgta tacacagggt caggacaagt cgcacccaag gggtgtaatg tagacaactt | 1740 |
| atcctaatgc tattagtaac tgattttatg gctcgaacac ataaattata ggtcacacag | 1800 |
| taacaacttt accgttgctc aaagactcgc cttcctctttt ttttagttat cgcaccttat | 1860 |
| ttgtgcagag aatagcaagt ttcgagatct gcttctatat agaagacttc tgtattatac | 1920 |
| tttttttattt tgtccttctg cttaaaaata gtaaaaaact atagtgtgga aattgtaaat | 1980 |
| ttcttaacta gctgtgaaat caaatagtta ttataggaat attatttaag actccactta | 2040 |
| tggaaaacca ctgggttgtt gttgttattg tcaataataa cttggggtac gatttacttc | 2100 |
| tttttccatg gcttgtccac gactatattt ctattaacaa tgttgtgact atgctttctt | 2160 |
| tgagtcgagg gtctattgat aacaggctct cgatctttac aaggtaaaag taatgtctgc | 2220 |
| gtacaccact ctactccgca gactccactt gtaggatttc actgaatatt ttttgttgtt | 2280 |
| gttgttgttg taataactta gggtttaatt tcttgatgct aatgaaattc atttctttca | 2340 |
| aaatataaac atggtgttca accagatgtg ttcaagcaat tcactaacca tgacggaaaa | 2400 |
| ttcaaggaaa atcatactaa tgatgttcaa ggattattga gtttgtatga agcagcacat | 2460 |
| atgagagtgc acgacgagga aattctagaa gaagctctta tctttaccac gactcatctc | 2520 |
| gagtccgtga tcccgaattt gagcaactcg cttaaggtac aagttactga agccttaagc | 2580 |
| catcctattc gcaaagctat accaagggtg ggagcaagga aatacataca catatatgaa | 2640 |
| aacattggaa cacataatga tttactttttg aaatttgcaa agttggactt caacatgtta | 2700 |
| caaaagcttc atcgaaaaga gcttaacgag ctaacaaggt acatctacta ttcttgtcat | 2760 |
| cttcataatt atggtacaat cagacctctc tctataaaat acatcctttta taacaacagt | 2820 |
| tcactataac ggtcaagttt tctttaaaat caatgttttta tgttaccaaa ttattttgaa | 2880 |
| agaaatgtga ctattataga gaggtttgac tgtaactcgc gctaattaat aacacctaaa | 2940 |
| gtttaagtat gttaatgctg ttatgatatc tatagctggt ggaaagattt ggatcgtgca | 3000 |
| aacaaatttc catatgcaaa ggacagatta gtagaagctt acttttggac ggtgggaata | 3060 |
| tattttgaac ctcaatatag tcgttcaaga agtttggtaa caaagtagt caaaatgaac | 3120 |
| tccattattg atgacactta tgatgcttat gcaacttttg atgagcttgt gcttttcacg | 3180 |

-continued

```
gatgcgatcc aaaggtaaaa ttatatataa taaaatcttt ctataacaac gtcatttatt    3240
ctgatatttt tttaagatgc tatagtgaag tattgttata tagaaatata ttatgacaac    3300
ttagactttg cagatgggac gaaggtgcca tggatttatt accgacatat ctgagaccta    3360
tttatcaagg ccttctcgac gttttcaatg aaatggaaga agtattggcc aaagaaggta    3420
aagcagatca catctactat gcgaaaaaag aggtaatcct tgattaagtt acattaatta    3480
ctacttaata gttaattaag taaaccaagt tgtagggaag aatcgcaatt ttgaactatt    3540
agtacatttt ctgttacttt tttagatgaa aaaggtggcg gaagtctatt ttaaggaagc    3600
tgaatggttg aatgctaact acattccaaa atgcgaggag tatatgaaaa atggacttgt    3660
aagctctacc ggtccgatgt atggaataat ttctttggtt gttatggagg aaattataac    3720
aaaagaggct tttgaatggt tgacaaatga acctttgatt cttcgagctg catcaacaat    3780
ttgtagatta atggatgata tggctgatca tgaagtaagt ataacaatat aattttcatt    3840
ttatataaca atagccatcg taattcgcga attttgtccc taaatacaat acaaaaacaa    3900
ctacaataac aaaaacaaca tatccaatat attcctacag tacgggtcta ggaagagaga    3960
tgtgtacgca gatcttaccc taccttatag aggtagaaat gttgttcccg atagaccctc    4020
gactcaaaaa aagcatttct cagtctgatt tcgagtctag gtggcacttt tgcatgataa    4080
aataaataga catgcttgat aaattacaac ttcaatgatc acatttactt aaactgaatt    4140
atggaacttt agaaacggct gattaaaatg gtaaaatatt gtataataat aagaaaattg    4200
aaatatatta tgttgtaggt tgaacaacaa agaggacatg ttgcttcatt tgttgagtgc    4260
tacatgaaag aatatggagt ttcaaagcaa gaaacatatg ttgagatgcg gaaaaaaatc    4320
acaaatgcgt ggaaagatat aaataaggaa ctccttgcgcc ctactgcagt accaatgttt    4380
atcctcgaac gatctttaaa ttttttcaaga ttggccgata cattttttgaa agatgatgat    4440 ggatacacaa atcccaaatc caaagttaaa gacttgattg cttcgttgtt tgtcgaatct    4500
gtcgacatat gattatatat aacaatgcag a                                    4531
```

<210> SEQ ID NO 9
<211> LENGTH: 2251
<212> TYPE: DNA
<213> ORGANISM: Nicotiana tabacum

<400> SEQUENCE: 9

```
gctgcctttt ttttttttgg gctacaaaac tctaaagtaa aggaactaga aaactcgttt     60
ggcgagagaa agagagagat gagtcaatca atttctccat taatgttttc tcactttgca    120
aaatttcagt cgaatatttg gagatgcaat acttctcaac tcagagttat acactcatca    180
tatgcctctt ttggagggag aagaaaagag agagtaagaa gaatgaatcg agcaatggat    240
ctttcttcaa gctctcgtca tttggcagat tttccctcaa caatttgggg tgaccatttt    300
ctctcctaca attctgaaat aacagaaatt actacccaag agaaaaatga acatgaaatg    360
ctaaaagaaa tagttcggaa aatgttggta gaaactccag ataatagtac acaaaaacta    420
gtcttgattg acacaattca aagattggga ttagcatatc atttcaatga tgagattgaa    480
aactccattc aaaacatctt taatttgtct caaaatagtg aagatgacga tgaacacaac    540
ctttatgttg ctgctcttcg ttttcgactt gcgaggcaac aaggatatta catgtcttca    600
gatgtgttca agcaattcac taaccatgac ggaaaattca aggaaaatca tactaatgat    660
gttcaaggat tattgagttt gtatgaagca gcacatatga gagtgcacga cgaggaaatt    720
```

```
ctagaagaag ctcttatctt taccacgact catctcgagt ccgtgatccc gaatttgagc    780
aactcgctta aggtacaagt tactgaagcc ttaagccatc ctattcgcaa agctatacca    840
agggtgggag caaggaaata catacacata tatgaaaaca ttggaacaca taatgattta    900
cttttgaaat ttgcaaagtt ggacttcaac atgttacaaa agcttcatcg aaaagagctt    960
aacgagctaa caagctggtg aaagatttg  gatcgtgcaa acaaatttcc atatgcaaag   1020
gacagattag tagaagctta cttttggacg gtgggaatat attttgaacc tcaatatagt   1080
cgttcaagaa gtttggtaac aaaagtagtc aaaatgaact ccattattga tgacacttat   1140
gatgcttatg caacttttga tgagcttgtg cttttcacgg atgcgatcca agatgggac    1200
gaaggtgcca tggatttatt accgacatat ctgagaccta tttatcaagg ccttctcgac   1260
gttttcaatg aaatggaaga agtattggcc aaagaaggta agcagatca catttactat    1320
gcgaaaaaag agatgaaaaa ggtggcggaa gtctatttta aggaagctga atggttgaat   1380
gctaactaca ttccaaaatg cgaggagtat atgaaacatg gacttgtaag ctctaccggt   1440
ccgatgtatg gaataatttc tttggttgtt atggaggaaa ttataacaaa agaggctttt   1500
gaatggttga caaatgaacc tttgattctt cgacctgcat caacaatttg tagattaatg   1560
gatgatatgc ctgatcatga agttgaacaa caaagaggac atgttgcttc atttgttgag   1620
tgctacatga agaatatgg  agtttcaaag caagaagcat atgttgagat gcggaaaaaa   1680
atcacaaatg cgtggaaaga tataaataag gaactcttgc gccctactgc agtaccaatg   1740
tttatcctcg aacgatcttt aaattttca  agattggccg atacattttt gaaagatgat   1800
gatggataca caaatcccaa atccaaagtt aaagacttga ttgcttcgtt gtttgtcgaa   1860
tctgtcgaca tatgattata tataacaatg cagacacacc ttcaaagctg agtatttgga   1920
gcaaatatgg aagcattttg tattgtccat gtaaccctat aagtcacgtg tttgggcaat   1980
ggcaacattt actaatattt gcattatggt aggttgttta catcacacct attggggcg    2040
acccttccta aaacctgaca tgaatgtgtg atgctttgtg cacctggcgg ctcattttta   2100
ctatttcact gttacaactt atttggacgg ttgttaacct attgaatcat gtagtattgt   2160
tacttaaata caatgtttat tttaattatt acttaaattt tattctatca tatcgttaaa   2220
tccatcatta cgtaacaaaa aaaaaaaaaa a                                  2251
```

<210> SEQ ID NO 10
<211> LENGTH: 598
<212> TYPE: PRT
<213> ORGANISM: Nicotiana tabacum

<400> SEQUENCE: 10

```
Met Ser Gln Ser Ile Ser Pro Leu Met Phe Ser His Phe Ala Lys Phe
1               5                   10                  15

Gln Ser Asn Ile Trp Arg Cys Asn Thr Ser Gln Leu Arg Val Ile His
            20                  25                  30

Ser Ser Tyr Ala Ser Phe Gly Gly Arg Lys Glu Arg Val Arg Arg
        35                  40                  45

Met Asn Arg Ala Met Asp Leu Ser Ser Ser Arg His Leu Ala Asp
    50                  55                  60

Phe Pro Ser Thr Ile Trp Gly Asp His Phe Leu Ser Tyr Asn Ser Glu
65                  70                  75                  80

Ile Thr Glu Ile Thr Thr Gln Glu Lys Asn Glu His Glu Met Leu Lys
                85                  90                  95

Glu Ile Val Arg Lys Met Leu Val Glu Thr Pro Asp Asn Ser Thr Gln
```

-continued

```
                100                 105                 110
Lys Leu Val Leu Ile Asp Thr Ile Gln Arg Leu Gly Leu Ala Tyr His
            115                 120                 125

Phe Asn Asp Glu Ile Glu Asn Ser Ile Gln Asn Ile Phe Asn Leu Ser
        130                 135                 140

Gln Asn Ser Glu Asp Asp Glu His Asn Leu Tyr Val Ala Ala Leu
145                 150                 155                 160

Arg Phe Arg Leu Ala Arg Gln Gln Gly Tyr Tyr Met Ser Ser Asp Val
                165                 170                 175

Phe Lys Gln Phe Thr Asn His Asp Gly Lys Phe Lys Glu Asn His Thr
            180                 185                 190

Asn Asp Val Gln Gly Leu Leu Ser Leu Tyr Glu Ala Ala His Met Arg
        195                 200                 205

Val His Asp Glu Glu Ile Leu Glu Glu Ala Leu Ile Phe Thr Thr Thr
    210                 215                 220

His Leu Glu Ser Val Ile Pro Asn Leu Ser Asn Ser Leu Lys Val Gln
225                 230                 235                 240

Val Thr Glu Ala Leu Ser His Pro Ile Arg Lys Ala Ile Pro Arg Val
                245                 250                 255

Gly Ala Arg Lys Tyr Ile His Ile Tyr Glu Asn Ile Gly Thr His Asn
            260                 265                 270

Asp Leu Leu Leu Lys Phe Ala Lys Leu Asp Phe Asn Met Leu Gln Lys
        275                 280                 285

Leu His Arg Lys Glu Leu Asn Glu Leu Thr Ser Trp Trp Lys Asp Leu
    290                 295                 300

Asp Arg Ala Asn Lys Phe Pro Tyr Ala Lys Asp Arg Leu Val Glu Ala
305                 310                 315                 320

Tyr Phe Trp Thr Val Gly Ile Tyr Phe Glu Pro Gln Tyr Ser Arg Ser
                325                 330                 335

Arg Ser Leu Val Thr Lys Val Val Lys Met Asn Ser Ile Ile Asp Asp
            340                 345                 350

Thr Tyr Asp Ala Tyr Ala Thr Phe Asp Glu Leu Val Leu Phe Thr Asp
        355                 360                 365

Ala Ile Gln Arg Trp Asp Glu Gly Ala Met Asp Leu Leu Pro Thr Tyr
    370                 375                 380

Leu Arg Pro Ile Tyr Gln Gly Leu Leu Asp Val Phe Asn Glu Met Glu
385                 390                 395                 400

Glu Val Leu Ala Lys Glu Gly Lys Ala Asp His Ile Tyr Tyr Ala Lys
                405                 410                 415

Lys Glu Met Lys Lys Val Ala Glu Val Tyr Phe Lys Glu Ala Glu Trp
            420                 425                 430

Leu Asn Ala Asn Tyr Ile Pro Lys Cys Glu Glu Tyr Met Lys His Gly
        435                 440                 445

Leu Val Ser Ser Thr Gly Pro Met Tyr Gly Ile Ile Ser Leu Val Val
    450                 455                 460

Met Glu Glu Ile Ile Thr Lys Glu Ala Phe Glu Trp Leu Thr Asn Glu
465                 470                 475                 480

Pro Leu Ile Leu Arg Pro Ala Ser Thr Ile Cys Arg Leu Met Asp Asp
                485                 490                 495

Met Ala Asp His Glu Val Glu Gln Gln Arg Gly His Val Ala Ser Phe
            500                 505                 510

Val Glu Cys Tyr Met Lys Glu Tyr Gly Val Ser Lys Gln Glu Ala Tyr
        515                 520                 525
```

```
Val Glu Met Arg Lys Lys Ile Thr Asn Ala Trp Lys Asp Ile Asn Lys
            530                 535                 540

Glu Leu Leu Arg Pro Thr Ala Val Pro Met Phe Ile Leu Glu Arg Ser
545                 550                 555                 560

Leu Asn Phe Ser Arg Leu Ala Asp Thr Phe Leu Lys Asp Asp Gly
                565                 570                 575

Tyr Thr Asn Pro Lys Ser Lys Val Lys Asp Leu Ile Ala Ser Leu Phe
            580                 585                 590

Val Glu Ser Val Asp Ile
            595

<210> SEQ ID NO 11
<211> LENGTH: 416
<212> TYPE: DNA
<213> ORGANISM: Artificial Sequence
<220> FEATURE:
<223> OTHER INFORMATION: ddRNAiDNA construct (GW5) insert sequence

<400> SEQUENCE: 11
cttccctctt ctctttcttc ataaccctgt ctaaagggat tattatgata gtagagtctc      60
accatcgggc tcggattcga agaaatcatc caccgctcca attcggctga cacagcctcg     120
tgacatttaa atctttattg gtttgtgagc agggattgga gcggtggagg atttcttagt     180
atcggatcct cgaggtgtaa aaaaactcgt aaatcctatc agatctggaa gatttctacg     240
cttctccttc tttatattcg ttttcttatg ctttttattt ttgatataac ctagaaaaag     300
gctttttata tctttgaatc cgaaattgtt tgtttagaa tattgtatat ctgattttta      360
tcccttttta tatttgaatg ttctttagtc tccttttgtt tgcccaaatg ttgaat         416
```

METHOD OF PRODUCING TOBACCO PLANTS WITH INCREASED SUCROSE ESTER CONTENT

CROSS REFERENCE TO RELATED APPLICATIONS

This application is the National Stage of International Application No. PCT/US2018/016963, filed Feb. 6, 2018, which claims priority to and benefit of U.S. application U.S. Ser. No. 62/455,850, filed Feb. 7, 2017, all of which are incorporated herein by reference in their entirety.

FIELD OF THE INVENTION

The present invention relates to improving the flavour of tobacco and particularly relates to the sucrose ester content in tobacco plants. In particular the invention relates to increasing sucrose ester content in tobacco plants. More particularly, the invention relates to methods and uses of inhibiting the activity or expression of a diterpene synthesis gene and to tobacco plants and their downstream products (e.g. propagation materials, harvested leaf, processed tobacco, tobacco products).

BACKGROUND

Plant trichomes are specialised structures comprising epidermal outgrowths which can be found on ariel surfaces of many plants. Their morphology is variable across species and even within a species, including their location on plant organs, their size and density. They are thought to provide a first line of defence against insects, pathogenic microbes and herbivores and to provide protection against the environment such as frosty and windy conditions. Trichomes can be glandular and secrete products whose principal functions may be to produce pest- or pollinator-interactive chemicals which are stored or volatilized at the plant surface. Trichomes of such plants could serve as factories for producing natural products which have economic and commercial importance. Advantageously, secreted compounds are produced only in trichome glands and accumulate outside gland cells under the surrounding cuticle. Exudate can therefore be simply and cleanly recovered by submersion of the plant in non-invasive solvent because the exudate material essentially accumulates outside of the plant. Manipulation of plant trichome secondary exudate composition has been used to enhance insect resistance (Wang et al. Nature Biotechnology 19, 371-374 (2001) which is incorporated herein by reference) and metabolic engineering of glandular trichomes has been used to enhance the quality of essential oils (Mahmoud and Croteau Proc Natl Acad Sci U S A. 2001 Jul. 17; 98(15):8915-20. Epub 2001 Jun. 26 which is incorporated herein by reference).

A number of tobacco varieties possess both high biomass and high exudate accumulation potential. For instance the experimental tobacco line T.I. 1068 can produce up to 17% of leaf dry weight as glandular-trichome exudate (Wagner, G. J 1991 Plant Physiology 96, 675-679 which is incorporated herein by reference). Approximately 72% of the trichome gland exudate is diterpenoids and approximately 24% is sucrose esters.

The richest natural source of sucrose esters appears to be tobacco plants. Sugar esters are complex mixtures of compounds due to many possible acyl groups and combinations of acyl groups which may be esterified to the sugar (sucrose or glucose). These compounds are principally responsible for the sticky texture of tobacco leaves that produce them (Kandra, L. and G. J. Wagner, Archives Biochem. Biophys. 265 (1988) 425-432 which is incorporated herein by reference). Sucrose esters are the precursors of 3-methylvaleric and 3-methylbutyric acids which are important flavour components of Turkish tobacco smoke (Kandra, L., et al. Eur. J. Biochem. 188 (1990) 385-391 which is incorporated herein by reference), furthermore 3-methyl valeric acids are said to provide a "Turkish note" to tobacco.

The T.I. 1068 trichome exudate contains mainly cembrenoid and labdanoid diterpenoids. The CBTdiols ($\alpha$ and $\beta$ positional isomers), cis-abienol, and labdenediol account for about 60, 10 and 0.6% of exudate weight respectively. The general pathway for the synthesis of major diterpene components of T.I. 1068 trichome exudate diterpenes and CBTdiols is shown in FIG. 2. The methyl-erythritol-phosphate (MEP) pathway of the chloroplast supplies geranylgeranyl pyrophosphate (GGPP) for diterpene synthesis.

Organoleptic or sensory properties of different tobacco types vary considerably and are influenced by a complexity of factors including genetic differences. Antifungal and organoleptic properties of tobacco are thought to be related to sucrose ester content. The unique aroma and flavour profile of tobacco the result of the unique flavour and aroma compounds or the precursors of these compounds that are present at certain levels in the cured leaf and may include sucrose ester content.

Turkish tobacco (sometimes referred to as Oriental tobacco) has desirable organoleptic properties; it is a highly aromatic, small-leafed variety of tobacco with a mild flavour and contains less nicotine than other tobacco varieties. It has been determined that a measurable quantity of sucrose ester survives the tobacco curing/aging processes and thus appear as integral ingredients of commercial Turkish (or Oriental) tobaccos (M. Ashraf-Khorassani,et al. Contributions to Tobacco Research Vol 21: 7; Oct. 2005 which is incorporated herein by reference). In addition, sucrose esters are precursors of aromatic carboxylic acids in Turkish tobacco smoke and are thus important flavour components of Turkish tobaccos (Arrendale, R. F., et al., J. Agric. Food Chem. 38 (1990) 75-85 which is incorporated herein by reference).

Naturally occurring sucrose esters present challenging analytical problems due to the extent of esterification and the distribution of ester functionality within the molecule. In the sucrose molecule, there are four sites for potential acyl groups (e.g. one primary, three secondary) on the glucose (GLU) ring; and another four sites (e.g. two primary, two secondary) can be found on the fructose (FRU) ring. To date, identification of the ester acid moieties has been via GC- MS (gas chromatography-mass spectrometry) and LC-MS (liquid chromatography-mass spectrometry) (see Slocombe et al. Plant Physiol. 148, 1830-1846, which is incorporated herein by reference) of either sucrose methyl/butyl esters or sucrose trimethylsilyl (TMS) derivatives. High temperature GC (gas chromatography) has been investigated with marginal success in an effort to encompass higher molecular weight carbohydrate derivatives (Karrer, R., et al., J. High Resolu. Chromatogr. 15 (1992) 585-589, which is incorporated herein by reference). Inferences concerning acyl substitution patterns on the sucrose ester from data obtained by acid hydrolysis of the ester and re-derivatization of the released carboxylic acid has been reported, but this approach can be subject to different interpretations.

SUMMARY OF THE INVENTION

It has been surprisingly found that by inhibiting the activity or expression of a diterpene synthesis gene as taught herein the distinctive flavour (and/or aroma and/or taste) characteristics such as those found in Turkish tobacco can be produced by tobacco plants with commercially desirable traits by modifying tobacco to produce tobacco with increased sucrose ester content. Thereby tobacco products with superior flavour (and/or aroma and/or taste) characteristics sought after by consumers of tobacco products can be produced.

The present inventors investigated the regulation and paths of carbon flow in specialised trichome gland cells that produce specific secondary compounds. One aim of the inventors was to optimise trichome gland diterpene metabolism to modify trichome exudate chemistry to provide alerted diterpene contents. Plant line cell lines were created which unexpectedly exhibited increased sucrose ester content in the exudate compared to their wild-type plant counterparts grown under the same conditions. The plant lines targeted the enzymes catalysing the formation of CBTol (a synthase) and terpene synthase 3-8. Terpene synthase 3-8 in some embodiments may be referred to as cis-abienol synthase.

The present inventors have surprisingly determined a method for increasing the sucrose ester content of a tobacco plant by inhibiting the activity or expression of a diterpene synthesis gene. Prior to the present invention it had not been known that inhibition of the activity or expression of a diterpene synthesis gene could be used to increase sucrose ester content, particularly whilst improving yields and other commercially desirable traits.

According to one aspect the present invention provides a method of increasing the sucrose ester content of a tobacco plant or part thereof or a tobacco cell culture, the method comprising modifying said tobacco plant or tobacco cell culture by inhibiting the activity or expression of a diterpene synthesis gene.

In another aspect there is provided the use of a diterpene synthesis gene for increasing the sucrose ester content of a tobacco plant or part thereof or a tobacco cell culture.

The present invention provides in another aspect a method for producing a tobacco plant or part thereof, a tobacco plant propagation material, a tobacco leaf, a cut harvested tobacco leaf, a processed tobacco leaf or a cut and processed tobacco leaf or a tobacco cell culture which has increased sucrose ester content, the method comprising modifying said tobacco to inhibit the activity or expression of a diterpene synthesis gene.

In another aspect there is provided a method or use according to the invention, wherein the sucrose ester content is increased in comparison to a tobacco plant or tobacco cell culture which has not been modified to inhibit the activity or expression of a diterpene synthesis gene.

In another aspect there is provided a tobacco plant or part thereof or tobacco cell culture which has been modified to achieve an increase in sucrose ester content in comparison to an unmodified plant or an unmodified tobacco cell culture, wherein the modification is the inhibition of the activity or expression of a diterpene synthesis gene.

In one aspect there is provided a tobacco plant propagation material (e.g. a plant seed) obtainable from a tobacco plant or a tobacco cell culture according to the invention.

The invention provides in another aspect a method or use, a tobacco plant or a tobacco plant propagation material, or a tobacco cell culture wherein the diterpene synthesis gene is cyclase 2 gene (CYC2), CBTol cyclase or terpene synthase 3-8.

The invention provides in one aspect a method or use, a tobacco plant or a tobacco plant propagation material, wherein the diterpene synthesis gene is cyclase 2 gene (CYC2).

The invention provides in one aspect a method or use, a tobacco plant or a tobacco plant propagation material, wherein the diterpene synthesis gene is CBTol cyclase.

The invention provides in one aspect a method or use, a tobacco plant or a tobacco plant propagation material, wherein the diterpene synthesis gene is terpene synthase 3-8.

The invention provides in another aspect a method or use, a tobacco plant or part thereof or a tobacco plant propagation material or a tobacco cell culture according to the invention wherein expression of a diterpene synthesis gene is inhibited using RNA interference (RNAi).

In one aspect there is provided a method, use, tobacco plant or tobacco plant propagation material, or a tobacco cell culture wherein cyclase 2 gene (CYC2) expression is inhibited using an ddRNAi DNA construct comprising at least part of exon1, at least part of exon 2 and at least part of exon 3 of the cyclase 2 gene (CYC2) gene.

In one aspect there is provided a method, use, tobacco plant or tobacco plant propagation material, or a tobacco cell culture wherein cyclase 2 gene (CYC2) expression is inhibited using a dsRNA which is processed by endogenous pathways in the cell into single stranded short interfering RNA (siRNA) which directs an RNA-induced silencing complex (RISC) to bind to mRNA corresponding to the at least part of exon1, at least part of exon 2 and at least part of exon 3 of the cyclase 2 gene (CYC2). In one aspect the single stranded siRNA produces an antisense (or guide) strand which has a complementary sequence to mRNA corresponding to the at least part of exon1, at least part of exon 2 and at least part of exon 3 of the cyclase 2 gene (CYC2).

In one aspect there is provided a method, use, tobacco plant or tobacco plant propagation material or a tobacco cell culture according to the invention, wherein CBTol cyclase gene expression is inhibited using a ddRNAi DNA construct comprising at least part of exon 4, intron 4, exon 5, intron 5, exon 6, intron 6 and at least part of exon 7 of the CBTol cyclase gene.

In another aspect there is provided a method, use, tobacco plant or tobacco plant propagation material or a tobacco cell culture according to the invention, wherein CBTol cyclase gene expression is inhibited using a dsRNA which is processed by endogenous pathways in the cell into single stranded siRNA which directs an RNA-induced silencing complex (RISC) to bind to mRNA corresponding to the at least part of exon 4, intron 4, exon 5, intron 5, exon 6, intron 6 and at least part of exon 7 of the CBTol cyclase. In one aspect the single stranded siRNA produces an antisense (or guide) strand which has a complementary sequence to mRNA corresponding to the at least part of exon 4, exon 5, exon 6 and at least part of exon 7 of the CBTol cyclase gene.

In one aspect there is provided a method, use, tobacco plant or tobacco plant propagation material or a tobacco cell culture according to the invention, wherein terpene synthase 3-8 gene expression is inhibited using a ddRNAi DNA construct comprising a sequence which corresponds to at least nucleotides 1497 to 1517 of SEQ ID No. 3.

In another aspect there is provided a method, use, tobacco plant or tobacco plant propagation material or a tobacco cell culture according to the invention, wherein terpene synthase 3-8 gene expression is inhibited using an artificial micro RNAi (amiRNAi) comprising a sequence which corresponds to at least nucleotides 1497 to 1517 of SEQ ID No. 3.

In one aspect there is provided a method, use, tobacco plant or tobacco plant propagation material or a tobacco cell culture according to the invention, wherein terpene synthase 3-8 gene expression is inhibited using a ddRNAi DNA construct comprising a sequence which corresponds to at least nucleotides 884 to 904 of SEQ ID No. 3.

In another aspect there is provided a method, use, tobacco plant or tobacco plant propagation material or a tobacco cell culture according to the invention, wherein terpene synthase 3-8 gene expression is inhibited using an artificial micro RNAi (amiRNAi) comprising a sequence which corresponds to at least nucleotides 884 to 904 of SEQ ID No. 3.

In one aspect there is provided a method or use of the invention, a tobacco plant or part thereof of the invention, or a tobacco plant propagation material or a tobacco cell culture of the invention, wherein the sucrose ester content of the tobacco plant is at least 2-fold (suitably at least 3-fold) higher in the modified tobacco plant or tobacco cell culture in comparison to a tobacco plant or tobacco cell culture which has not been modified to inhibit the activity or expression of a diterpene synthesis gene.

In one aspect there is provided the use of a tobacco plant or part thereof of the invention to breed a tobacco plant.

In another aspect the invention provides the use of a tobacco plant or part thereof or a tobacco cell culture of the invention for production of a tobacco industry product.

In another aspect there is provided the use of a tobacco plant or part thereof of the invention to grow a crop.

In one aspect the invention provides cured tobacco material made from a plant or a part thereof according the invention or an extract thereof or a tobacco cell culture according the invention.

In another aspect there is provided a tobacco blend comprising said cured tobacco material of according to the invention.

In one aspect there is provided the use of a tobacco plant or part thereof of the invention to produce a tobacco leaf (e.g. a processed (preferably cured) tobacco leaf).

In another aspect there is provided a harvested leaf of a tobacco plant of the invention or obtainable from a tobacco plant propagated from a propagation material of the invention or obtainable from a tobacco plant obtained by a use of the invention.

In one aspect there is provided a harvested leaf of a tobacco plant of the invention wherein the harvested leaf of a tobacco plant is a cut harvested leaf.

The invention provides in another aspect a processed tobacco leaf (preferably a non-viable processed tobacco leaf):
i) obtainable from a tobacco plant obtainable from a use of the invention;
ii) obtainable by processing a tobacco plant of the invention;
iii) obtainable from a tobacco plant propagated from a tobacco plant propagation material of the invention; or
iv) obtainable by processing a harvested leaf of a tobacco plant of the invention.

In one aspect there is provided a processed tobacco leaf of the invention wherein the tobacco is processed by curing, fermenting, pasteurising or a combination thereof.

In one aspect there is provided a processed tobacco leaf of the invention wherein the processed tobacco leaf is a cut processed tobacco leaf.

The invention provides in another aspect a tobacco industry product prepared from:
i) a tobacco plant of the invention or a part thereof or a tobacco cell culture of the invention;
ii) a tobacco plant or part thereof propagated from a tobacco plant propagation material of the invention;
iii) a harvested leaf of a tobacco plant of the invention;
iv) a processed tobacco leaf of the invention.

In one aspect there is provided a tobacco industry product of the invention, wherein the tobacco product is a smoking article.

In another aspect there is provided a tobacco industry product of the invention, wherein the tobacco product is a smokeless tobacco product.

In one aspect there is provided a tobacco industry product of the invention, wherein the tobacco product is a tobacco heating device such as an aerosol-generating device.

In one aspect, there is provided a smoking article, smokeless tobacco product or tobacco heating device comprising a plant or a part thereof according to the invention or an extract (e.g. a tobacco extract) thereof or a tobacco cell culture according to the invention; or a cured tobacco material according to the invention; or a tobacco blend according to the invention.

In one aspect there is provided a method, a tobacco leaf, a tobacco plant, a tobacco plant propagation material, a harvested leaf, a processed tobacco, a tobacco product, a use or a combination thereof substantially as described herein with reference to the description and drawings.

BRIEF DESCRIPTION OF THE DRAWINGS

Embodiments of the invention will now be described, by way of example only, with reference to accompanying drawings, in which.

Figure 1:
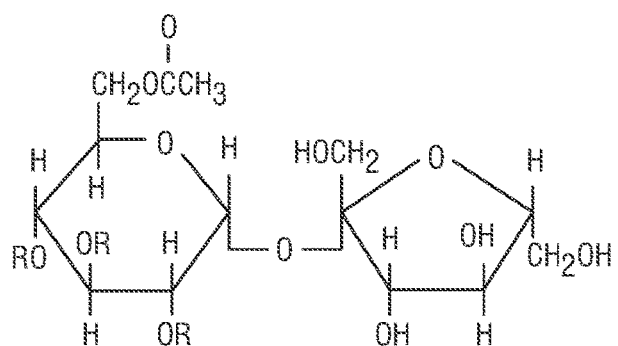
FIG. 1. shows the general structure of a sucrose ester.
Figure 2:
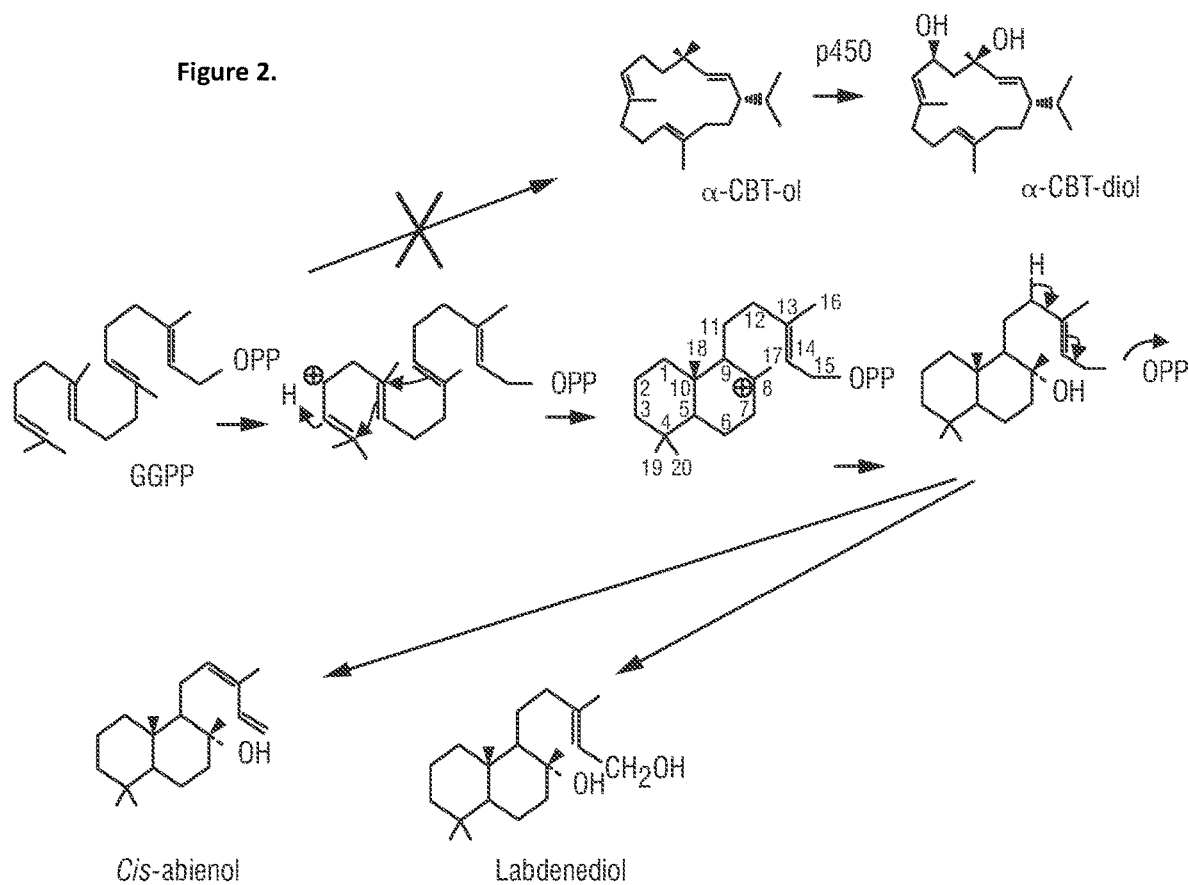
FIG. 2. shows a schematic of the diterpene synthesis pathway in plastids.

The sucrose ester content is presented as the percentage of total major exudate compounds.

FIG. 6. shows a graph demonstrating cis-abienol enrichment in line GW-3 versus the control. The cis-abienol content is presented as the percentage of total major exudate compounds.

FIG. 7A-C. shows SEQ ID No. 1 as described below.
FIG. 8. shows SEQ ID No. 2 as described below.
FIG. 9. shows SEQ ID No. 3 as described below.
FIG. 10. shows SEQ ID No. 4 as described below.
FIG. 11. shows SEQ ID No. 5 as described below.
FIG. 12. shows SEQ ID No. 6 as described below.
FIG. 13. shows SEQ ID No. 7 as described below.
FIG. 14A-D. shows SEQ ID No. 8 as described below.
FIG. 15A-C. shows SEQ ID No. 9 as described below.
FIG. 16. shows SEQ ID No. 10 as described below.
FIG. 17. shows SEQ ID No. 11 as described below.

SEQUENCE LISTING

A summary of sequence identifiers used throughout the subject specification and the corresponding sequence listing is provided wherein:

SEQ ID No. 1 corresponds to the nucleotide sequence encoding the CBTol cyclase gene. This nucleotide sequence in annotated in Genbank: AY049090.

SEQ ID No. 2 corresponds to the amino acid sequence of the polypeptide CBTol cyclase.

SEQ ID No. 3 corresponds to the cDNA gene sequence i.e. the coding sequence of the terpene synthase 3-8 gene from *Nicotiana tabacum*. The full length cDNA gene sequence is annotated in Genbank: AY528645.

SEQ ID No. 4 corresponds to the amino acid sequence of the polypeptide terpene synthase 3-8 from *Nicotiana tabacum*.

SEQ ID No. 5 comprises in order a 5'-sense fragment from the 54th to the 716th nucleotide from the sequence AF401234 (which is the complete coding sequence of CYC2 mRNA and corresponds to the nucleotide numbering in SEQ ID No. 9); a partial GUS A fragment as a hairpin loop (from 787th to the 1812th nucleotide); and the reverse complement of the sense fragment- 3'. In the figure, the underlined sequence corresponds to the GUS A fragment (AF502128) from the 787th to the 1812th nucleotide. The 54 to 716 nucleotide sequence from CYC2 mRNA (AF401234 corresponding to SEQ ID No. 9) in sense orientation corresponds to the following genomic sequences from AY495694 (AY495694 is the genomic sequence of the CYC2 gene and corresponds to SEQ ID No. 8): nucleotides 1 to 25, 1st exon (nucleotides 26 to 271), 2nd exon (nucleotides 1253 to 1529) and first 115 nucleotides of the 3rd exon (nucleotides 2366 to 2480) where the nucleotide numbering corresponds to the numbering in SEQ ID No. 8. SEQ ID No. 5 encodes a dsRNA and is used in a ddRNAi DNA construct (sometimes referred to herein as GW1) to produce a dsRNA.

SEQ ID No. 6 comprises a sequence from the CBTol cyclase gene *Nicotiana tabacum* comprising a partial sequence of exon4, intron4, exon 5, intron 5, exon 6, intron 6 and partial exon 7 sense and antisense orientation, separated by a GUS spacer. The elements of the partial gene are shown in the figure in the following order: *N. tabacum* cyclase gene (AY049090), partial exon 4—from nucleotide 2854 to nucleotide 4175, forward orientation, partial exon 4, intron 4 (in bold), exon 5, intron 5 (in bold), exon 6, intron 6 (in bold), partial exon 7 (corresponding to nucleotides 2854 to 4175 of SEQ ID No. 1); followed by the GUS loop—Partial GUS A gene (Genbank accession no. AF502128)—from 786 to 1816 (which is underlined); followed by the same, sequence of *N. tabacum* cyclase gene (AY049090) but in reverse complement (the reverse complement is shown in shading). This sequence encodes a dsRNA and is used in a ddRNAi DNA construct (sometimes referred to herein as GW3) to produce a dsRNA.

SEQ ID No. 7 comprises a 21 nucleotide sequence from the terpene synthase 3-8 gene from *Nicotiana tabacum* and sequences which match with an *Arabidopsis* miRNA168 sequence. The sequence corresponds with the *Arabidopsis* miRNA168a, the first and second italic sequences correspond to a 21 nucleotide sequences from the terpene synthase 3-8 gene AY528645 (from 1497 to 1517nt). The first italic sequence (highlighted) is in reverse complement orientation. The second italic sequence (underlined) is in forward orientation, and has three modifications (in bold). The sequence encodes an amiRNAi and is used in a ddRNAi DNA construct (sometimes referred to herein as GW2) to produce an amiRNAi.

SEQ ID No. 8 corresponds to the genomic sequence of the cyclase 2 gene (CYC2). This nucleotide sequence in annotated in Genbank: AY495694.

SEQ ID No. 9 corresponds to the complete coding sequence of mRNA of the cyclase 2 gene (CYC2) annotated in Genbank: (AF401234).

SEQ ID No. 10 corresponds to the amino acid sequence of the polypeptide encoded by the cyclase 2 gene (CYC2) SEQ ID No. 9.

SEQ ID No. 11 comprises a 21 nucleotide sequence from the terpene synthase 3-8 gene from *Nicotiana tabacum* and sequences which match with an *Arabidopsis* miRNA168a sequence. The sequence corresponds with the *Arabidopsis* miRNA168a sequence, the first and second italic sequences correspond to a 21 nucleotide sequences from the terpene synthase 3-8 gene AY528645 (from 884 to 904 nt) in reverse complement. The first italic sequence (highlighted) is in reverse complement orientation. The second italic sequence (underlined) is in forward orientation, and has modifications (in bold). The sequence encodes an amiRNAi and is used in a ddRNAi DNA construct (sometimes referred to herein as GW5) to produce an amiRNAi.

DETAILED DESCRIPTION

For the first time the present inventors have shown that by inhibiting the activity or expression of a diterpene synthesis gene in tobacco, the sucrose ester content of the tobacco plant can be increased. Without wishing to be bound by theory, the inhibition of a diterpene synthesis gene is believed to result in reduced carbon utilization to make diterpenes and thus enhance sucrose ester production.

In one embodiment the present invention provides a method of increasing the sucrose ester content of a tobacco plant, the method comprising modifying said tobacco plant by inhibiting the activity or expression of a diterpene synthesis gene.

Suitably, the diterpene synthesis gene for use in the invention may be the cyclase 2 gene (CYC2). Suitably, the diterpene synthesis gene for use in the invention may be the CBTol cyclase gene. Suitably, the diterpene synthesis gene may for use in the invention be the terpene synthase 3-8 gene.

The term "increasing" is used herein to mean that the concentration and/or total content of sucrose ester in the product of the present invention (e.g. plant, part thereof (e.g. leaf), processed leaf or tobacco product) is higher compared with a comparable product which has not been modified in accordance with the present invention.

The term "a comparable product" as defined herein would be one derived from a tobacco plant which had not been modified according to the present invention, but in which all other relevant features were the same (e.g. plant species, growing conditions, method of processing tobacco, etc.). The comparable product according to the present invention may mean a tobacco plant or a part thereof, such as a tobacco leaf, a harvested leaf, a cut harvested leaf, a processed tobacco leaf or tobacco plant propagation material, or a tobacco product or combinations thereof obtainable or obtained from a tobacco plant which has not been modified to inhibit the activity or expression of a diterpene synthesis gene. Comparable products may also be known as controls. In one embodiment a comparable product is one which does not comprise a diterpene synthesis gene the activity or expression of which has been inhibited.

The term "unmodified plant" as defined herein would be a tobacco plant which had not been modified according to the present invention, to inhibit the activity or expression of a diterpene synthesis gene and in which all other relevant features were the same (e.g. plant species, growing conditions, method of processing tobacco, etc.). In one embodiment an unmodified plant is one which does not comprise a diterpene synthesis gene the activity or expression of which has been inhibited.

In a further aspect, the sucrose ester content is measured from green leaves. In a further aspect, the sucrose ester content is measured from cured leaves, e.g. air-cured, flue-cured, fire-cured or sun-cured leaves. In a further aspect, the sucrose ester content is measured from flue-cured leaves. In a further aspect, the sucrose ester content is measured from air-cured leaves.

The term "sucrose ester content" is used herein to mean the concentration and/or total content of the entire group of compounds classified as sucrose esters. Sucrose esters typically present in tobacco can be represented by the formula shown in FIG. 1.

Any method known in the art for determining the concentration and/or total content of sucrose esters may be used. One preferred method for analysing sucrose esters (SE) involves the analysis of acyl groups released from sucrose by saponification, followed by analysis of their butyl-esters by GC-MS. Analysis by this method provides strong quantitation of sucrose ester amount. An alternative method involves the analysis of sucrose esters by measuring sucrose per $\mu g/cm^2$ leaf surface. The determination of sucrose ester content can be assessed in the tobacco leaf. Suitable methods for analysing sucrose ester content may include steps of saponification e.g. placing gum samples in 80% methanol overnight at 22° C. to saponify. Then the samples can be partitioned between hexane and water. To partition the sample, the samples may first be dried e.g. under $N_2$ then n-BuOH and $H_2SO_4$ can be added. The samples can be heated to 110° for 1 hour before pulse vortexing. Extractions can be made and the dried sample dissolved in $CHCl_3$ for transfer into another tube and dried under $N_2$. The samples can be dissolved in dimethyl formamide (DMF) and bis (trimethylsilyl) trifluoroacetamide. The samples can be derivitised e.g. at 70° before being cooled to room temperature. The derivatized samples can then be analysed by GC-MS. Eluted compounds can be identified by their retention time and by comparison of MS profiles with standards.

In one embodiment there is provided a method for producing a tobacco plant, a tobacco plant propagation material, tobacco leaf, harvested leaf, cut harvested leaf, processed tobacco leaf, cut and processed tobacco leaf, tobacco product or combinations thereof obtainable or obtained by a tobacco plant of the invention which has increased sucrose ester content, the method comprising modifying said tobacco to inhibit the activity or expression of a diterpene synthesis gene. The increased sucrose ester content may be determined by comparing the sucrose ester content in the tobacco plant, tobacco plant propagation material, tobacco leaf, harvested leaf, cut harvested leaf, processed tobacco leaf, cut and processed tobacco leaf, tobacco product or combinations thereof with a comparable product.

Suitably the sucrose ester content may be increased in a tobacco plant, e.g. a modified tobacco plant. Suitably the sucrose ester content may be increased in a tobacco leaf (e.g. a tobacco leaf from a modified tobacco plant). Suitably the sucrose ester content may be increased in a harvested leaf (e.g. a harvested tobacco leaf from a modified tobacco plant). Suitably the sucrose ester content may be increased in a cut harvested leaf (e.g. a cut harvested tobacco leaf from a modified tobacco plant). Suitably the sucrose ester content may be increased in a processed tobacco leaf (e.g. a processed tobacco leaf from a modified tobacco plant). Suitably the sucrose ester content may be increased in a cut and processed tobacco leaf (e.g. a cut and processed tobacco leaf from a modified tobacco plant). Suitably the sucrose ester content may be increased in a trichome exudate of a cured tobacco leaf (e.g. a tobacco leaf from a modified tobacco plant). Suitably the sucrose ester content may be increased in a extract of a green tobacco leaf (e.g. a tobacco leaf from a modified tobacco plant). Suitably the sucrose ester content may be increased in a tobacco product (e.g. a tobacco product produced from a modified tobacco plant or part thereof). Suitably the sucrose ester content may be increased in any one of the above products or combinations thereof.

In one embodiment the sucrose ester content is increased in a trichome exudate of a cured tobacco leaf (e.g. a tobacco leaf from a modified tobacco plant).

In one embodiment the sucrose ester content is increased in an extract of a green tobacco leaf (e.g. a tobacco leaf from a modified tobacco plant).

In one embodiment the sucrose ester content of a tobacco plant or part thereof may be increased by at least 2, 3, 4, 5, 6, 7, 8, 9, 10, fold when compared to the sucrose ester content of a tobacco plant or part thereof, respectively, which has not been modified to inhibit the activity or expression of a diterpene synthesis gene which has been grown under similar growth conditions. Suitably the sucrose ester content may be increased by about 2 fold to about 10 fold, preferably about 3 fold to about 10 fold, suitably about 3 fold to about 5 fold.

In one embodiment the method or use results in increased sucrose ester content in comparison to a tobacco plant or part thereof which has not been modified to inhibit the activity or expression of a diterpene synthesis gene and more particularly as compared to, or relative to, the expression by a tobacco plant in the absence of the introduced inhibition.

In an embodiment a tobacco plant or part thereof has been modified to achieve an increase in sucrose ester content in comparison to a tobacco plant or part thereof, respectively, which has not been modified to inhibit the activity or expression of the diterpene synthesis gene.

The term "modifying" or "modified" as used herein means a tobacco plant that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis and modern population analysis approaches. In one embodiment the term "modifying" refers to selecting a natural variant which has an inhibited diterpene synthesis gene and breeding that trait or gene into a second plant which has commercially desirable traits.

The term "inhibiting" (e.g. inhibiting the activity or expression of a diterpene synthesis gene) as used herein means that the activity or expression of the diterpene synthesis gene is lower or decreased compared with the gene activity or expression of the gene in a comparable product or the amount or activity of a protein produced by the diterpene synthesis gene is lower.

In one embodiment the term "inhibiting" (e.g. inhibiting the activity or expression of a diterpene synthesis gene) as used herein means that the activity or expression of the diterpene synthesis gene is lower compared with the gene activity or expression of the gene in a comparable product.

The "activity" or "function" of a diterpene synthesis gene relates to its ability to function in the biosynthesis of diterpenes. The activity or function of a diterpene synthesis gene can be determined by measuring the direct products of diterpene synthesis i.e. by measuring the level of diterpenes. Exudate components may be measured by washing leaves or leaf discs with acetonitrile. The washes are concentrated via rotor evaporation to yield oily residue. The residue can then be derivatized to form tri-methyl silyl (TMS) esters (as described by Severson et al. 1985. J. Agric. Food Chem. 33, 870-875 which is incorporated herein by reference). The TMS derivatives can then be separated and analysed by gas chromatography coupled to mass spectrometry (GC-MS). Eluted compounds can be identified by their retention time and by comparison of MS profiles with standards as described in Wang et al. 2001 (supra, which is incorporated herein by reference). In one embodiment the direct product of the diterpene synthesis gene may be cis-abienol, α-CBT-ols, β-CBT-ols, α-CBT-diols, β-CBT-diols or Labdenediol.

The activity of specific diterpene synthesis genes can be measured by measuring transcription of the gene. Methods for measuring transcription are well known in the art and include, amongst others, northern blot, RNA-Seq, in situ hybridization, DNA microarrays and RT-PCR. Alternatively, the activity of a gene may be measured indirectly by measuring the level of the gene product for example the protein encoded by said gene.

The activity or expression of a gene may refer to the level of transcription, translation i.e. protein expression, or the activity of the protein encoded by the diterpene synthesis gene. According to one aspect of the invention, gene expression may be inhibited by inhibiting transcription and/or translation. In one embodiment the activity or expression of a gene may refer to the level of transcription, i.e. the amount of mRNA produced, or translation i.e. the level or amount of protein produced.

Inhibiting, Reducing or Preventing Expression and/or Function

Any method known in the art for inhibiting or reducing or preventing the expression or function of a diterpene synthesis gene may be used in the present method.

By way of example, the present method may comprise:
    providing a mutation in a nucleic acid sequence which encodes a protein comprising the amino acid sequence shown as SEQ ID No. 2, SEQ ID No. 4 or SEQ ID No. 11 or an amino acid sequence which has at least 70% sequence identity thereto;
    providing a mutation in a regulatory region (e.g. a promoter and an enhancer) which contributes to controlling the expression of a protein comprising the amino acid sequence shown as SEQ ID No. 2, SEQ ID No. 4 or SEQ ID No. 11 or an amino acid sequence which has at least 70% sequence identity thereto;
    providing an antisense RNA, siRNA or miRNA which reduces the level of nucleic acid sequence encoding a protein comprising the amino acid sequence shown as SEQ ID No. 2, SEQ ID No. 4 or SEQ ID No. 11, or an amino acid sequence which has at least 70% sequence identity thereto.

Each of the above approaches results in the reduction or prevention of expression or function of a protein comprising the amino acid sequence shown as SEQ ID No. 2, SEQ ID No. 4 or SEQ ID No. 11 or an amino acid sequence which has at least 70% sequence identity thereto.

As used herein, the term "mutation" encompasses a natural genetic variant or an engineered variant. In particular, the term "mutation" refers to a variation in the nucleotide sequence encoding the amino acid sequence or in the amino acid sequence compared to the sequence shown as SEQ ID No. 2, SEQ ID No. 4 or SEQ ID No. 11 or an amino acid sequence which has at least 70% sequence identity thereto which reduces the expression or function of the protein.

In a preferred embodiment, each copy of a nucleic acid sequence encoding a protein comprising a sequence shown as SEQ ID No. 2, SEQ ID No. 4 or SEQ ID No. 11 or a sequence which has at least 70% sequence identity thereto which is present in the plant is mutated as defined herein (e.g. each genomic copy of a gene encoding said protein in a plant is mutated). For example, each copy of the gene in the allotetraploid genome of *N. tabacum* may be mutated.

In a preferred embodiment the plant or plant cell according to the present invention is homozygous for the mutation.

In one embodiment preferably the plant or plant cell according to the present invention expresses only the mutated nucleic acid. In other words, in some embodiments no endogenous (or endogenous and functional protein) is present in the plant according to the present invention. In other words, if any endogenous protein is present it is preferably in an inactive and/or truncated form.

In one embodiment the present method may comprise providing a mutation in the sequence shown as SEQ ID No. 1, SEQ ID No. 3 or SEQ ID No. 8 or a nucleic acid sequence which has at least 70% identity thereto.

The mutation may alter the plant genome such that a nucleic acid sequence encoding a protein comprising the amino acid sequence shown as SEQ ID No. 2, SEQ ID No. 4 or SEQ ID No. 11 or an amino acid sequence which has at least 70% sequence identity thereto is completely or partially deleted or otherwise made non-functional.

The mutation may interrupt the nucleic acid sequence which encodes a protein comprising the amino acid sequence shown as SEQ ID No. 2, SEQ ID No. 4 or SEQ ID No. 11 or an amino acid sequence which has at least 70% sequence identity thereto.

The interruption may cause the nucleic acid sequence to not be transcribed and/or translated. The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutant or a non-tolerated amino acid substitution in the open reading frame. A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutant inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein. Any method known in the art for providing a mutation in a nucleic acid sequence may be used in the present method. For example, homologous recombination may be used, in which a vector is created in which the relevant nucleic acid sequence(s) are mutated and used to transform plants or plant cells. Recombinant plants or plant cells expressing the mutated sequence may then be selected.

In one embodiment the mutation introduces a non-tolerated amino acid substitution in a protein comprising an amino acid sequence shown as SEQ ID No. 2, SEQ ID No. 4 or SEQ ID No. 11 or a sequence which has at least 70% sequence identity thereto.

In one embodiment the mutation reduces the activity of the protein in relation to a protein shown as SEQ ID No. 2, SEQ ID No. 4 or SEQ ID No. 11 or a sequence which has at least 70% sequence identity thereto.

In one embodiment the mutation does not alter the level or expression but reduces the activity of the protein in relation to a protein shown as SEQ ID No. 2, SEQ ID No. 4 or SEQ ID No. 11 or a sequence which has at least 70% sequence identity thereto.

The nucleic acid sequence may be wholly or partially deleted. The deletion may be continuous, or may comprise a plurality of sections of sequence. The deletion preferably removes a sufficient amount of nucleotide sequence such that the nucleic acid sequence no longer encodes a functional protein. The deletion may, for example, remove at least 50, 60, 70, 80 or 90% of the coding portion of the nucleic acid sequence.

The deletion may remove one or more domains of the diterpene synthesis gene. The deletion may be total, in which case 100% of the coding portion of the nucleic acid sequence is absent, when compared to the corresponding genome comparable unmodified plant.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

In some embodiments the activity or expression of a diterpene synthesis gene may be inhibited or reduced by at least about 10% 20% 30%, or 40%, suitably at least about 50%, 60%, 70%, more suitably at least about 80%, 90%, 95% or 100% when compared to the activity or expression of a diterpene synthesis gene in a tobacco plant which has not been modified in accordance with the present invention.

In a preferred embodiment the diterpene synthesis gene may have substantially no activity or expression, which means that the plant may comprise less than about 1% (suitably less than about 0.1%) activity or expression, preferably when compared to a plant which has not been modified to inhibit the activity or expression of a diterpene synthesis gene.

The diterpene synthesis gene as used herein refers to any gene which is involved in the production of diterpenes. Suitably the diterpene synthesis gene is a plant diterpene synthesis gene. Such genes may directly be part of the biosynthetic pathway which produces diterpenes or may feed into the biosynthetic pathway indirectly for example by providing metabolic precursors. Diterpene synthesis genes may be involved in specialized (secondary) metabolism or general (primary) metabolism. In one embodiment the diterpene synthesis gene used herein refers to a gene which is involved in specialized (secondary) metabolism. Suitably, the diterpene synthesis gene as used in the present invention may be selected from a group of diterpene synthesis genes consisting of cyclase 2 gene (CYC2), CBTol cyclase and terpene synthase 3-8 or homologous to any one of cyclase 2 gene (CYC2), CBTol cyclase, or terpene synthase 3-8. Suitably, the diterpene synthesis gene as used in the present invention may be selected from a group of diterpene synthesis genes consisting of cyclase 2 gene (CYC2), CBTol cyclase and terpene synthase 3-8.

Suitably the diterpene synthesis gene as used in the present invention is cyclase 2 gene (CYC2). Suitably the diterpene synthesis gene as used in the present invention is CBTol cyclase. Suitably the diterpene synthesis gene as used in the present invention is terpene synthase 3-8.

In one embodiment the diterpene synthesis gene referred to herein is cyclase 2 gene (CYC2) and may be encoded by a polynucleotide sequence comprising:
i) a polynucleotide sequence shown herein as SEQ ID No. 8 or SEQ ID No. 9, or
ii) a functional fragment of the polynucleotide sequence shown in i) which functional fragment encodes a diterpene synthesis gene, or
iii) a polynucleotide which encodes a polypeptide comprising the amino acid sequence shown herein as SEQ ID No. 10, or
iv) a polynucleotide sequence which can hybridize to the polynucleotide taught in i), ii) or iii) above under high stringency conditions, or
v) a polynucleotide sequence which has at least 70% (preferably 85%, more preferably 90%) identity with the polynucleotide shown in i), ii) or iii) above, or
vi) a polynucleotide sequence which differs from polynucleotide shown in i), ii) or iii) due to degeneracy of the genetic code.

In one embodiment the diterpene synthesis gene referred to herein is CBTol cyclase and may be encoded by a polynucleotide sequence comprising:
i) a polynucleotide sequence shown herein as SEQ ID No. 1, or
ii) a functional fragment of the polynucleotide sequence shown in i) which functional fragment encodes a diterpene synthesis gene, or
iii) a polynucleotide which encodes a polypeptide comprising the amino acid sequence shown herein as SEQ ID No. 2, or
iv) a polynucleotide sequence which can hybridize to the polynucleotide taught in i), ii) or iii) above under high stringency conditions, or
v) a polynucleotide sequence which has at least 70% (preferably 85%, more preferably 90%) identity with the polynucleotide shown in i), ii) or iii) above, or
vi) a polynucleotide sequence which differs from polynucleotide shown in i), ii) or iii) due to degeneracy of the genetic code.

In one embodiment the diterpene synthesis gene referred to herein is terpene synthase 3-8 and may be encoded by a polynucleotide sequence comprising:
i) a polynucleotide sequence shown herein as SEQ ID No. 3, or
ii) a functional fragment of the polynucleotide sequence shown in i) which functional fragment encodes a diterpene synthesis gene, or iii) a polynucleotide which encodes a polypeptide comprising the amino acid sequence shown herein as SEQ ID No. 4, or
iv) a polynucleotide sequence which can hybridize to the polynucleotide taught in i), ii) or iii) above under high stringency conditions, or
v) a polynucleotide sequence which has at least 70% (preferably 85%, more preferably 90%) identity with the polynucleotide shown in i), ii) or iii) above, or
vi) a polynucleotide sequence which differs from polynucleotide shown in i), ii) or iii) due to degeneracy of the genetic code.

In one embodiment the diterpene synthesis gene for use in accordance with the present invention may be endogenous to the tobacco plant.

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re) introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

In another embodiment the diterpene synthesis gene for use in accordance with the present invention may be exogenous to the tobacco plant.

To determine whether a gene is a diterpene synthesis gene for use in accordance with the present invention the skilled person can determine whether the gene is capable of producing diterpenes. One can measure the content of diterpenes as described above herein. Briefly a method to measure diterpene content may involve collecting exudate from a leaf or leaves by washing leaves or leaf discs with acetonitrile. The residue from the washes can then be derivatized to form tri-methyl silyl (TMS) esters (as described by Severson et al. 1985 supra, which is incorporated herein by reference). The TMS derivatives can then be separated and analysed by gas chromatography coupled to mass spectrometry (GC-MS). Eluted compounds can be identified by their retention time and by comparison of MS profiles with standards.

The present invention also provides the use of a diterpene synthesis gene for increasing the sucrose ester content of a plant.

Methods for decreasing expression of genes or gene products are well documented in the art.

In one embodiment the activity or expression of a diterpene synthesis gene may be inhibited by any method known in the art. Suitably, the activity or expression of a diterpene synthesis gene selected from a group of diterpene synthesis genes consisting of cyclase 2 gene (CYC2), CBTol cyclase and terpene synthase 3-8 may be inhibited by any method known in the art. Suitably, the activity or expression of the cyclase 2 gene (CYC2), may be inhibited by any method known in the art. Suitably, the activity or expression of CBTol cyclase may be inhibited by any method known in the art. Suitably, the activity or expression of terpene synthase 3-8 may be inhibited by any method known in the art.

Methods for inhibiting the activity or expression of a diterpene synthesis gene may include RNA interference, antisense or sense co-suppression (see Wang and Wagner 2003, Planta Volume 216, Issue 4, pp 686-691, which is incorporated herein by reference), gene editing or targeted mutagenesis. In one embodiment the inhibition of activity or expression of a diterpene synthesis gene may be achieved by the use of gene-editing. Gene-editing may be carried out using any method known in the art. A few non-limiting examples are presented herein.

In one embodiment the inhibition of activity or expression of a diterpene synthesis gene may be achieved using gene editing methods including CRISPR, including use of the CRISPR-Cas9 system. CRISPR/Cas9 genomic editing tools are available commercially such as "Guide-it" from Clontech (Avenue du President Kennedy 78100 Saint-Germain-en-Laye, France).

Another method of gene-editing includes the use of TALEN (transcription activator-like effector nuclease) technology with kits available commercially (e.g. from Addgene, 1Kendall Sq. Ste. B7102, Cambridge, Mass. 02139, USA). In one embodiment the inhibition of activity or expression of a diterpene synthesis gene may be achieved using TALEN.

In another embodiment the method may comprise the use of Zinc Finger Nucleases such as the CompoZr® Zinc Finger Nuclease Technology available from Sigma-Aldrich. Another embodiment may comprise the use of meganucleases (or a further method) described in Silva et al. Curr Gene Ther. Feb 2011; 11(1): 11-27 (the teaching of which is incorporated herein by reference).

In one embodiment the method for inhibiting the activity or expression of a diterpene synthesis gene may be targeted mutagenesis. Any method of targeted mutagenesis may be used. In one embodiment the method may be oligonucleotide-directed mutagenesis (ODM) such as KeyBase® available from Keygene (Agro Business Park 90,6708 PW Wageningen, The Netherlands). In another embodiment, inhibition of the activity or expression of a diterpene synthesis gene may be achieved by use of a construct or vector (e.g. a plasmid).

Genetic constructs of the invention may be in the form of an expression cassette, which may be suitable for inhibition of the activity or expression of a diterpene synthesis gene in a host cell. The genetic construct may be introduced into a host cell without it being incorporated in a vector. For instance, genetic construct, which may be a nucleic acid molecule, may be incorporated within a liposome or a virus particle. Alternatively, a purified nucleic acid molecule (e.g. histone-free DNA or naked DNA) may be inserted directly into a host cell by suitable means, e.g. direct endocytotic uptake. The genetic construct may be introduced directly into cells of a host subject (e.g. a plant) by transfection, infection, microinjection, cell fusion, protoplast fusion or ballistic bombardment. Alternatively, genetic constructs of the invention may be introduced directly into a host cell using a particle gun.

Alternatively, the genetic construct may comprise or be harboured within a recombinant vector, for expression in a suitable host cell. The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both *E. coli* and *Agrobacterium tumefaciens*. For example, a suitable vector may be a pBIN plasmid, such as pBIN19 (Bevan M., 1984, Nucleic Acids Research 12:8711-21).

Recombinant vectors may include a variety of other functional elements in addition to the sequence which inhibits the activity or expression of the diterpene synthesis gene. For example, the vector may comprise a promoter. In addition, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favor targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. to trichomes or glandular trichomes. Hence, the vector may comprise at least one additional element selected from a group consisting of: a selectable marker gene (e.g. an antibiotic resistance gene); a polypeptide termination signal; and a protein targeting sequence (e.g. a transit peptide).

In one embodiment, the method or use may comprise inhibiting the activity or expression of a diterpene synthesis gene using RNAi. In one embodiment the RNAi method uses miRNA e.g. artificial micro-RNA (amiRNA). In one embodiment the RNAi method uses siRNA. In one embodiment the RNAi method uses dsRNA.

In one embodiment, the method or use may comprise inhibiting the activity or expression of a diterpene synthesis gene using an interfering oligonucleotide. In one embodiment the oligonucleotide is RNA based. In one embodiment the oligonucleotide is RNA interference (RNAi), e.g. dsRNAi. In one embodiment the method may comprise transforming a cell of a tobacco plant with an RNAi molecule, e.g. dsRNAi, which inhibits the activity or expression of a diterpene synthesis gene.

In one embodiment tobacco plants and tobacco plant propagation materials are provided wherein expression of a diterpene synthesis gene is inhibited using RNAi (e.g. dsRNAi). The method may comprise regenerating the tobacco plant from the transformed cell.

The RNAi (e.g. dsRNAi) molecule may be capable of decreasing, in the transformed plant, the activity or expression of a diterpene synthesis gene by at least 30%, 35%, 40%, 45%, 50%, 55%, 60%, 65%, 70%, 75%, 80%, 85%, 90%, 95% or more, or by 100% compared to the concentration of the polypeptide in the wild-type plant, which has not been transformed with the RNAi molecule.

In one embodiment the RNAi molecule may be capable of decreasing, in the transformed plant, the activity or expression of a diterpene synthesis gene by 30% to 100%, preferably from 40% to 100%, more preferably 90% to 100%.

The activity or expression of a diterpene synthesis gene may be inhibited by any method known in the art. Suitably, the activity or expression of a diterpene synthesis gene selected from a group of diterpene synthesis genes consisting of cyclase 2 gene (CYC2), CBTol cyclase, and terpene synthase 3-8 may be inhibited by any method known in the art.

Suitably the method may comprise transforming a cell of a tobacco plant with a ddRNAi DNA construct which encodes RNA which forms a hairpin structure which is processed by endogenous pathways in the cell into small or short interfering RNA (siRNA).

Suitably, the activity or expression of the cyclase 2 gene (CYC2) may be inhibited by any method known in the art. In one embodiment the sequence of the cyclase 2 gene (CYC2) is as set forth in SEQ ID No. 8. In one embodiment the amino acid sequence of the cyclase 2 gene (CYC2) is as set forth in SEQ ID No. 10. The expression of the cyclase 2 gene (CYC2) may be inhibited by any method including gene editing methods including CRISPR, including use of the CRISPR-Cas9 system, RNA interference (RNAi), antisense or sense co-suppression, gene editing or targeted mutagenesis. In one embodiment, the activity or expression of the cyclase 2 gene (CYC2) may be inhibited by RNAi. The activity or expression of the cyclase 2 gene (CYC2) may be inhibited by RNAi using miRNA, siRNA, dsRNA or shRNA.

In one embodiment the method of inhibiting the activity or expression of the cyclase 2 gene (CYC2) targets at least part of exon 1, at least part of exon 2 and at least part of exon 3 of the cyclase 2 gene (CYC2). In a preferred embodiment the method targets at least part of exon1, at least part of exon 2 and at least part of exon 3 of the cyclase 2 gene (CYC2). In one embodiment the method targets at least part of exon 1, at least part of exon 2 and the first 115 nucleotides of the 3rd exon of the cyclase 2 gene (CYC2). In one embodiment the method targets nucleotides 1-25, nucleotides 26-271 (exon 1), nucleotides 1253-1529 (exon 2) and the first 115 nucleotides of the 3rd exon (nucleotides 2366-2480) of the cyclase 2 gene (CYC2) where the numbering is determined by alignment with SEQ ID No. 8.

In any of the preceding embodiments the activity or expression of the cyclase 2 gene (CYC2) may be inhibited using gene editing methods including CRISPR, including use of the CRISPR-Cas9 system. In any of the preceding embodiments the activity or expression of the cyclase 2 gene (CYC2) may be inhibited using a RNAi method.

Suitably, the activity or expression of the CBTol cyclase gene may be inhibited by any method known in the art. In one embodiment the sequence of the CBTol cyclase gene is as set forth in SEQ ID No. 1. In one embodiment the amino acid sequence of the CBTol cyclase is as set forth in SEQ ID No. 2. The expression of the CBTol cyclase gene may be inhibited by any method including gene editing methods including CRISPR, including use of the CRISPR-Cas9 system, RNA interference (RNAi), antisense or sense co-suppression, gene editing or targeted mutagenesis. In one embodiment, the activity or expression of the CBTol cyclase gene may be inhibited by RNAi. The activity or expression of the CBTol cyclase gene may be inhibited by RNAi using miRNA, siRNA, dsRNA or shRNA.

In another embodiment the method of inhibiting the activity or expression of the CBTol cyclase gene targets at least part of exon 4, intron 4, exon 5, intron 5, exon 6, intron 6 and at least part of exon 7 of the CBTol cyclase. In a preferred embodiment the method targets at least part of exon 4, intron 4, exon 5, intron 5, exon 6, intron 6 and at least part of exon 7 of the CBTol cyclase gene.

In one embodiment the method targets nucleotides 5'-2854-4175-3' of the CBTol cyclase gene where the numbering is determined by alignment with SEQ ID No. 1.

In any of the preceding embodiments the activity or expression of the CBTol cyclase gene may be inhibited using gene editing methods including CRISPR, including use of the CRISPR-Cas9 system. In any of the preceding embodiments the activity or expression of the CBTol cyclase gene may be inhibited using a RNAi method.

Suitably, the activity or expression of terpene synthase 3-8 gene may be inhibited by any method known in the art. In one embodiment the sequence of the terpene synthase 3-8 gene is as set forth in SEQ ID No. 3. In one embodiment the amino acid sequence of terpene synthase 3-8 is as set forth in SEQ ID No. 4. The expression of the terpene synthase 3-8 gene may be inhibited by any method including gene editing methods including CRISPR, including use of the CRISPR-Cas9 system, RNA interference (RNAi), antisense or sense co-suppression, gene editing or targeted mutagenesis. In one embodiment, the activity or expression of the terpene synthase 3-8 gene may be inhibited by RNAi. The activity or expression of terpene synthase 3-8 gene may be inhibited by RNAi using miRNA, siRNA, dsRNA or shRNA. In one embodiment the method of inhibiting the activity or expression of the terpene synthase 3-8 gene targets at least nucleotides 1497 to 1517 of a terpene synthase 3-8 gene, where the numbering is determined by alignment with SEQ ID No. 3. In one embodiment the method of inhibiting the activity or expression of the terpene synthase 3-8 gene targets at least nucleotides 884 to 904 of a terpene synthase 3-8 gene, where the numbering is determined by alignment with SEQ ID No. 3. In a preferred embodiment the RNAi method targets nucleotides 884 to 904 of a terpene synthase 3-8 gene, where the numbering is determined by alignment with SEQ ID No. 3.

In any of the preceding embodiments the activity or expression of the terpene synthase 3-8 gene may be inhibited using gene editing methods including CRISPR, including use of the CRISPR-Cas9 system. In any of the preceding embodiments the activity or expression of the terpene synthase 3-8 gene may be inhibited using a RNAi method.

In one embodiment the method may comprise transforming a cell of a tobacco plant with a DNA-directed RNA interference (ddRNAi) construct which comprises a nucleotide sequence which encodes a dsRNA or a nucleotide sequence which encodes an amiRNA, packaged into a delivery vector.

In one embodiment the RNAi molecule is the dsRNA which is encoded by the ddRNAi DNA construct.

In one embodiment the RNAi molecule is the amiRNA which is encoded by the ddRNAi DNA construct. In one embodiment the present invention provides a construct comprising a ddRNAi DNA sequence which is designed to encode a dsRNA which inhibits the expression of a diterpene synthesis gene.

In another embodiment the present invention provides a construct comprising a ddRNAi DNA sequence which is designed to encode an amiRNA which inhibits the expression of a diterpene synthesis gene.

The construct may be comprised in a vector. Suitably the vector may be a plasmid.

In one embodiment, the vector for use in the present invention is the *Agrobacterium*-based plasmid pKYLX71: 35S2. This plasmid is based on the pGA471 plasmid described by An et al. (An, G. et al. 1985 EMBO J. 4, 277-284 which is incorporated herein by reference). In another embodiment the vector for use in the present invention is pCAMBIA2300. The pCAMBIA vector backbone is derived from the pPZP vectors.

The term "DNA-directed RNA interference (ddRNAi)" as used herein means a DNA construct which is used to activate a cell's endogenous RNA interference (RNAi) pathways. Suitably, these constructs are designed to express self-complementary RNAs, e.g. double stranded RNA (dsRNA) or single stranded RNA (ssRNA) or short-hairpin RNAs (shRNA) or micro RNA (e.g. artificial micro RNA—amiRNA), that once processed bring about silencing of a target gene or genes. Advantageously the use of ddRNAi means that the expressed RNA (e.g. dsRNA or amiRNA) is continually produced and thereby able to provide long-term silencing of targeted genes. In contrast, small interfering RNA (siRNA) administered directly to a cell (e.g. not continuously expressed from a ddRNAi DNA construct in accordance with the present invention) turn over within a cell and only silence genes transiently.

In one embodiment, the method or use may comprise inhibiting the activity or expression of a diterpene synthesis gene using dsRNA which is expressed from a ddRNAi DNA construct.

In another embodiment, the method or use may comprise inhibiting the activity or expression of a diterpene synthesis gene using amiRNA which is expressed from a ddRNAi DNA construct.

Accordingly in one embodiment tobacco plants and tobacco plant propagation materials, tobacco leaves, cut harvested leaves, processed tobacco leaves or cut and processed tobacco leaves are provided wherein expression of a diterpene synthesis gene is inhibited using an ddRNAi DNA construct. Suitably the ddRNAi DNA construct may be incorporated into the genomic DNA of the plant. The tobacco plant, tobacco plant propagation material, tobacco leaf, cut harvested leaf, processed tobacco leaf or cut and processed tobacco leaf may comprise the ddRNAi DNA construct which expresses a dsRNA or amiRNA which inhibits the activity or expression of a diterpene synthesis gene. The tobacco plant, tobacco plant propagation material, tobacco leaf, cut harvested leaf, processed tobacco leaf or cut and processed tobacco leaf which comprises the ddRNAi DNA construct which expresses a dsRNA or amiRNA which inhibits the activity or expression of a diterpene synthesis gene may have increased sucrose ester content compared to a tobacco plant, tobacco plant propagation material, tobacco leaf, cut harvested leaf, processed tobacco leaf or cut and processed tobacco leaf which does not comprise the ddRNAi DNA construct.

The ddRNAi DNA construct may comprise all or part of the diterpene synthesis gene. The construct may comprise exons and/or introns of the diterpene synthesis gene. The ddRNAi DNA construct may comprise partial gene sequences, which when transcribed produce a hairpin RNA structure. The RNA encoded by the ddRNAi DNA construct may have either an intron-hairpin or a GUS-hairpin structure, or may be single full-length RNA. As described herein the inventors have demonstrated the surprising efficacy of RNAi molecules which inhibit the activity or expression of a diterpene synthesis gene for use in increasing sucrose ester content in tobacco plants.

The term "exon" as used herein means part of a gene which encodes for the final mature RNA produced by a gene after introns have been removed by RNA splicing.

The term "intron" as used herein means a nucleotide sequence within a gene which is removed by RNA splicing during maturation of the final RNA product.

The term "at least part of" or "a partial sequence" as used herein means a sequence comprising at least 5, 10, 15, 20, 25, 30, 40, 45, 50, 60, 70, 80, 90, 100, 120, 140, 160, 180, 200, 220, 240, 260, 280, 300, 400 or at least 500 contiguous nucleotides. For example a ddRNAi DNA construct may comprise at least part of an exon, wherein the construct comprises 100 contiguous nucleotides from said exon.

The term "mRNA corresponding to" as used herein means that the RNA has the same sequence as the DNA i.e. the sequence of nucleotides is the same in both the mRNA and the DNA sequence except that in RNA, thymine (T) is replaced by uracil (U), and the deoxyribose is substituted by ribose.

The ddRNAi DNA construct may be used to inhibit the expression of the cyclase 2 gene (CYC2). In one embodiment the sequence of the cyclase 2 gene (CYC2) is as set forth in SEQ ID No. 8. In one embodiment the amino acid sequence of polypeptide encoded by the cyclase 2 gene (CYC2) is as set forth in SEQ ID No. 10. Suitably the ddRNAi DNA construct may comprise all or part of the cyclase 2 gene (CYC2).

In one embodiment the ddRNAi DNA construct may comprise at least a part exon 1, at least part of exon 2 and at least part of exon 3 of the cyclase 2 gene (CYC2). Suitably the ddRNAi DNA construct may comprise at least part of exon 1, at least part of exon 2 and the first 115 nucleotides of the 3rd exon of the cyclase 2 gene (CYC2). Suitably the ddRNAi DNA construct may comprise nucleotides 1-25, nucleotides 26-271 (exon 1), nucleotides 1253-1529 (exon 2) and the first 115 nucleotides of the 3rd exon (nucleotides 2366-2480) of the cyclase 2 gene (CYC2) where the numbering is determined by alignment with SEQ ID No. 8. Suitably the ddRNAi DNA construct may comprise the sequence set forth in SEQ ID No. 5.

The ddRNAi DNA construct may be used to inhibit the expression of the CBTol cyclase gene. In one embodiment the sequence of the CBTol cyclase gene is as set forth in SEQ ID No. 1. In one embodiment the amino acid sequence of the CBTol cyclase is as set forth in SEQ ID No. 2. Suitably the ddRNAi DNA construct may comprise all or part of the CBTol cyclase gene.

In another embodiment, the ddRNAi DNA construct may comprise at least part of exon 4, intron 4, exon 5, intron 5, exon 6, intron 6 and at least part of exon 7 of the CBTol cyclase gene. Suitably the ddRNAi DNA construct may comprise nucleotides 5'-2854-4175-3' of the CBTol cyclase gene where the numbering is determined by alignment with SEQ ID No. 1. Suitably the ddRNAi DNA construct may comprise the sequence set forth in SEQ ID No. 6.

The ddRNAi DNA construct may be used to inhibit the expression of the terpene synthase 3-8 gene. Suitably the ddRNAi DNA construct may comprise all or part of the terpene synthase 3-8 gene. Suitably the ddRNAi DNA construct may comprise at least nucleotides 1497 to 1517 of a terpene synthase 3-8 gene, where the numbering is determined by alignment with SEQ ID No. 3. In one embodiment the sequence of the terpene synthase 3-8 gene is as set forth in SEQ ID No. 3. In one embodiment the amino acid sequence of terpene synthase 3-8 is as set forth in SEQ ID No. 4. Suitably the ddRNAi DNA construct may comprise the sequence set forth in SEQ ID No. 7. Suitably the ddRNAi DNA construct may comprise at least nucleotides 884 to 904 of a terpene synthase 3-8 gene, where the numbering is determined by alignment with SEQ ID No. 3. Suitably the ddRNAi DNA construct may comprise the sequence set forth in SEQ ID No. 11.

The sequence of the ddRNAi DNA construct which encodes a dsRNA in one embodiment may comprise a sequence set forth in SEQ ID No.7. A dsRNA expressed from the ddRNAi DNA construct comprising SEQ ID No.7 may be used to inhibit the activity or expression of or to down-regulate a diterpene synthesis gene wherein the diterpene synthesis gene is the cyclase 2 gene (CYC2).

The sequence of the ddRNAi DNA construct which encodes a dsRNA in another embodiment may comprise a sequence as set forth in SEQ ID No.8. A dsRNA expressed from the ddRNAi DNA construct comprising SEQ ID No.8 may be used to inhibit the activity or expression of or to down-regulate a diterpene synthesis gene wherein the diterpene synthesis gene is the CBTol cyclase gene.

The sequence of the ddRNAi DNA construct which encodes an amiRNA in one embodiment may comprise a sequence as set forth in SEQ ID No.9. An amiRNA expressed from the ddRNAi DNA construct comprising SEQ ID No.9 may be used to inhibit the activity or expression of or to down-regulate a diterpene synthesis gene wherein the diterpene synthesis gene is the terpene synthase 3-8 gene.

The term "GW1" or "GW-1" as used here may mean a ddRNAi DNA construct comprising at least part of exon 1, at least part of exon 2 and the first 115 nucleotides of the 3rd exon of the cyclase 2 gene (CYC2).

The term "GW2" or "GW-2" as used here may mean a ddRNAi DNA construct comprising at least nucleotides and 1497 to 1517 of a terpene synthase 3-8 gene, where the numbering is determined by alignment with SEQ ID No. 3.

The term "GW3" or "GW-3" as used here may mean a ddRNAi DNA construct comprising at least part of exon 4, intron 4, exon 5, intron 5, exon 6, intron 6 and at least part of exon 7 of the CBTol cyclase gene.

The term "GW5" or "GW-5" as used here may mean a ddRNAi DNA construct comprising at least nucleotides 884 to 904 of a terpene synthase 3-8 gene, where the numbering is determined by alignment with SEQ ID No. 3.

Thus, the ddRNAi DNA construct of the invention may comprise a nucleotide sequence which encodes a dsRNA wherein the dsRNA encoding sequence is a nucleotide sequence substantially as set out in SEQ ID No. 5 or 8 or a functional variant, or fragment thereof.

Suitably, the ddRNAi DNA construct of the invention may comprise a nucleotide sequence which encodes a dsRNA wherein the dsRNA encoding sequence is a nucleotide sequence substantially as set out in SEQ ID No. 5 or a functional variant, or fragment thereof.

Suitably, the ddRNAi DNA construct of the invention may comprise a nucleotide sequence which encodes a dsRNA wherein the dsRNA encoding sequence is a nucleotide sequence substantially as set out in SEQ ID No. 6 or a functional variant, or fragment thereof.

In another embodiment the ddRNAi DNA construct of the invention may comprise a nucleotide sequence which encodes an amiRNA wherein the amiRNA encoding sequence is a nucleotide sequence substantially as set out in SEQ ID No.9.

It will be appreciated that it would be relatively straightforward for the skilled person to modify the sequence which encodes the dsRNA (e.g. SEQ ID No.7) or amiRNA (e.g. SEQ ID No.9) to produce variants or fragments of the ddRNAi DNA construct, which would still function to inhibit or down-regulate the expression of the diterpene synthesis gene, thereby increasing the sucrose content of a tobacco plant. Functional variants and fragments of a ddRNAi DNA construct may be readily identified by using standard laboratory techniques to determine whether or not the level of mRNA encoded by the diterpene synthesis gene has been reduced to below the level of the same diterpene synthesis gene mRNA in a corresponding wild-type plant cell, grown under the same conditions. An example of such a technique is polymerase chain reaction (PCR). The skilled technician would appreciate that the concentration of the polypeptide encoded by the diterpene synthesis gene may be measured directly in wild-type and transgenic plants, by using standard techniques, such as Enzyme-linked immunosorbent assays (ELISA), Fluorescence-activated cell sorting, Western blotting or Chromatin Immunoprecipitation (ChIP).

In another embodiment the tobacco cell, tobacco plant or part thereof, and/or plant propagation material may comprise a construct which inhibits the activity or expression of a diterpene synthesis gene. In a preferred embodiment the construct is a ddRNAi DNA construct, more preferably the ddRNAi DNA construct comprises an RNAi module which inhibits the activity or expression of a cyclase 2 gene (CYC2), a CBTol cyclase gene or a terpene synthase 3-8 gene.

In a further embodiment the tobacco cell, tobacco plant or part thereof and/or plant propagation material may comprise:

i) a polynucleotide sequence shown herein as SEQ ID No. 5, SEQ ID No. 6 or SEQ ID No. 7, SEQ ID No. 11 or ii) a fragment of the polynucleotide sequence shown in i) which functional fragment inhibits the activity or expression of a diterpene synthesis gene, or iii) a polynucleotide sequence which has at least 70% (preferably 85%, more preferably 90%) identity with the polynucleotide shown in i), or ii) above.

In one embodiment the polynucleotide sequence may have at least 80% identity with SEQ ID No.

5, SEQ ID No. 6 or SEQ ID No. 7, or SEQ ID No. 11. Suitably the polynucleotide sequence may have at least 90% identity with SEQ ID No. 5, SEQ ID No. 6 or SEQ ID No. 7, or SEQ ID No. 11. Suitably the polynucleotide sequence may have at least 95% identity (more suitably at least 99% identity) with SEQ ID No. 5, SEQ ID No. 6 or SEQ ID No. 7, or SEQ ID No. 11.

In an advantageous embodiment, inhibition of the activity or expression of a diterpene synthesis gene may result in an increase of sucrose ester content of a tobacco plant and simultaneously in the alteration of one or more other flavour components of the tobacco plant. Inhibition of the activity or expression of a diterpene synthesis gene may result in the increase of sucrose ester content and in alteration of diterpene content. The increase in sucrose ester content may be accompanied by an increase in one or more of the flavour compounds selected from the group consisting of: cis-abienol, labdenediol and CBT-ol content.

The increase in sucrose ester content may be accompanied by an increase in cis-abienol content and an increase in labdenediol content. In another embodiment the increase in sucrose ester content may be accompanied by an increase in labdenediol content. The increase in sucrose ester content may be accompanied by an increase in CBT-ol and high cis-abienol content.

In one embodiment the method of the invention produces a Burley or Flue-cured leaf which has Turkish-like exudate chemistry. Preferably the Burley or Flue-cured leaf has chemistry more similar to a Turkish-like tobacco than a comparative Burley or Flue-cured plant which does not have inhibited activity or expression of a diterpene synthesis gene.

In one embodiment the tobacco plant or part thereof according to the present invention is a Burley or Flue-cured plant modified in accordance with the present invention. In one embodiment the present invention relates to a Burley or Flue-cured plant modified in accordance with the present invention to have Turkish-like exudate chemistry. In one embodiment the tobacco plant (e.g. modified tobacco plant) according to the present invention is not an Oriental or Turkish tobacco plant.

In one embodiment the tobacco plant or part thereof is cured. In one embodiment the tobacco plant or part thereof is cured e.g. air-cured, flue-cured, fire-cured or sun-cured. In a further aspect, the tobacco plant or part thereof is flue-cured. In a further aspect, the tobacco plant or part thereof is air-cured.

Flue-curing is well-known in the art and refers to the process of curing tobacco with flues which are fed by fire boxes or gas fuelled systems. This process heat-cures the tobacco without exposing it to smoke, slowly raising the temperature over the course of the curing. This method produces tobacco that is high in sugar and has medium to high levels of nicotine. The Smith Tobacco Barn is an example of a traditional, flue-cured tobacco barn.

Air-cured tobaccos include Burley, Maryland, and dark tobaccos. The common factor is that curing is primarily without artificial sources of heat and humidity. Burley tobaccos are light to dark brown in colour, high in oil, and low in sugar. Burley tobaccos are air-cured in barns. Major Burley growing countries are Argentina, Brazil, Italy, Malawi, and the U.S. Burley tobacco plants include, for example, Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R711, R 712, NCBH 129, Bu 21xKy 10, HBO4P, Ky 14xL 8, Kt 200, Newton 98, Pedigo 561, Pf561 and Va 509. Maryland tobaccos are extremely fluffy, have good burning properties, low nicotine and a neutral aroma. Major Maryland growing countries include the U.S. and Italy. Dark air-cured tobaccos are distinguished from other types primarily by its fermentation process which gives dark air-cured tobacco its medium- to dark-brown colour and distinct aroma. Their leaves have low sugar content but high nicotine content. Dark air-cured tobaccos are mainly used in the production of chewing tobacco and snuff. Major growing regions for dark fire-cured tobaccos are Tennessee, Kentucky, and Virginia, USA.

In a preferred embodiment the tobacco of the invention contains at least as much 3-methyl valerate acetylated sucrose ester as the Turkish-like tobaccos. "Turkish-like exudate chemistry" means that the exudate produced by the plant of the invention has exudate chemistry similar to that observed in Turkish tobacco. The chemistry of Turkish (or Oriental) tobacco e.g. *N. tabacum* var. Samsun has been characterised by R. Severson et al. 1985 (supra, which is incorporated herein by reference). Turkish tobacco is known to contain low levels of CBT-diols, high levels of oxidation products of CBTs and high levels of 3-methylvaleric acid containing sucrose ester. Accordingly, the invention advantageously provides a higher biomass tobacco plant with a Turkish tobacco-like trichome exudate.

In one embodiment there is provided a tobacco plant which comprises increased 3-methyl valerate sucrose esters. The tobacco plant may comprise increased 3-methyl valerate sucrose esters in comparison to a tobacco plant which has not been modified according to the present invention, i.e. a plant in which the inhibition of the diterpene synthesis gene has not been introduced. Preferably the tobacco lines of the invention contain at least twice as much 3-methyl valerate sucrose ester as control tobacco plant which has not been modified to inhibit the activity or expression of a diterpene synthesis gene. In a further aspect, the tobacco plant of the invention contains at least as much 3-methyl valerate as the Turkish type tobaccos.

Advantageously the tobacco plants of the invention have normal growth in the field. In one embodiment, the CBTol synthase knockdown plants advantageously have low CBT-diols, high cis- abienol, high 3-methyl valeric containing sucrose esters like Turkish tobaccos, but unlike Turkish types, the CBTol synthase knockdown plants of the invention may produce higher biomass than Turkish tobacco plants. For Turkish tobacco types the yield is typically in the range of 600 to 1100 lbs/acre.

The term "functional fragment" as used herein refers to a portion of a polynucleotide that is capable of functioning in the same way as the polynucleotide. For example, if the polynucleotide is a diterpene synthesis gene then the function fragment must be capable of functioning as a diterpene synthesis gene, e.g. the functional fragment retains the activity of the diterpene synthesis gene. The functional fragment may have a level of activity which is equal to or greater than the level of activity of a full length polynucleotide. If the polynucleotide encodes a dsRNA or amiRNA, then the functional fragment must be capable of inhibiting the activity or expression of a diterpene synthesis gene.

In one embodiment a functional fragment may be a portion of a diterpene synthesis gene as discussed herein comprising at least 50, 75, 100, 150, 200, 300, 400, 500, 600, 700, 800, 900 or 1000 contiguous nucleotides. In some embodiments the functional fragment may comprise at least 150 nucleotides of a diterpene synthesis gene discussed herein. In one embodiment where the functional fragment is a functional fragment of a ddRNAi DNA construct, the functional fragment may be a portion of a RNAi as discussed herein comprising at least 50, 75, 100, 150, 200 or 250 contiguous nucleotides.

The term "degeneracy of the genetic code" as used herein refers to the redundancy in codons encoding polypeptide sequences exhibited as the multiplicity of three-codon combinations specifying an amino acid. For example in an mRNA molecule encoding a polypeptide having an isoleucine amino acid, isoleucine can be encoded by AUU, AUC or AUA. This means that a DNA molecule encoding the RNA can have multiple sequences yet the resulting polypeptide will have the same sequence. In other words polymorphic nucleotide sequences can encode the same polypeptide product. This means that one nucleic acid sequence can comprise a sequence with very low sequence identity to a second sequence while encoding the same polypeptide sequence.

The method and uses of the present invention comprise the inhibition of at least one diterpene synthesis gene. The inhibition can be achieved by any means known to the person skilled in the art.

In some embodiments of the present invention a promoter may be provided. The promoter for use in the present invention may be one or more selected from the group consisting of: a constitutive promoter, a senescence-specific promoter, a tissue-specific promoter, a developmentally-regulated promoter and an inducible promoter. In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter, Nature. 313 810-2) and the rice actin 1 gene (Zhang W, McElroy D, Wu R. (1991) are incorporated herein by reference. Analysis of rice Act1 5' region activity in transgenic rice plants. (Plant Cell 3 1155-65 which is incorporated herein by reference.) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81 (which is incorporated herein by reference)). Constitutive promoters such as the Carnation Etched Ring Virus (CERV) promoter (Hull R, Sadler J, Longstaff M (1986 which is incorporated herein by reference). The sequence of carnation etched ring virus DNA: comparison with cauliflower mosaic virus and retroviruses. *EMBO Journal,* 5(2):3083-3090) which is incorporated herein by reference).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene. Suitably the promoter may be a CERV promoter.

Alternatively in some embodiments the promoter may not be a cauliflower mosaic virus (CaMV 35S promoter). In one embodiment the promoter may be a senescence-specific promoter. A "senescence-specific promoter" (SAG) can be a promoter, which is associated with controlling the expression of a senescence-associated gene. Hence, the promoter can restrict expression of a coding sequence (i.e. a gene) to which it is operably linked substantially exclusively in senescing tissue. Therefore, a senescence-specific promoter can be a promoter capable of preferentially promoting gene expression in a plant tissue in a developmentally-regulated manner such that expression of a 3' protein-coding region occurs substantially only when the plant tissue is undergoing senescence. It will be appreciated that senescence tends to occur in the older parts of the plant, such as the older leaves, and not in the younger parts of the plants, such as the seeds.

One example of a plant which is known to express numerous senescence-associated genes is *Arabidopsis*. Hence, the promoter in may be isolated from a senescence-associated gene in *Arabidopsis*. Gepstein et al. (The Plant Journal, 2003, 36, 629-642), incorporated herein by reference, conducted a detailed study of SAGs and their promoters using *Arabidopsis* as a model. The genetic construct may comprise a promoter from any of the SAGs disclosed in this paper.

For example, a suitable promoter may be selected from a group consisting of SAG12, SAG13, SAG101, SAG21 and SAG18, ora functional variant ora functional fragment thereof.

In one embodiment the promoter may be a SAG12 or a SAG13 promoter. In one embodiment, the promoter may be a SAG12 promoter, which will be known to the skilled technician, or a functional variant or a fragment thereof (Gan & Amasino, 1997, Plant Physiology, 113: 313-319), incorporated herein by reference. Suitable promoters and sequences thereof may be found in WO2010/097623 (incorporated herein by reference).

In another embodiment the promoter may be a tissue-specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. A number of tissue-specific promoters are known in the art and include those associated with the patatin gene expressed in potato tuber and the high molecular weight glutenin gene expressed in wheat, barley or maize endosperm. Any of these promoters may be used in the present invention.

Suitably the tissue-specific promoter may be a leaf-specific promoter. Suitably leaf-specific promoters may include *ASYMMETRIC LEAVES* 1 (AS1). In a particularly preferred embodiment the tissue-specific promoter is not a root-specific promoter.

In another embodiment the promoter may be a developmentally-regulated promoter. A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter. An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. (1993) (Isolation of an asparagus intracellular PR gene (AoPR1) wound-responsive promoter by the inverse polymerase chain reaction and its characterization in transgenic tobacco. Plant J. 3 191-201.) incorporated herein by reference, temperature response as disclosed by Benfey & Chua (1989) (Benfey, P. N., and Chua, N-H. (1989) Regulated genes in transgenic plants. Science 244 174-181) incorporated herein by reference, and chemically induced, as described by Gatz (1995) (Gatz, C. (1995) Novel inducible/repressible gene expression systems. Methods in Cell Biol. 50 411-424) incorporated herein by reference.

Thus in one embodiment the promoter may be selected from the group consisting of: the CERV promoter, the cauliflower mosaic virus 35S promoter (full or truncated), the rubisco promoter, the pea plastocyanin promoter, the nopaline synthase promoter, the chlorophyll r/b binding promoter, the high molecular weight glutenin promoter, the α, β-gliadin promoter, the hordein promoter and the patatin promoter.

In one embodiment the promoter may be the CaMV 35S promoter or a modified 35S promoter with a duplicated enhancer region or double enhancer region (R. Kay et al. *Science*. 1987 Jun. 5; 236(4806):1299-302 which is incorporated herein by reference).

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and sul respectively; EP-A-242246, EP-A-0249637); and screenable markers such as beta-glucuronidase (GB2197653), luciferase and green fluorescent protein (GFP). The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

Commercially Desirable Traits

The term "commercially desirable traits" will include traits such as yield, mature plant height, harvestable leaf number, average node length, cutter leaf length, cutter leaf width, quality, abiotic (for instance drought) stress tolerance, herbicide tolerance and/or biotic (for instance insect, bacteria or fungus) stress tolerance.

The term "commercially desirable traits" as taught herein means one or more traits selected from the group consisting of drought resistance, pest resistance, mature plant height, harvestable leaf number, average node length, cutter leaf length, cutter leaf width, and yield comparable to those said traits in the flue-cured parent of a comparable plant when grown in similar field conditions.

Unless specified otherwise, used herein, tobacco yield refers to cured leaf yield which is calculated based on the weight of cured tobacco leaves per acre under standard field conditions following standard agronomic and curing practice.

In one aspect, a tobacco plant of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the tobacco plant yield of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions In another aspect, the yield of a tobacco plant of the present invention is comparable to the yield of the flue cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Tobacco Plants

The present invention provides methods, uses directed to tobacco plants as well as a tobacco cell, a tobacco plant and a plant propagation material.

The term "tobacco" as used herein refers to a plant in the genus *Nicotiana* that is used in the production of tobacco products. Non-limiting examples of suitable "tobacco" plants include *N. tabacum* and *N. rustica* (for example, *N. tabacum* L., LA B21, LN KY171, TI 1406, Basma, Galpao, Perique, Beinhart 1000-1, and Petico).

In one embodiment a suitable tobacco plant may be any *N. tabacum* species.

In another embodiment a suitable tobacco plant may be a non-tabacum species.

The tobacco material can be derived or obtained from varieties of *Nicotiana tabacum* species, commonly known as Burley varieties, flue or bright varieties and dark varieties. In some embodiments, the tobacco material is derived from a Burley, Virginia or a dark tobacco plant. The tobacco plant may be selected from Burley tobacco, rare tobacco, speciality tobacco, expanded tobacco or the like.

The use of tobacco cultivars and elite tobacco cultivars is also contemplated herein. The tobacco plant for use herein may therefore be a tobacco variety or elite tobacco cultivar. Particularly useful *Nicotiana tabacum* varieties include Burley type, dark type and flue-cured type tobaccos.

In some embodiments, the tobacco plant may be, for example, selected from one or more of the following varieties: *N. tabacum* L. cultivar T.I. 1068, *N. tabacum* AA 37-1, *N. tabacum* B 13P, *N. tabacum* Xanthi (Mitchell-Mor), *N. tabacum* KT D#3 Hybrid 107, *N. tabacum* Bel-W3, *N. tabacum* 79-615, *N. tabacum* Samsun Holmes NN, F4 from cross N. tabacum BU21 x *N. tabacum* Hoja Parado, line 97, *N. tabacum* KTRDC#2 Hybrid 49, *N. tabacum* KTRDC#4 Hybrid 1 10, *N. tabacum* Burley 21, *N. tabacum* PM016, *N. tabacum* KTRDC#5 KY 160 SI, *N. tabacum* KTRDC#7 FCA, *N. tabacum* KTRDC#6 TN 86 SI, *N. tabacum* PM021, *N. tabacum* K 149, *N. tabacum* K 326, *N. tabacum* K 346, *N. tabacum* K 358, *N. tabacum* K 394, *N. tabacum* K 399, *N. tabacum* K 730, *N. tabacum* KY 10, *N. tabacum* KY 14, *N. tabacum* KY 160, *N. tabacum* KY 17, *N. tabacum* KY 8959, *N. tabacum* KY 9, *N. tabacum* KY 907, *N. tabacum* MD 609, *N. tabacum* McNair 373, *N. tabacum* NC 2000, *N. tabacum* PG 01, *N. tabacum* PG 04, *N. tabacum* P01, *N. tabacum* P02, *N. tabacum* P03, *N. tabacum* RG 1 1, *N. tabacum* RG 17, *N. tabacum* RG 8, *N. tabacum* Speight G-28, *N. tabacum* TN 86, *N. tabacum* TN 90, *N. tabacum* VA 509, *N. tabacum* AS44, *N. tabacum* Banket A1, *N. tabacum* Basma Drama B84/31, *N. tabacum* Basma I Zichna ZP4/B, *N. tabacum* Basma Xanthi BX 2A, N. tabacum Batek, *N. tabacum* Besuki Jember, *N. tabacum* C104, *N. tabacum* Coker 319, *N. tabacum* Coker 347, *N. tabacum* Criollo Misionero, *N. tabacum* PM092, *N. tabacum* Delcrest, *N. tabacum* Djebel 81, *N. tabacum* DVH 405, *N. tabacum* Galpao Comum, *N. tabacum* HBO4P, *N. tabacum* Hicks Broadleaf, *N. tabacum* Kabakulak Elassona, *N. tabacum* PM102, *N. tabacum* Kutsage E1, *N. tabacum* KY 14xL8, *N. tabacum* KY 171, *N. tabacum* LA BU 21, *N. tabacum* McNair 944, *N. tabacum* NC 2326, *N. tabacum* NC 71, *N. tabacum* NC 297, *N. tabacum* NC 3, *N. tabacum* PVH 03, *N. tabacum* PVH 09, *N. tabacum* PVH 19, *N. tabacum* PVH 21 10, *N. tabacum* Red Russian, *N. tabacum* Samsun, *N. tabacum* Saplak, *N. tabacum* Simmaba, *N. tabacum* Talgar 28, *N. tabacum* PM132, *N. tabacum* Wislica, *N. tabacum* Yayaldag, *N. tabacum* NC 4, *N. tabacum* TR Madole, *N. tabacum* Prilep HC-72, *N. tabacum* Prilep P23, *N. tabacum* Prilep PB 156/1, *N. tabacum* Prilep P12-2/1, *N. tabacum* Yaka JK-48, *N. tabacum* Yaka JB 125/3, *N. tabacum* TI-1068, *N. tabacum* KDH-960, *N. tabacum* TI-1070, *N. tabacum* TW136, *N. tabacum* PM204, *N. tabacum* PM205, *N. tabacum* Basma, *N. tabacum* TKF 4028, *N. tabacum* L8, *N. tabacum* TKF 2002, *N. tabacum* TN90, *N. tabacum* GR141, *N. tabacum* Basma xanthi, *N. tabacum* GR149, *N. tabacum* GR153, and *N. tabacum* Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 1 1, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HBO4P, Hicks Broadleaf, Kabakulak Elassona, Kutsage El, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant may be a Burley.

In one embodiment the tobacco plant is a *N. tabacum* L. in the most preferred embodiment, the tobacco plant is *N. tabacum* L cultivar T.I. 1068.

In one embodiment the plant propagation material may be obtainable from a tobacco plant of the invention. A "plant propagation material" as used herein refers to any plant matter taken from a plant from which further plants may be produced. Suitably the plant propagation material may be a seed.

In one embodiment the tobacco cell, tobacco plant and/or plant propagation material of the invention may comprise an inhibited or down-regulated diterpene synthesis gene. In another embodiment the tobacco cell, tobacco plant and/or plant propagation material may comprise a construct or vector according to the invention. In another embodiment the tobacco cell, tobacco plant and/or plant propagation material may be obtainable (e.g. obtained) by a method according to the invention.

Suitably a tobacco plant or part thereof according to the present invention may comprise reduced expression of at least one diterpene synthesis gene when compared to a tobacco plant or part thereof that does not been modified to inhibit the expression of a diterpene synthesis gene.

In one embodiment the tobacco plant or part thereof in accordance with the present invention comprises a tobacco cell of the invention. In another embodiment the plant propagation material may be obtainable (e.g. obtained) from a tobacco plant of the invention.

In one embodiment there is provided the use of a tobacco cell as provided for in the foregoing embodiments for production of a tobacco product. Additionally there is provided the use of a tobacco plant as described herein to breed a tobacco plant.

The present invention also provides in another embodiment the use of a tobacco plant of the foregoing embodiments for the production of a tobacco product. In another embodiment there is provided the use of a tobacco plant of the invention to grow a crop. In one embodiment the use of a diterpene synthesis gene according to the present invention may result in an alteration in the exudate chemistry of a tobacco plant.

In one embodiment the use of a diterpene synthesis gene according to the present invention may result in an increase in the sucrose ester content of a tobacco plant. In another embodiment the use of a diterpene synthesis gene (e.g. inhibition thereof) may result in an increase in the trichome exudate concentration of sucrose ester and an increase in the content of one or more of CBT-ol, cis-abienol and labdene-diol. Suitably this may be observed when a plant exhibits decreased diterpene synthesis gene expression compared to wild type plants.

In one embodiment the present invention provides a tobacco cell culture (e.g. in in vitro culture). The tobacco cell culture may be a tobacco cell suspension culture. These tobacco cells cultured in vitro may be incorporated into a tobacco product, e.g. as a substitute for conventional tobacco particles, shreds, fine cut or long cut tobacco lamina, as an additive ingredient or as both a substitute and an additive.

In one embodiment there is provided the use of a tobacco cell culture, e.g. a harvested and/or processed tobacco cell culture, or an extract therefrom according to the present invention for the production of a tobacco product.

The tobacco cells harvested from an in vitro culture may be dried, e.g. freeze-dried, for example to produce a powder.

The skilled person will be aware of known methods for establishing in vitro cultures of tobacco cells. By way of example only the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture or an extract therefrom may be incorporated into tobacco products according to the present invention.

Products

The present invention also provides for products obtainable or obtained from tobacco according to the present invention. Products are provided which are obtainable or obtained from a tobacco plant in which diterpene synthesis gene activity or expression has been inhibited and which comprises increased sucrose ester content.

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco products such as snus and snuff, which aerosol-free delivery articles may or may not deliver nicotine.

Suitably, the tobacco industry product may be prepared from (e.g. may comprise) a tobacco plant or a part thereof according to the present invneiton.

Suitably, the tobacco industry product may be prepared from a tobacco cell culture according to the present invention.

Suitably, the tobacco industry product may be prepared from (e.g. may comprise) a tobacco plant or part thereof propagated from a tobacco plant propagation material according to the present invention.

Suitably, the tobacco industry product may be prepared from (e.g. may comprise) a harvested leaf of a tobacco plant according to the present invention.

Suitably, the tobacco industry product may be prepared from (e.g. may comprise) a processed tobacco leaf according to the present invention.

Suitably, the tobacco industry product may be prepared from (e.g. may comprise) a cured tobacco material according to the present invention.

Suitably, the tobacco industry product may be prepared from (e.g. may comprise) a tobacco blend according to the present invention.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non- combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material.and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In another embodiment, the product may comprise a ddRNAi DNA construct of the invention which inhibits diterpene synthesis gene activity or expression and increased sucrose ester content.

In one embodiment there is provided the use of a tobacco plant of the invention to produce tobacco leaf. Suitably the tobacco leaf may be subjected to downstream applications such as processing. Thus in one embodiment the use of the foregoing embodiment may provide a processed tobacco leaf. Suitably the tobacco leaf may be subjected to curing, fermenting, pasteurising or combinations thereof.

In another embodiment the tobacco leaf may be cut. In some embodiments the tobacco leaf may be cut before or after being subjected to curing, fermenting, pasteurising or combinations thereof.

In one embodiment the present invention provides a harvested leaf of a tobacco plant of the invention. In one embodiment the harvested leaf may be obtainable from a tobacco plant which has inhibited diterpene synthesis gene activity or expression and increased sucrose ester content.

In a further embodiment the harvested leaf may be obtainable (e.g. obtained) from a tobacco plant propagated from a propagation material of the present invention. In another embodiment there is provided a harvested leaf obtainable from a method or use of the present invention. Suitably the harvested leaf may be a cut harvested leaf. In some embodiments the harvested leaf may comprise viable tobacco cells. In some embodiments the harvest leaf does not comprise viable tobacco cells. In other embodiments the harvested leaf may be subjected to further processing.

Some tobacco plants may be harvested by cutting the stalks and harvesting all of the leaves simultaneously (e.g. as with burley tobacco). Other tobacco plants (e.g. flue cured tobacco) may be harvested in stages in a process such as priming, wherein individual leaves are removed from the stalk as they ripen.

There is also provided a processed tobacco leaf. The processed tobacco leaf may be obtainable from a tobacco plant of the invention. Suitably the processed tobacco leaf may be obtainable from a tobacco plant obtained in accordance with any of the methods and/or uses of the present invention. In one embodiment the processed tobacco leaf may be obtainable from a tobacco plant which has inhibited diterpene synthesis gene activity or expression and increased sucrose ester content preferably when compared to a control leaf i.e. compared to a leaf from a tobacco plant which has not been modified according to the invention. The processed tobacco leaf may comprise a reduction in diterpene synthesis gene activity or expression and increased sucrose ester content.

In another embodiment the processed tobacco leaf may be obtainable from a tobacco plant propagated from a tobacco plant propagation material according to the present invention. The processed tobacco leaf of the present invention is obtainable by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising. Suitably the processed tobacco leaf may be processed by curing. Tobacco leaf may be cured by any method known in the art. In one embodiment tobacco leaf may be cured by one or more of the curing methods selected from the group consisting of: air curing, fire curing, flue curing and sun curing. Suitably the tobacco leaf may be air cured. Suitably the tobacco leaf may be flue cured.

In one embodiment the processed leaf according to the present invention comprises increased sucrose ester content compared with a comparable product (e.g. processed leaf) which has not been modified in accordance with the present invention.

In one aspect, an air cured leaf according to the present invention comprises increased sucrose ester content compared with a comparable product (e.g. air cured leaf) which has not been modified in accordance with the present invention.

Suitably, the sucrose ester content may be measured in the lower 1/3 leaves of stalk cut air cured plants. Suitably, the sucrose ester content may be measured in the middle 1/3 leaves of stalk cut air cured plants. Suitably, the sucrose ester content may be measured in the upper 1/3 leaves of stalk cut air cured plants.

"Lower leaves" as used herein refers to leaves in the lower third of the plant (for example leaves closest to the base of the plant), "Upper leaves" as used herein refers to leaves in the upper third of the plant (for example leaves furthest away from the base of the plant). "Middle leaves" as used herein refers to the central third of the plant between the lower and upper positions (for example leaves half way between the lower and upper leaves.

Suitably, the lower 1/3 of leaves of stalk cut air cured plants according to the present invention may comprise increased sucrose ester content compared with a comparable product (e.g. the lower 1/3 of leaves of stalk cut air cured plants) which has not been modified in accordance with the present invention. Suitably, the middle 1/3 of leaves of stalk cut air cured plants according to the present invention may comprise increased sucrose ester content compared with a comparable product (e.g. the middle 1/3 of leaves of stalk cut air cured plants) which has not been modified in accordance with the present invention. Suitably, the upper 1/3 of leaves of stalk cut air cured plants according to the present invention may comprise increased sucrose ester content compared with a comparable product (e.g. the upper 1/3 of leaves of stalk cut air cured plants) which has not been modified in accordance with the present invention.

In one aspect a flue cured leaf according to the present invention comprises increased sucrose ester content compared with a comparable product (e.g. flue cured leaf) which has not been modified in accordance with the present invention.

Suitably, the sucrose ester content may be measured in the first priming of flue cured plants. Suitably, the sucrose ester content may be measured in the second (or alternatively the middle) priming of flue cured plants. Suitably, the sucrose ester content may be measured in the third (or alternatively the final) priming of flue cured plants.

As used herein "priming" refers to the removal of leaves from tobacco plants. This may refer to the removal of mature or ripe leaves of flue cured plants.

"First priming" as used herein refers to leaves which are harvested from the tobacco plant first (e.g. leaves from the lowest part of the tobacco plant). The "second (or middle) priming" as used herein refers to leaves which are harvested from the tobacco plant after the initial priming (e.g. leaves from the middle part of the tobacco plant). The "third (or final) priming" as used herein refers to leaves which are harvested last from the tobacco plant (e.g. leaves from the top part of the tobacco plant).

Suitably, the first priming of leaves of flue cured plants according to the present invention may comprise increased sucrose ester content compared with a comparable product (e.g. the first priming of leaves of flue cured plants) which has not been modified in accordance with the present invention. Suitably, the second (or middle) priming of leaves of flue cured plants according to the present invention may comprise increased sucrose ester content compared with a comparable product (e.g. the second (or middle) priming of leaves of flue cured plants) which has not been modified in accordance with the present invention. Suitably, the third (or final) priming of leaves of flue cured plants according to the present invention may comprise increased sucrose ester content compared with a comparable product (e.g the third (or final) priming of leaves of flue cured plants) which has not been modified in accordance with the present invention.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smoulder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting. Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco product, most preferably snus. Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden. Tobacco Control (2003) 12:349-359, the teaching of which is incorporated herein by reference.

During the production of snus pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention, or from a tobacco cell culture according to the present invention.

In another aspect, the present invention provides a tobacco blend comprising tobacco material made from a tobacco plant or part thereof according to the present invention, or from a tobacco cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell culture according to the present invention. Suitably, the tobacco blend may comprise approximately 10% tobacco from a tobacco plant or part thereof according to the present invention, or from a tobacco cell culture according to the present invention. Suitably, the tobacco blend may comprise approximately 20% tobacco from a tobacco plant or part thereof according to the present invention, or from a tobacco cell culture according to the present invention. Suitably, the tobacco blend may comprise approximately 30% tobacco from a tobacco plant or part thereof according to the present invention, or from a tobacco cell culture according to the present invention. Suitably, the tobacco blend may comprise approximately 40% tobacco from a tobacco plant or part thereof according to the present invention, or from a tobacco cell culture according to the present invention. Suitably, the tobacco blend may comprise approximately 50% tobacco from a tobacco plant or part thereof according to the present invention, or from a tobacco cell culture according to the present invention. Suitably, the tobacco blend may comprise approximately 60% tobacco from a tobacco plant or part thereof according to the present invention, or from a tobacco cell culture according to the present invention. Suitably, the tobacco blend may comprise approximately 70% tobacco from a tobacco plant or part thereof according to the present invention, or from a tobacco cell culture according to the present invention. Suitably, the tobacco blend may comprise approximately 80% tobacco from a tobacco plant or part thereof according to the present invention, or from a tobacco cell culture according to the present invention. Suitably, the tobacco blend may comprise approximately 90% tobacco from a tobacco plant or part thereof according to the present invention, or from a tobacco cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell culture according to the present invention.

Suitably the cured tobacco material may be air cured. Suitably the cured tobacco material may be flue cured. Suitably the cured tobacco material may be sun cured.

A tobacco product or smoking article according to the present invention may comprise the tobacco material (e.g. cured tobacco material) according to the present invention.

In another aspect the present invention provides a tobacco product. A tobacco product according to the present invention may be a blended tobacco product. In one embodiment the tobacco product may be prepared from a tobacco plant of the invention or a part thereof. In one embodiment the tobacco product may be prepared from a tobacco plant which has inhibited diterpene synthesis gene activity or expression and increased sucrose ester content. The tobacco product may comprise a reduction diterpene synthesis gene activity or expression and increased sucrose ester content. Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco product may be prepared from a harvested leaf of the invention. In a further embodiment the tobacco product may be prepared from a processed tobacco leaf of the invention. Suitably the tobacco product may be prepared from a tobacco leaf processed by one or more of: curing, fermenting and/or pasteurising. Suitably the tobacco product may comprise a cut tobacco leaf, optionally processed as per the foregoing embodiment.

In one embodiment the tobacco product may be a smoking article. As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco product may be a smokeless tobacco product. The term "smokeless tobacco product" as used herein refers to a tobacco product that is not intended to be smoked and/or subjected to combustion. In one embodiment a smokeless tobacco product may include snus, snuff, chewing tobacco or the like.

In a further embodiment the tobacco product may be a tobacco heating device or hybrid device or e-cigarettes or the like. Typically in heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device. Suitably the tobacco heating device may be an aerosol-generating device.

Preferably the tobacco heating device may be a heat-not-burn device. Heat-not-burn devices are known in the art and release compounds by heating, but not burning, tobacco. An example of a suitable, heat-not-burn device may be one taught in WO2013/034459 or GB2515502 which are incorporated herein by reference.

In one embodiment the aerosol-forming substrate of a tobacco heating device may be a tobacco product in accordance with the present invention.

In one embodiment the tobacco heating device may be a hybrid device.
Polynucleotides/Polypeptides/Constructs In certain embodiments of the present invention, constructs which inhibit activity or expression of a diterpene synthesis gene may be transformed into plant cells under the direction of a promoter.

In certain embodiments of the present invention, ddRNAi DNA constructs which express dsRNA or amiRNA to inhibit activity or expression of a diterpene synthesis gene may be transformed into plant cells under the direction of a promoter.

Constructs may be introduced into plants according to the present invention by means of suitable vector, e.g. plant transformation vectors. A plant transformation vector may comprise an expression cassette comprising 5'-3' in the direction of transcription, a promoter sequence, a ddRNAi DNA construct sequence targeting a diterpene synthesis gene, preferably targeting cyclase 2 gene (CYC2), CBTol cyclase or terpene synthase 3-8, optionally including introns, and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application No. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest (e.g. the gene the promoter is going to direct, for instance a gene encoding a deregulated nitrate reductase of the invention) coding sequence used in the present invention or may be derived from a different gene, from *Nicotiana tabacum*, or another organism, for example from a plant of the family Solanaceae, or from the subfamily Cestroideae.

The expression cassette may be incorporated into a basic plant transformation vector, such as pBIN 19 Plus, pBI 101, pKYLX71:3552, pCAMBIA2300 or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "plant transformation vector" means a construct capable of in vivo or in vitro expression. Preferably, the expression vector is incorporated in the genome of the organism. The term "incorporated" preferably covers stable incorporation into the genome.

Techniques for transforming plants are well known within the art and include Agrobacterium- mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christon (AgroFood-Industry Hi-Tech March/April 1994 17-27) which are incorporated herein by reference.

Typically, in *Agrobacterium*-mediated transformation a binary vector carrying a foreign DNA of interest, i.e. a ddRNAi DNA construct, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 Dec;16(6):735-43,which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J.P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994) which is incorporated herein by reference. Production of fertile transgenic maize plants by silicon carbide whisker-mediated transformation is taught in *The Plant Journal* 6: 941-948, which is incorporated herein by reference) and viral transformation techniques is taught in for example Meyer P, Heidmmm I & Niedenhof I (1992). The use of cassava mosaic virus as a vector system for plants is taught in Gene 110: 213-217, which is incorporated herein by reference. Further teachings on plant transformation may be found in EP-A-0449375, incorporated herein by reference.

In a further aspect, the present invention relates to a vector system which carries an ddRNAi DNA construct and introducing it into the genome of an organism, such as a plant. The vector system may comprise one vector, but it may comprise two vectors. In the case of two vectors, the vector system is normally referred to as a binary vector system. Binary vector systems are described in further detail in Gynheung Anetal, (1980), Binary Vectors, *Plant Molecular Biology Manual* A3, 1-19, which is incorporated herein by reference.

One extensively employed system for transformation of plant cells uses the Ti plasmid from *Agrobacterium tumefaciens* or a Ri plasmid from *Agrobacterium rhizogenes* Anetal., (1986), *Plant Physiol.* 81, 301-305 and Butcher D. N. et al., (1980), *Tissue Culture Methods for Plant Pathologists*, eds.: D. S. Ingrams and J.P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema, in: The Binary Plant Vector System Offset-drukkerij Kanters B. B., Amsterdam, 1985, Chapter V; Fraley, et al., *Crit. Rev. Plant Sci.*, 4:1-46; and Anetal., *EMBO J* (1985) 4:277-284, incorporated herein by reference.

Plant cells transformed with a ddRNAi DNA construct which expresses a dsRNA or amiRNA which inhibits activity or expression of a diterpene synthesis gene may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a ddRNAi DNA construct according to the invention. Accordingly a transgenic plant is a plant which has been transformed with a ddRNAi DNA construct according to the invention. Preferably the transgenic plant exhibits inhibited diterpene synthesis gene activity or expression and increased sucrose ester content, according to the present invention. The term "transgenic plant" does not cover native nucleotide coding sequences in their natural environment when they are under the control of their native promoter which is also in its natural environment.

In one aspect, a ddRNAi DNA construct, plant transformation vector or plant cell according to the present invention is in an isolated form. The term "isolated" means that the sequence is at least substantially free from at least one other component with which the sequence is naturally associated in nature and as found in nature.

In one aspect, a ddRNAi DNA construct, plant transformation vector or plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention, i.e. the diterpene synthesis gene, includes the native nucleotide sequence when in its natural environment and when it is linked to its naturally associated sequence(s) that is/are also in its/their natural environment. For ease of reference, we shall call this preferred embodiment the "native nucleotide sequence". In this regard, the term "native nucleotide sequence" means an entire nucleotide sequence that is in its native environment and when operatively linked to an entire promoter with which it is naturally associated, which promoter is also in its native environment.

Typically, the RNAi molecule encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232 which are incorporated herein by reference).

A nucleotide sequence encoding either a protein which has the specific properties as a diterpene synthesis gene as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869 which is incorporated herein by reference, or the method described by Matthes et al., (1984) *EMBO J.* 3, p 801-805 which is incorporated herein by reference. In the phosphoroamidite method, oligonucleotides are synthesised, e.g. in an automatic DNA synthesiser, purified, annealed, ligated and cloned in appropriate vectors.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The present invention also encompasses the use of sequences having a degree of sequence identity or sequence homology with amino acid sequence(s) of a polypeptide having the specific properties defined herein or of any nucleotide sequence i.e. diterpene synthesis gene encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the diterpene synthesis gene. Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

Homology or identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana©ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides; wherein the nucleotide sequence encodes a ddRNAi DNA construct. The degree of identity with regard to a nucleotide sequence is determined over at least 10 contiguous nucleotides, preferably 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)⁴, L-Tyr (methyl)*, L-Phe (4-isopropyl)*, L-Tic (1,2,3,4-tetrahydroisoquinoline-3-carboxyl acid)*, L-diaminopropionic acid* and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein). Preferably, hybridisation is determined under stringency conditions (e.g. 50° C. and 0.2×SSC {1×SSC=0.15 M NaCl, 0.015 M Na₃citrate pH 7.0}). More preferably, hybridisation is determined under high stringency conditions (e.g. 65° C. and 0.1×SSC {1×SSC =0.15 M NaCl, 0.015 M Na₃citrate pH 7.0}).

In one aspect the sequence for use in the present invention is a synthetic sequence—i.e. a sequence that has been prepared by in vitro chemical or enzymatic synthesis. It includes, but is not limited to, sequences made with optimal codon usage for host organisms.

The term "expression vector" means a construct capable of in vivo or in vitro expression. In one embodiment the vector of the present invention expresses a dsRNA. In one embodiment the vector of the present invention expresses an amiRNA. Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism. The ddRNAi DNA constructs for use in the present invention may be transformed into a suitable host cell as described herein to provide for expression of a polypeptide of the present invention. The choice of vector e.g. a plasmid, cosmid, or phage vector will often depend on the host cell into which it is to be introduced. Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector. The vector may further comprise a nucleotide sequence enabling the vector to replicate in the host cell in question. Examples of such sequences are the origins of replication of plasmids pUC19, pACYC177, pUB110, pE194, pAMB1 and pIJ702.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals. The term "promoter" is used in the normal sense of the art, e.g. an RNA polymerase binding site. The nucleotide sequence within a ddRNAi DNA construct which encodes a dsRNA or amiRNA may be operably linked to at least a promoter.

The term "construct"—which is synonymous with terms such as "cassette" or "vector"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The ddRNAi DNA construct may even contain or express a marker, which allows for the selection of the genetic construct.

A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27), which is incorporated herein by reference. Further teachings on plant transformation may be found in EP-A-0449375, incorporated herein by reference.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Advantages

Advantageously the inhibition of activity or expression of a diterpene synthesis gene increases the sucrose ester content of tobacco plants. Without wishing to be bound by theory, reduced carbon utilization to make diterpenes is believed to result in enhanced sucrose ester production. Advantageously methods of the present invention allow the production of tobacco plants with a preferred "Turkish-like" chemistry which are high biomass plants. Advantageously the invention provides desirable smoke chemistry and chemistries useful for heat-not-burn products. The invention will now be described, by way of example only, with reference to the following Figures and Examples.

EXAMPLES

Example 1

Preparation of Transgenic Constructs, GW1, GW2, GW3, GW5

The inventors sought to dissect plant trichome secondary metabolism and to assess the affect of trichome-expressed genes on sucrose ester content using posttranscriptional gene silencing strategies (PTGS). The functions of cyclase 2 gene (CYC2), CBTol cyclase and terpene synthase 3-8 were assessed using RNAi. Methods for construct preparation and plant regeneration are given in details in Wang and Wagner 2003 (supra which is incorporated herein by reference) along with conventional molecular cloning techniques (Sambrook et al. 1989 Molecular cloning: a laboratory manual, Cold Spring Harbor Laboratory Press, New York).

Transgenic Construct GW1—Inhibits Expression of the Cyclase 2 Gene (CYC2)

This ddRNAi DNA construct was designed on the basis of the cyclase 2 gene (CYC2). The complete coding sequence of mRNA of CYC2 is annotated as AF401234. The genomic sequence is annotated as AY495694. The construct used to create GW1 plants consists of: 5'-sense fragment from 54th to 716th nucleotide from the sequence AF401234; partial GUS A fragment as a hairpin loop (from 787th to the 1812th nucleotide) the GUS A annotation is AF502128; and the reverse complement of the CYC2 sense fragment-3'. The construct comprises nucleotides 54 to 716 from CYC2 mRNA (AF401234) in sense orientation. This sequence corresponds to nucleotide positions from the genomic sequence (AY495694): nucleotides 1 to 25, nucleotides 26 to 271 (exon 1), nucleotides 1253 to 1529 (exon 2) and the first 115 nucleotides of the 3rd exon (nucleotides 2366 to 2480). The plasmid pKYLX71-3552 was the binary vector used for the gene construct (Wang et al. 2001 supra which is incorporated herein by reference). The sequence of the GW1 construct insert is set forth in SEQ ID No. 5.

Transgenic Construct GW2—Inhibits Expression of the Terpene Synthase 3-8 Gene

This ddRNAi DNA construct was designed on the basis of miRNA168 primary transcript (EU549055.1; GI: 171195398) (from 5'127-to 535-3'), where 196-216 were substituted with 21 nucleotides from nucleotide 1497 in reverse complement to the original sequence (Genbank: AY528645, corresponding to nucleotide positions as shown in SEQ ID NO. 3), and nucleotides 279-299 were substituted with the 21 nucleotides from the original chain in forward orientation, but where 3 bases were modified when the area 1497-1517 was used. The module flanked by 5'-HindIII, and 3'-EcoRI restriction sites extension was inserted between the 2×35S promoter and the 35S terminator. The extended module that contained the 2×35S prom- miRNAi 3-8 and 35S terminator was introduced into the multiple cloning site (MCS) of binary vector pCAMBIA2300. The recombinant vector (KmR) was inserted into *A. tumefaciens*, GV3101 (RifR, GmR). Colonies were selected on triple antibiotic (Km, Rif, Gen). *Agrobacterium* transformation was confirmed by plasmid PCR. The sequence of the GW2 construct insert is set forth in SEQ ID No. 7.

Transgenic Construct GW3—Inhibits Expression of the CBTol Cyclase Gene

This ddRNAi DNA construct was designed on the basis of *N. tabacum* cyclase gene (AY049090). This double stranded RNAi module was assembled the following way:—a partial sequence from *N. tabacum* cyclase gene (AY049090), from 5' 2854 to 4175-3' of SEQ ID No. 1 in forward and reverse orientation, consisting of partial exon 4, complete intron 4, exon 5, intron 5, exon 6, intron 6, and partial exon 7. The spacer between the forward and reverse stretches was a partial GUS A gene, from 5'-786-1816-3'. The plasmid pCAMBIA2300 was the binary vector used for this gene construct. The sequence of the GW3 construct insert is set forth in SEQ ID No. 6.

Transgenic Construct GW5—Inhibits Expression of the Terpene Synthase 3-8 Gene

This ddRNAi DNA construct was designed on the basis of miRNA168 primary transcript (EU549055.1; GI: 171195398) (from 5'127-to 535-3'), where 196-216 were substituted with 21 nucleotides from nucleotide 884 in reverse complement to the original sequence (Genbank: AY528645, corresponding to nucleotide positions as shown in SEQ ID NO. 3), and nucleotides 279-299 were substituted with the 21 nucleotides from the original chain in forward orientation, but where 4 bases of the sense chain were modified when the area 884-904 was used. The module flanked by 5'-HindIII, and 3'-EcoRI restriction sites extension was inserted between the 2×35S promoter and the 35S terminator. The extended module that contained the 2×35S prom-miRNAi 3-8 and 35S terminator was introduced into the multiple cloning site (MCS) of binary vector pCAMBIA2300. The recombinant vector (KmR) was inserted into *A. tumefaciens*, GV3101 (RifR, GmR). Colonies were selected on triple antibiotic (Km, Rif, Gen). *Agrobacterium* transformation was confirmed by plasmid PCR. The sequence of the GW5 construct insert is set forth in SEQ ID No. 11.

Example 2

Agro-Transformation and Regeneration of T.I. 1068

*N. tabacum* T.I. 1068 seeds were obtained from the KTRDC seed collection and surface sterilized with 70% EtOH for 1 min, then 5% (v/v) Chlorox, and then washed three times with sterile water. Plants were grown in vitro in PLANTCON® containers (MP Biomedicals, LLC), and used as a stock of explants for transformation. All constructs were introduced into tobacco cultivar T.I. 1068 by *Agrobacterium*-mediated transformation and the presence of transgenes was confirmed by PCR. *A. tumefaciens* transformation was done essentially as described by Horsch et al. in Horsch R B, Fry J E, Hoffmann N L, Eichholtz D, Rogers S G, Fraley R T (1985) Science 227:1229-1231 which is incorporated herein by reference with some modifications. *Agrobacterium* was grown over night on LB medium, containing 50 mg/l Km, 50 mg/l Rif and 35 mg/l Gm (GW1, GW2,). For GW3, Km was replaced by Hyg (55 mg/l).

Cut leaf pieces (1 cm$^2$) from sterile-grown plants (45 days old) were inoculated with the bacteria (1×10$^8$ cfu/ml) for 2 days in the dark, than blotted dry and transferred to MS medium supplemented with Gamborg B-5 vitamins (Sigma-Aldrich Co. LTD, Irvine, UK), 3% Sucrose, 1 mg/l BAP and 0.05 mg/l NAA supplemented with 200 mg/l Km (or 55 mg/l Hyg for GW3) and 400 mg/l Cefotaxim. After about a month, small plantlets were formed at the edges of pieces and after one passage on the same medium, the plantlets were transferred to the same medium, but hormones were removed, and antibiotics were reduced by half. Rooted plants were transferred to fertilized Pro- Mix (Premier Horticulture Inc., Canada) in the growth room. Individual transformants were analysed via GC-MS, and those with desirable changes were self-seeded for further analysis of T1 generation.

Example 3

Green Leaf Analysis of Field Drown Control Versus Transgenic Lines

Preparation of Lines for Field Test and Field Test Design

Seeds from lines GW1 and GW2, generated from self-pollination of T3, or T2 plants, were surface sterilized and germinated in vitro on MS medium supplemented with Gamborg B-5 vitamins (Sigma-Aldrich Co. LTD, Irvine, UK), 3% Sucrose, and Km (200 mg/l). GW3 seeds were surface sterilized and germinated on medium contained Hyg (55 mg/l). After a month, plantlets were transferred to float trays in a green house (fertilized Pro-Mix (Premier Horticulture Inc., Canada) and grown for 7-8 weeks before transplanting to the field. Standard field practices were used and irrigation was used as necessary. Harvesting and collection of flue and air curing (as for Burley) was completed after approximately 4½ months. Flue curing included: 48 hours colouring, 85 to 100° F., 94% RH; 24 hours wilting, 100° F. to 120° F., to 54% RH; 30 hours leaf drying, 120° F. to 135° F., 40% RH; 40 hours stem drying, 135 to 168° F., to 22% RH.

Measurement of Exudate Components as TMS Derivatives by GC-MS

For green leaf measurements, two leaf discs (2 cm diameter) were cut from the middle of the lamina of the middle leaf of each plant. The discs were washed with acetonitrile (5 ml) for 30 seconds. Washes were concentrated via vacuum rotor evaporation to yield oily residue. The residue was derivatized to form tri-methyl silyl (TMS) esters, essentially as described by Severson et al. 1985 (supra which is incorporated herein by reference) as follows: acetonitrile washes were evaporated to dryness, dissolved in 1 ml CHCl$_3$, transferred to 1.5 ml GC vials and dried under a stream of N2 at 40° C. Derivatized samples were dissolved in 1 ml dimethyl formamide (DMF) and 50 µl of BSTFA [bis(trimethylsilyl) trifluoroacetamide] and 24 µg of cembrene as an internal standard cembrene were added to each vial. Samples were derivatized at 70° C. for 45 min, cooled to room temperature and analysed.

The TMS derivatives were separated and analysed by GC-MS (HP6890 GC equipped with HP5973 MS and an automatic sampler injector, using a 30.0 m Agilent capillary column 19091J-413 with 0.25 µm film thickness and 0.25 mm diameter. Helium was the carrier gas with 1.8 ml/min constant flow, and injection temperature of 250° C. The oven program for running TMS ester derivatives was as follows: initial temperature 180° C. for 2.0 min; rate 8° C. per min until 280° C., hold for 9.5 min. Total run time was 24.0 min. Eluted compounds were identified by their retention time and by comparison of MS profiles with standards. The diterpenoids eluted at: cis-abienol to βCBT-diol, 6 to 8 min; diterpenoid oxidation products, 8 to 13.5 min; sucrose esters, 17 to 22.5 min. For component measurement of flue and air cured tissues, 6.14×6.14 cm pieces (the equivalent of 12 leaf discs of green tissues) of typical leaves were cut from dry tissue and washed with acetonitrile. Ten to sixteen replicate samples were prepared per line and control for air and flue cured using the same leaves used for green leaf analysis (leaf punches). The preparation of samples for chemical analysis as TMS derivatives was as described above, and for acyl groups of sucrose esters as below.

The integrated peak areas of all compounds and internal standard were recorded and the relative amount of each one was calculated as % of total. Numerous peaks of sucrose ester types were combined to give a summary peak area.

The mean number of leaves per plant, the green weight of leaves per plant and the total exudate weight per plant of controls versus transgenic lines is presented in Table 1 below. Data are averages of 3 plants of each line, at 19 days post topping. (Topping refers to the removal of the tobacco flowers)

The GC-MS results for constructs GW2 and GW5 (T$_0$), and their T$_1$ and T$_2$ generations were identical; both exhibited very high labdenediol and low CBT-diols and Cis-abienol. To avoid redundancy, field work was carried out using construct GW2 only.

TABLE 1

| Line | Mean number of leaves | Green weight of leaves (Kg) | Total acetonitrile exudate weight (gm) |
| --- | --- | --- | --- |
| Control | 22 | 2.79 | 7.8 |
| GW1 | 20 | 3.23 | 3.1 |
| GW2 | 21 | 3.24 | 4.3 |
| GW3 | 23 | 3.24 | 3.1 |

Table 1 shows that the mean number of leaves per plant, the green weight of leaves per plant were similar in between the transgenic lines tested and were similar to the control plant.

Green Leaf Analysis of Field Grown Control Versus Transgenic Lines

Figure 3:
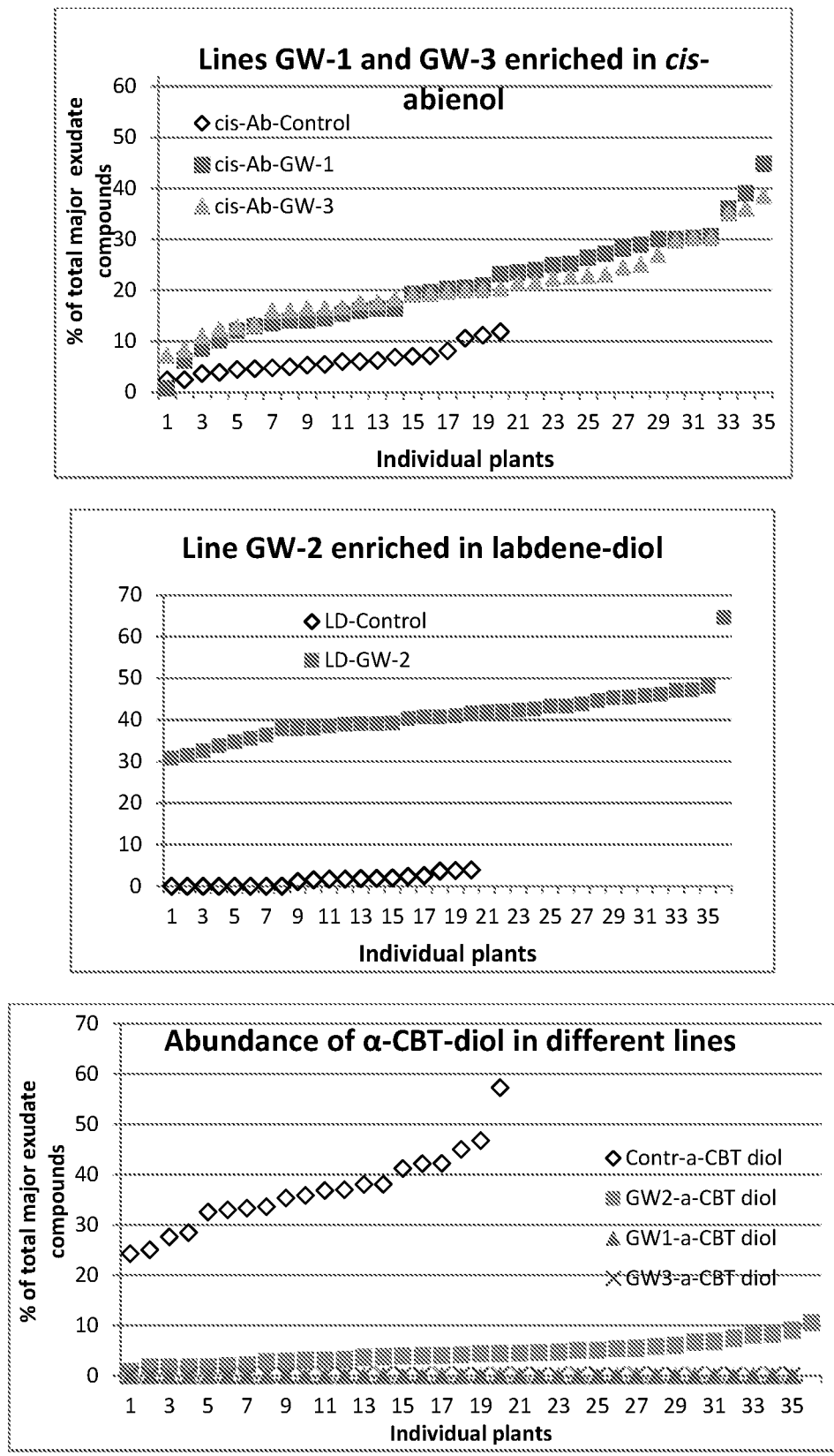
FIG. 3. shows graphs displaying green leaf analyses of field grown control versus transgenic lines. Individual plant chemistries are arranged in ascending order of amount.

Green leaf exudate chemistry analysis was carried out just after topping and showed that for each line exudate chemistry in the field was similar to that observed in plants in the greenhouse, and that plant-to-plant variability in chemistry was about 25-30% for control and each line in the field (see FIG. 3). Each point on the graph represents the data from one plant. The data presented in FIG. 3 show that:

Lines GW1 and GW3 are enriched in cis-abienol
Line GW2 is enriched in labdene-diol Measurement of Sucrose Ester Acyl Composition The methods used are modified from Severson et al. 1985 (supra which is incorporated herein by reference). To 5 to 10 mg of gum samples in a 30 ml Corex glass tube, 0.5 ml KOH (1 M) in 80%

MeOH is added and let stand overnight at 22° C. to saponify. Samples were then dried under N$_2$ followed by addition of 1 ml n-BuOH and 3 drops conc. H$_2$SO$_4$. The samples were then heated at 110° C. for 1 hour after which components are partitioned between hexane and water (1.5 ml each) using a pulsed vortex mixer (10 pulses, 1.5 seconds each). Six to seven extractions were made (until the water phase was neutral to litmus paper). The water phase contains the $K_2SO_4$, $H_2SO_4$ and sugars and the hexane phase the butyl esters of the acyl groups. The hexane is transferred to a 1.5 ml GC vial and analysed by GC-MS using the same column and as for TMS. Helium was the carrier gas with 1.8 ml/min constant flow, and injection temperature of 250° C. The oven program for running butyl ester derivatives was as follows: initial temperature 90° C. for 3.0 min; rate 3° C. per min until 160° C., hold for 2 min, rate 15° C. per minute to 250° C., hold 5 min. Total run time was 39.33 min.

Figure 4:
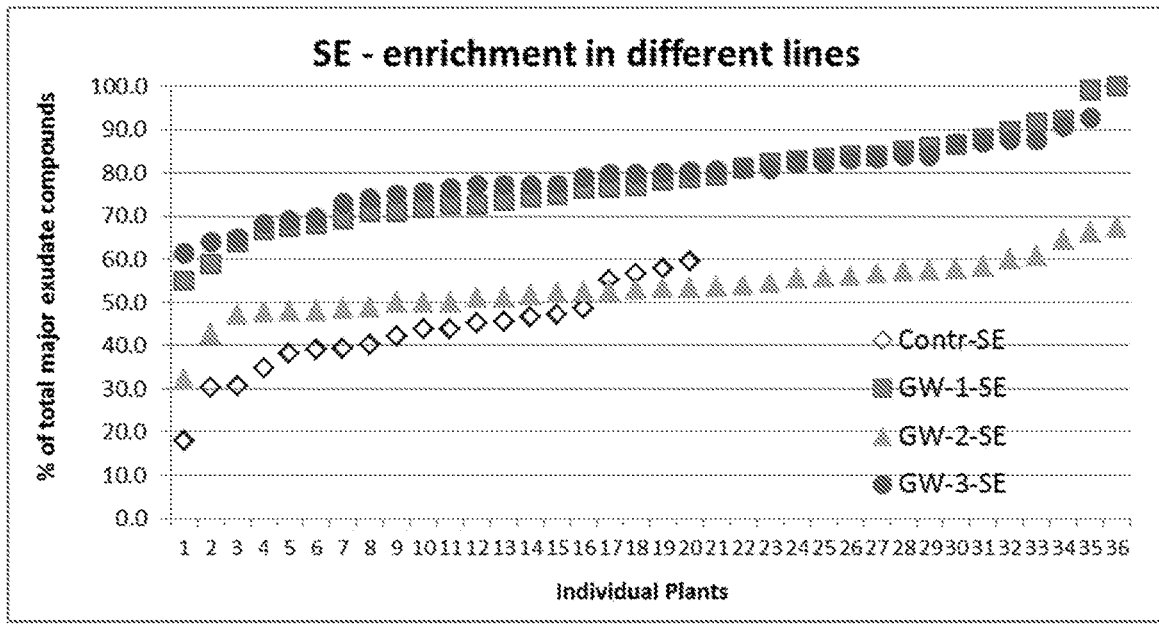
FIG. 4. shows a graph displaying the total sucrose ester content in control versus transgenic lines.

The data in FIG. 4 clearly show that lines GW1 and GW3 (which comprise high cis-abienol) also exhibit enhanced sucrose ester yield when compared to the control. Each point on the graph represents the data from one plant. Acyl composition was unchanged, therefore these lines are similar to Turkish or Oriental tobacco in that high levels of cis-abienol and high 3-methyl valeric acid precursor are present but advantageously, they are produced by a relatively high biomass plant.

FIG. 4 shows that:
In the high cis-abienol lines (GW1 and GW3) sucrose esters were greatly enriched versus control.
In the GW2 line (high labdenediol) sucrose esters were also elevated.

Example 4

Exudate Components in Green vs Flue Cured Field Tobaccos and Green vs Air Cured Tobaccos RNAi lines were grown in the field, T2 or T3, trait stable. Harvesting and collection of flue and air curing (as for Burley) was completed after approximately 4 and a half months. Flue curing included: 48 hours colouring, 85 to 100° F., 94% RH; 24 hours wilting, 100° F. to 120° F., to 54% RH; 30 hours leaf drying, 120° F. to 135° F., 40% RH; 40 hours stem drying, 135 to 168° F., to 22% RH, as described in Example 3.

The same TMS chromatograms, which were generated for FIGS. 3 and 4, were used to recalculate exudate component on the basis of surface area, expressed as $\mu g/cm^2$ in Tables 2 and 3 (green vs. flue and green vs. air). The calculation was on the basis of comparison with the known amount of the internal standard cembrene, with the assumption that the peak response is identical for all compounds. The compound amounts shown in Table 2 present an average of 20 green, plants for the control, and 34 to 36 green plants and 10 to 14 cured plants for lines GW1- 3, ±their respective standard deviations.

TABLE 2

Exudate components in Green vs Flue cured 2014 field tobaccos

| Line | Type | cis-Abienol | α-CBT-ols | β-CBT-ols | ug/cm² LD | α-diols | β-diols | SEs | Oxidized |
|---|---|---|---|---|---|---|---|---|---|
| control | Green(20) | 6.695 | 1.278 | | 2.570 | 38.301 | 12.585 | 48.091 | 44.150 |
| | ± | 3.534 | 1.155 | | 1.563 | 16.275 | 7.219 | 23.489 | 28.506 |
| | Flue(16) | 0.926 | | | 3.003 | 27.916 | 14.986 | 43.338 | 92.269 |
| | ± | 0.534 | | | 1.319 | 16.893 | 5.178 | 28.781 | 52.600 |
| | | −7.2x | | | ≈ | −1.4x | ≈ | ≈ | +2.1x |
| GW-1 | Green(36) | 6.888 | | | 0.531 | | | 26.781 | 2.642 |
| | ± | 5.297 | | | 0.534 | | | 17.317 | 2.759 |
| | Flue(14) | 0.749 | | | 4.752 | | | 77.889 | 23.832 |
| | ± | 0.785 | | | 3.220 | | | 36.421 | 20.537 |
| | | −9.2x | | | +8.9x | | | +2.9x | +9.0x |
| GW-2 | Green(36) | 0.238* | | | 25.246 | 2.946 | 0.679 | 33.272 | 10.168 |
| | ± | | | | 5.775 | 1.992 | 0.745 | 12.424 | 4.373 |
| | Flue(10) | 0.434 | | | 56.168 | 11.382 | 6.342 | 87.204 | 44.746 |
| | ± | 0.210 | | | 19.280 | 6.689 | 3.231 | 43.586 | 29.784 |
| | | +1.8x | | | +2.2x | +3.9x | +9.3x | +2.6x | +4.4x |
| GW-3 | Green(36) | 6.506 | | | 0.214 | | | 25.491 | 3.029 |
| | ± | 2.800 | | | 0.369 | | | 10.148 | 1.775 |
| | Flue(14) | 0.926 | | | 6.136 | | | 118.551 | 39.462 |
| | ± | 1.101 | | | 3.711 | | | 50.448 | 26.053 |
| | | −7x | | | +28.7x | | | +4.7x | +13.0x |

*Abundance of cis-abienol from 2 leaf disc extract was low.
The numbers are calculated from the % of total green leaf extract.
** abundance of a-and b-CBT-diols from 2 leaf discs-green was low.
Here the numbers are calculated from the % of total green leaf extract.

The data presented in Table 2 show that flue curing does not increase sucrose ester exudate component of control plants but it does increase the sucrose ester content of transgenic plants comprising construct GW1, GW2 or GW3. Flue curing also increased the LD content of transgenic plants comprising construct GW1, GW2 or GW3. Flue curing increased the cis-abienol content of all tobaccos.

The data shows that flue curing increases the α-CBT-diol content of the exudate component of GW2 transgenic plants compared to green tobacco. The α-CBT-diol content of control plants is also increased by flue curing but to a lesser extent. The data also show that flue curing increases the β-CBT-diol content of the exudate component of GW2 transgenic plants compared to green tobacco. The β-CBT-diol content of control plants is not affected by flue curing.

Oxidation products were increased in the transgenic lines.

The compound amounts shown in Table 3 (below) present an average of 20 green, plants for the control, and 34 to 36 green plants and 8 to 16 cured plants for lines GW1-3, ±their respective standard deviations.

The data presented in Table 3 below show that air curing does not increase sucrose ester exudate component of control plants but it does slightly increase the sucrose ester content of transgenic plants comprising construct GW1, GW2 or GW3. Sucrose ester content is stable in the transgenic lines with air curing. The data also show that flue curing increases the α-CBT-diol content (which is a minor component in transgenics) of the exudate component of GW2 transgenic plants compared to green tobacco. The α-CBT-diol content of control plants is not affected by flue curing.

The data shows that air curing increases the β-CBT-diol content of the exudate component of GW2 transgenic plants compared to green tobacco. The β-CBT-diol content of control plants is also increased by flue curing but to a lesser extent. Air curing also increased the LD content of transgenic plants comprising construct GW1, GW2 or GW3. Air curing increased the cis-abienol content of the control and of tobaccos comprising the GW1, or GW3.

Oxidation products increased in the transgenic lines.

inventors compared diterpenoid and sucrose ester composition in the transgenic lines with a control T.I. 1068 and with sun cured Turkish type commercial tobaccos. Sun dried commercial tobaccos were sent to the inventors as pressed leaf. The data presented for the transgenic tobacco lines present an average of between 10 and 14 plants whilst the T.I. 1068 control presents the average over 16 plants.

The following commercial Turkish types were analysed for comparison:

A=Oriental, Supplier: Socotab EOOD, Crop 2013
B=Turkey-Samsun Crop 2013, Grade SMAL
C=Turkey-IXM IR, Crop 2013, Grade YZAL See Table 4 Exudate composition analysis of diterpenoid contents.

The data in Table 4 (below) show the flue-cured transgenic lines GW1, GW2 and GW3 have higher sucrose ester contents compared with the control and/or Turkish plants tested.

See Table 5 Exudate composition analysis of sucrose ester acyl group composition.

TABLE 3

Exudate components in Green vs Air cured 2014 field tobaccos

| Line |  | cis-Abienol | α-CBT-ols | β-CBT-ols | ug/cm² LD | α-diols | β-diols | SEs | Oxidized |
|---|---|---|---|---|---|---|---|---|---|
| control |  | 6.695 |  |  | 2.570 | 38.301 | 12.585 | 48.091 | 44.150 |
|  | ± | 3.834 | 1.155 |  | 1.563 | 16.275 | 7.219 | 23.489 | 28.506 |
|  | Air(3) | 2.374 |  |  | 3.017 | 42.958 | 20.887 | 45.557 | 107.589 |
|  | ± | 0.706 |  |  | 0.443 | 13.155 | 6.276 | 12.058 | 30.220 |
|  |  | −2.8x |  |  | ≈ | ≈ | +1.7x | ≈ | +2.4x |
| GW-1 | Green(36) | 6.888 |  |  | 0.531 |  |  | 26.781 | 2.642 |
|  | ± | 8.097 |  |  | 0.594 |  |  | 17.317 | 2.759 |
|  | Air(10) | 4.702 |  |  | 2.210 |  |  | 43.867 | 17.238 |
|  | ± | 4.469 |  |  | 1.767 |  |  | 28.072 | 12.611 |
|  |  | −1.5x |  |  | +4.2x |  |  | +1.6x | +6.5x |
| GW-2 | Green(36) | 0.238* |  |  | 25.246 | 2.946 | 0.679 | 33.272 | 10.168 |
|  | ± |  |  |  | 6.775 | 1.982 | 0.748 | 12.424 | 4.373 |
|  | Air(8) | 0.271 |  |  | 32.983 | 8.594 | 4.151 | 50.554 | 25.741 |
|  | ± | 0.111 |  |  | 10.964 | 2.749 | 1.338 | 24.498 | 10.325 |
|  |  | ≈ |  |  | +1.3x | +2.9 | +6.1x | +1.5x | +2.6x |
| GW-3 | Green(36) | 6.506 |  |  | 0.214 |  |  | 25.491 | 3.029 |
|  | ± | 2.800 |  |  | 0.359 |  |  | 10.148 | 1.775 |
|  | Air 11( ) | 2.736 |  |  | 1.712 |  |  | 33.185 | 15.565 |
|  |  | 1.798 |  |  | 0.7 |  |  | 15.1 | 8.7 |
|  |  | −2.4x |  |  | +8.0x |  |  | +1.5x | +5.1x |

*Abundance of cis-abienol from 2 leaf disc extract was low.
The numbers are calculated from the % of total green leaf extract.
** Abundance of a-and b-CBT-diols from 2 leaf discs-green was low.
The numbers are calculated from the % of total green leaf extract.

Example 5

Analyses of Diterpenoid Composition and Acyl Composition of Sucrose Ester

Diterpenoid composition and sucrose ester acyl composition were measured as described in Example 3. The data presented for the transgenic tobacco lines present an average of between 4 and 8 plants whilst the T.I. 1068 control presents the average over 10 plants. The data in Table 5 (below) show that the sucrose ester acyl composition of the transgenic tobacco lines GW1, GW2 and GW3 is similar to the Turkish-type tobacco composition i.e. is rich in 3-Me valeric acyl groups.

TABLE 4

Exudate composition analysis of diterpenoid contents

| | | % of total exudate content | | | | | | | |
|---|---|---|---|---|---|---|---|---|---|
| | | cis-abienol | α-CBT-diols | β-CBT-diols | ID | Oxidized | SE | α-CBT-ols | β-CBT-ols |
| 5 mg | Turkish A sun-cured | — | 5.7 | 3.2 | — | 77.2 | 14.0 | — | — |
| 5 mg | Turkish B sun-cured | — | 4.3 | 2.3 | — | 81.1 | 12.3 | — | — |
| 5 mg | Turkish C sun cured | — | 10.4 | 6.0 | — | 68.5 | 15.0 | — | — |
| | Turkish Average | — | 6.8 | 3.8 | — | 75.6 | 13.8 | — | — |
| 12 I.d. aver of 16 pl. | 1068, flue-cured | 0.5 | 15.3 | 8.2 | 1.6 | 50.6 | 23.7 | — | — |
| 12 l.d. aver of 14 pl. | GW-1, flue-cured | 0.7 | — | — | 4.4 | 22.3 | 74.0 | — | — |
| 12 I.d. aver of 10 pl. | GW-2, flue-cured | 0.2 | 5.5 | 3.1 | 27.2 | 21.7 | 42.3 | — | — |
| 12 I.d. aver of 14 pl. | GW-3, flue-cured | 0.6 | — | — | 3.7 | 24.1 | 71.6 | — | — |

TABLE 5

Exudate composition analysis of sucrose ester acyl group composition

| | | % of total acyl groups | | | | | | |
|---|---|---|---|---|---|---|---|---|
| | | 2-mPro | C4 | 2-mB | 3-mB | 3-mV | 4-mV | Acet |
| 3.8 mg | 1068-total extract | 3.8 | tr | 9.6 | 9.4 | 67.6 | tr | 9.6 |
| 2I.d. | 1069-aver. 12 plants* | 3.7 | 35 | 11.4 | 17.4 | 53.4 | | 10.4 |
| 3.6 mg | high LD, GH(GW2) | 3.3 | 1 | 9.3 | 20.3 | 56.4 | 2.2 | 7.6 |
| 4.1 mg | cyc9 (GW1) | 4 | 0.8 | 12.3 | 16.5 | 57 | 1.8 | 7.6 |
| 4 I.d. | cyc3intr-22-6-17 | 4.6 | tr | 14.6 | 18.7 | 53.1 | tr | 9.1 |
| 3.7 mg | 101-5-2(mono-ols) | 3.1 | 1.2 | 13.9 | 12.2 | 60.8 | tr | 8.9 |
| 6 mg | turkish A sun-cured | 1.8 | 1.1 | 12.4 | 16.4 | 59.6 | 1.0 | 7.7 |
| 6 mg | turkish B sun-cured | 2.2 | 1.7 | 16.7 | 11.9 | 55.8 | 1.0 | 10.8 |
| 6 mg | turkish C sun-cured | 2 | 1.2 | 11.5 | 12.5 | 63.2 | 1.0 | 8.6 |
| 8I.d. | maduro1 | 1.5 | 3.3 | 10.3 | 12.5 | 60.7 | 0.6 | 11.0 |
| 8I.d. | maduro 25 | 3.6 | 4.3 | 11 | 14.8 | 46.3 | 0.0 | 20.1 |
| 10 I.d., 5 plants | 1068, contr air cured | 1.9 | 1 | 7.1 | 16 | 63 | 2.1 | 8.9 |
| 11 I.d., 5 plants | 1068, GW1 air cured | 3.5 | 1 | 6.3 | 26.6 | 53.4 | 2.8 | 6.5 |
| 12 I.d., 5 plants | 1068, GW2 air cured | 2.1 | 0.8 | 6.4 | 22.4 | 57.9 | 3.0 | 7.4 |
| 13 I.d., 5 plants | 1068, GW3 air cured | 3.1 | 1 | 5.8 | 27.2 | 52.7 | 2.5 | 7.7 |
| 14 I.d., 5 plants | 1068, GW4 air cured | 2.1 | 1.4 | 7.4 | 14.7 | 64.3 | 2.0 | 8.2 |
| 15 I.d., 5 plants | 1068, GW1flue-cured | 2.6 | 0.8 | 5.8 | 24.1 | 54.5 | 2.0 | 10.2 |
| 16 I.d., 5 plants | 1068, GW3flue-cured | 2.6 | 0.9 | 7.4 | 24.4 | 55.9 | 2.0 | 6.8 |

Example 6

GW3 Surface Chemistry Analysis

Analyses of green field, air-cured and flue-cured samples were carried out. Where possible, all were done on samples from the same leaves by marking and numbering leaves in the field when leaf punches were taken to get green field data. After air or flue curing, the same numbered leaves were sampled so that green/air and green/flue could be directly compared. The table below shows the results of green versus flue and green versus air cured samples. The data was standardised to microgram/cm$^2$ leaf.

TABLE 6

GW3 surface chemistry analyses of green field, air-cured and flue-cured samples
Exudate components: Green vs Flue- vs Air-Cured Field Tobaccos

| Type | cis-Abienol | α-CBT-ols | β-CBT-ols | ug/cm$^2$ LD | α-diols | β-diols | SEs | Oxidized |
|---|---|---|---|---|---|---|---|---|
| Green(20) | 6.695 | 1.278 | | 2.570 | 38.301 | 12.585 | 48.091 | 44.150 |
| ± | 3.834 | 1.155 | | 1.563 | 16.275 | 7.219 | 23.489 | 28.506 |
| Flue(16) | 0.926 | | | 3.003 | 27.916 | 14.986 | 43.338 | 92.269 |
| ± | 0.524 | | | 1.319 | 16.893 | 8.178 | 28.781 | 52.600 |
| | −7.2x | | | ≈ | ≈ | ≈ | ≈ | +2.1x |
| Air(5) | 2.374 | | | 3.017 | 42.968 | 20.887 | 45.557 | 107.589 |
| ± | 0.705 | | | 0.443 | 13.155 | 6.276 | 12.058 | 30.220 |
| | −2.8x | | | ≈ | ≈ | +1.7x | ≈ | +2.4x |
| Green(36) | 6.506 | | | 0.214 | | | 25.491 | 3.029 |
| ± | 2.800 | | | 0.369 | | | 10.148 | 1.775 |
| Flue(14) | 0.926 | | | 6.136 | | | 118.551 | 39.462 |
| ± | 1.101 | | | 3.711 | | | 50.446 | 26.083 |
| | −7x | | | +28.7 | | | +4.7 | +13 |

TABLE 6-continued

GW3 surface chemistry analyses of green field, air-cured and flue-cured samples
Exudate components: Green vs Flue- vs Air-Cured Field Tobaccos

| Type | cis-Abienol | α-CBT-ols | β-CBT-ols | ug/cm² LD | α-diols | β-diols | SEs | Oxidized |
|---|---|---|---|---|---|---|---|---|
| Air(11) | 2.736 | | | 1.712 | | | 38.135 | 15.565 |
| ± | 1.799 | | | 0.7 | | | 15.1 | 8.7 |
| | −2.38x | | | +8x | | | +1.5x | +5.1x |

Numbers in parantheses following green or flue or air indicate how many independent samples were analysed and used to derive the average. For example, for control green (20) means 20 independent samples. The mean values for these are show with the standard deviation below, e.g. for control green (2), 6.695±3.834.

The data for Green to Flue are for the lines: control and GW3—high cis-abienol. This data shows that cis-abienol was greatly decreased green-to-flue and, this cis may have been degraded to certain "oxidation products" in the right hand most column for the GW3—high cis-abienol lines. This data also shows that labdenediol was increased green-to-flue in GW3. The changes were porportional, e.g. when cis went down(µg/cm²) green-to-flue, labdenediol went up porportionally. Note that the Oxidized column values also increased substantially for GW3, green-to-flue. Additionally, CBTdiols were not greatly changed green-to-flue and sucrose ester amounts were not greatly changed green-to-flue in the control; whereas were increased (+4.7) significantly in the GW3 lines. Separate analyses (not shown) indicated no qualitative change in acyl group composition, green-to-flue, as expected for stable sucrose ester. The data for Green to Air shows that changes are smaller green-to-air than observed for green-to-flue. Only oxidized appeared to increase substantially, probably due to cis-abienol degradation.

Figure 5:
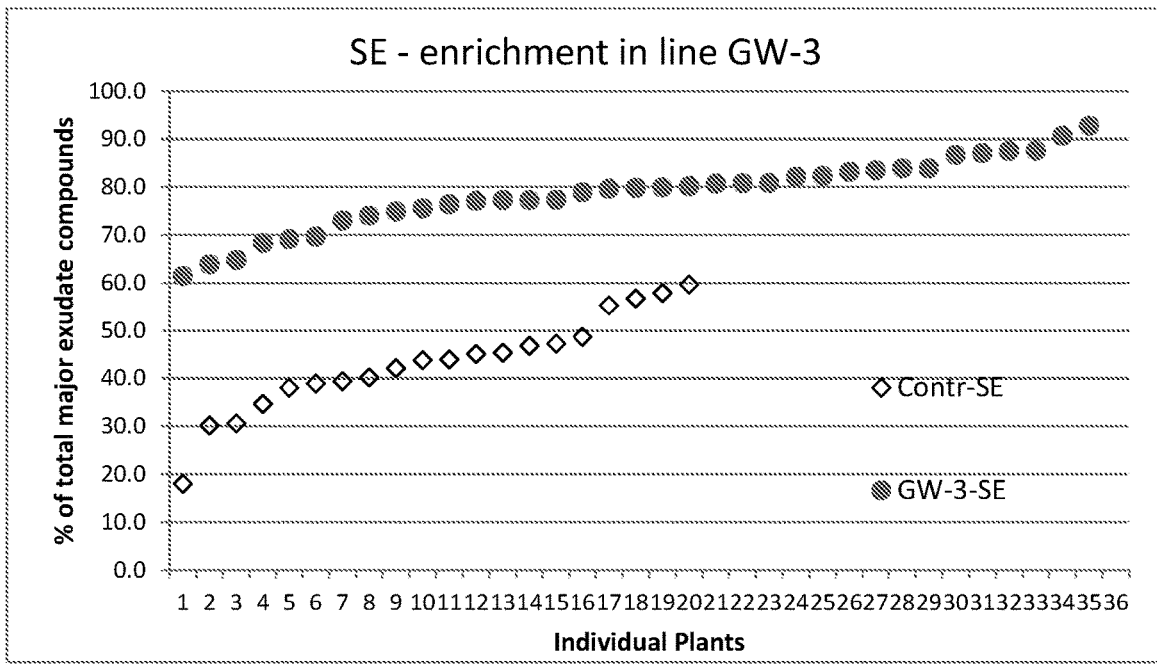
FIG. 5. shows a graph demonstrating sucrose ester enrichment in line GW-3 versus the control.

FIG. 5 demonstrates that sucrose ester content was enriched in the transgenic line GW-3 compared to the control. The sucrose ester content is presented as the percentage of total major exudate compounds. FIG. 6 demonstrates that cis-abienol content was enriched in the transgenic line GW-3 compared to the control. The cis-abienol content is presented as the percentage of total major exudate compounds.

Example 7

Exudate Components of Flue-Cured and Air-Cured 2016 Field Tobaccos

RNAi lines were grown in the field, T2 or T3, trait stable and were harvested. Flue cured plants were harvested as 3 primings in 2016. In the 2016 trial, air cured plants were stalk cut, air cured, and separated into ⅓ lower leaves, ⅓ mid leaves, and ⅓ upper leaves, before analysis. This was to mimic the general approach used for commercial production.

TABLE 7

Exudate components in Flue-cured 2016 field tobaccos

| Line | Prime | cis-Abienol | α-CBT-ols | β-CBT-ols | ug/cm² LD | α-diols | β-diols | SEs | Oxidized |
|---|---|---|---|---|---|---|---|---|---|
| Control | Prime 1 | 0.323 | | | 1.570 | 20.384 | 10.510 | 13.464 | 43.047 |
| | ± | 0.189 | | | 0.500 | 6.539 | 3.103 | 3.667 | 17.891 |
| | Prime 2 | 0.979 | | | 2.851 | 34.639 | 17.404 | 21.306 | 70.358 |
| | ± | 0.263 | | | 0.438 | 4.831 | 2.484 | 4.005 | 7.739 |
| | Prime 3 | 0.976 | | | 3.536 | 31.9 | 16.126 | 30.933 | 78.702 |
| | ± | 1.057 | | | 1.366 | 19.789 | 9.654 | 12.778 | 35.794 |
| GW-3 | Prime 1 | 0.492 | | | 1.888 | 0.725 | | 20.666 | 10.981 |
| | ± | 0.190 | | | 0.334 | 0.458 | | 3.176 | 3.716 |
| | Prime 2 | 3.601 | | | 3.990 | 0.247 | | 37.977 | 27.576 |
| | ± | 2.711 | | | 0.309 | 0.440 | | 5.150 | 7.434 |
| | Prime 3 | 3.666 | | | 4.955 | 0.3 | | 56.1 | 28.2 |
| | ± | 4.039 | | | 0.528 | 0.606 | | 2.608 | 11.122 |
| GW-2 | Prime 1 | 0.415 | | | 22.762 | 5.050 | 2.886 | 19.216 | 16.865 |
| | ± | 0.090 | | | 4.796 | 1.702 | 0.937 | 1.368 | 1.031 |
| | Prime 2 | 0.846 | | | 30.576 | 10.309 | 4.875 | 30.062 | 28.684 |
| | ± | 0.235 | | | 5.202 | 3.217 | 1.343 | 2.971 | 5.258 |
| | Prime 3 | 0.634 | | | 27.723 | 13.671 | 6.764 | 51.426 | 38.462 |
| | ± | 0.525 | | | 4.806 | 4.965 | 1.911 | 6.338 | 11.408 |
| GW-1 | Prime 1 | 0.484 | | | 1.713 | 0.876 | | 17.567 | 5.486 |
| | ± | 0.060 | | | 0.163 | 0.932 | | 4.262 | 1.596 |
| | Prime 2 | 3.076 | | | 3.656 | 0.399 | | 26.777 | 10.136 |
| | ± | 1.434 | | | 0.285 | 0.318 | | 3.479 | 0.203 |
| | Prime 3 | 2.406 | | | 4.8 | 2.6 | | 43.9 | 20.3 |
| | ± | 2.833 | | | 1.124 | 2.643 | | 6.184 | 11.036 | a) In 2016, unlike 2014, for flue-cured, 3 primings were taken and analyzed separately.
b) Each value of each priming is an average of 3 repeats. Each repeat is an average from 20 plants.
c) In 2016, unlike 2014, green tissue of field plants was not monitored.

Conclusion

The data in Table 7 show that sucrose esters were enriched in lines GW1-3 compared to control in the 2016 flue cured field tobacco.

TABLE 8

Exudate components in Air-cured 2016 field tobaccos

| Line | Level | cis-Abienol | α-CBT-ols | β-CBT-ols | ug/cm² LD | α-diols | β-diols | SEs | Oxidized |
|---|---|---|---|---|---|---|---|---|---|
| control | Upper | 0.958 | | | 2.662 | 36.821 | 16.207 | 27.526 | 66.451 |
| | ± | 0.414 | | | 0.447 | 10.186 | 4.620 | 2.211 | 13.455 |
| | Mid | 1.887 | | | 2.364 | 42.771 | 19.983 | 29.521 | 101.747 |
| | ± | 0.682 | | | 1.658 | 9.932 | 4.926 | 12.566 | 41.875 |
| | Lower | 1.840 | | | 1.929 | 39.4 | 18.355 | 19.024 | 62.051 |
| | ± | 0.193 | | | 0.156 | 3.465 | 2.633 | 4.155 | 11.880 |
| GW1 | Upper | 6.998 | | | 4.347 | 0.876 | | 32.052 | 24.975 |
| | ± | 0.186 | | | 0.651 | 0.932 | | 0.841 | 1.517 |
| | Mid | 7.977 | | | 4.755 | 0.399 | | 32.427 | 37.114 |
| | ± | 0.713 | | | 1.607 | 0.318 | | 13.599 | 8.602 |
| | Lower | 6.399 | | | 2.9 | 2.6 | | 22.8 | 27.7 |
| | ± | 0.338 | | | 0.371 | 2.643 | | 6.878 | 8.338 |
| GW-2 | Upper | 0.580 | | | 34.120 | 15.176 | 6.878 | 48.876 | 48.978 |
| | ± | 0.283 | | | 5.014 | 2.307 | 1.279 | 13.469 | 11.735 |
| | Mid | 1.102 | | | 45.270 | 16.209 | 7.634 | 50.046 | 54.201 |
| | ± | 0.160 | | | 12.941 | 7.268 | 3.246 | 13.113 | 12.757 |
| | Lower | 0.850 | | | 43.365 | 10.751 | 5.077 | 35.648 | 39.406 |
| | ± | 0.346 | | | 18.908 | 5.256 | 2.539 | 16.307 | 16.215 |
| GW-3 | Upper | 7.024 | | | 4.768 | | | 43.550 | 31.062 |
| | ± | 0.731 | | | 0.333 | | | 14.971 | 9.637 |
| | Mid | 7.167 | | | 4.760 | | | 42.139 | 48.925 |
| | ± | 3.085 | | | 2.434 | | | 0.653 | 3.482 |
| | Lower | 4.589 | | | 3.121 | | | 25.0 | 27.0 |
| | ± | 1.305 | | | 0.746 | | | 4.699 | 7.849 | a) In 2016, unlike 2014, upper ⅓, middle ⅓ and lower ⅓ leaves of stalk cut, air-cured plants were pooled and analyzed separately.
b) Each value of each level is an average of 20 leaves from 20 independent plants.
c) In 2016, unlike 2014, green tissue of field plants was not monitored.

Conclusion

The data in Table 8 show that sucrose esters were enriched in lines GW1-3 compared to control in the 2016 air cured field tobacco.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for producing a tobacco plant or part thereof, a tobacco plant propagation material, a tobacco leaf, a cut harvested tobacco leaf, a processed tobacco leaf or a cut and processed tobacco leaf or a tobacco cell culture or tobacco product which has increased sucrose ester content, the method comprising modifying said tobacco to inhibit the activity or expression of a diterpene synthesis gene, wherein the sucrose ester content is increased in comparison to a tobacco plant or a tobacco cell culture which has not been modified to inhibit the activity or expression of a diterpene synthesis gene, and wherein
the diterpene synthesis gene is a terpene synthase 3-8 gene having a polynucleotide sequence as set forth in SEQ ID No. 3, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto.

2. The method of claim 1, wherein expression of the diterpene synthesis gene is inhibited using RNA interference (RNAi).

3. The method according to claim 2, wherein expression is inhibited in said terpene synthase 3-8 gene using a ddRNAi DNA construct comprising,
i) at least nucleotides 884 to 904 of the terpene synthase 3-8 gene where the numbering is determined by alignment with SEQ ID No. 3; or
ii) at least nucleotides 1497 to 1517 of the terpene synthase 3-8 gene where the numbering is determined by alignment with SEQ ID No. 3.

4. A tobacco plant or part thereof or a tobacco cell culture which has been modified to achieve an increase in sucrose ester content in comparison to an unmodified plant or an unmodified tobacco cell culture, wherein the modification is the inhibition of the activity or expression of a diterpene synthesis gene, wherein
the diterpene synthesis gene is a terpene synthase 3-8 gene having a polynucleotide sequence as set forth in SEQ ID No. 3, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto.

5. The tobacco plant or part thereof or a tobacco cell culture of claim 4 comprising a ddRNAi construct inhibiting expression of a terpene synthase 3-8 gene using a ddRNAi DNA construct comprising,
i) at least nucleotides 884 to 904 of the terpene synthase 3-8 gene where the numbering is determined by alignment with SEQ ID No. 3; or
ii) at least nucleotides 1497 to 1517 of the terpene synthase 3-8 gene where the numbering is determined by alignment with SEQ ID No. 3.

6. Tobacco plant propagation material obtainable from the tobacco plant or the tobacco cell culture according to claim 4, wherein said plant propagation material is seed.

7. The method of claim 1, wherein the sucrose ester content of the tobacco plant is at least 2-fold higher in the modified tobacco plant or tobacco cell culture in comparison to a tobacco plant or tobacco cell culture which has not been modified to inhibit the activity or expression of the diterpene synthesis gene.

8. The tobacco plant or part thereof or tobacco cell culture according to claim 4, wherein the sucrose ester content of the tobacco plant is at least 2-fold higher in the modified tobacco plant or tobacco cell culture in comparison to a tobacco plant or tobacco cell culture which has not been modified to inhibit the activity or expression of the diterpene synthesis gene.

9. The method of claim 1 comprising producing a tobacco industry product, tobacco leaf or cured tobacco leaf.

10. The method of claim 1, further comprising a process selected from crossing said plant with a second plant or growing a crop of said plants.

11. A harvested leaf of a tobacco plant modified to achieve an increase in sucrose ester content in comparison to an unmodified tobacco leaf, wherein the modification is the inhibition of the activity or expression of a diterpene synthesis gene, wherein
the diterpene synthesis gene is a terpene synthase 3-8 gene having a polynucleotide sequence as set forth in SEQ ID No. 3, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto.

12. The harvested leaf of a tobacco plant according to claim 11 wherein the harvested leaf of a tobacco plant is a cut harvested leaf.

13. A processed tobacco leaf of a tobacco plant, modified to achieve an increase in sucrose ester content in comparison to an unmodified tobacco leaf, where the modification is the inhibition of the activity or expression of a diterpene synthesis gene, wherein the diterpene synthesis gene is a terpene synthase3-8 gene having a polynucleotide sequence as set forth in SEQ ID No. 3, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto.

14. A processed tobacco leaf of a tobacco plant modified to achieve an increase in sucrose ester content in comparison to an unmodified tobacco leaf, where the modification is the inhibition of the activity or expression of a diterpene synthesis gene,
wherein the diterpene synthesis gene is selected from:
a) a cyclase 2 gene (CYC2) having a polynucleotide sequence as set forth in SEQ ID No. 8 or SEQ ID No. 9, or a polynucleotide sequence with at least 90% sequence identity thereto, or having a polynucleotide sequence encoding a polypeptide comprising the amino acid sequence as set forth in SEQ ID No. 10 or a polynucleotide sequence with at least 90% sequence identity thereto;
b) a CBTol cyclase gene having a polynucleotide sequence as set forth in SEQ ID No. 1, or a polynucleotide sequence with at least 90% sequence identity thereto, or having a polynucleotide sequence encoding a polypeptide comprising the amino acid sequence as set forth in SEQ ID No. 2 or a polynucleotide sequence with at least 90% sequence identity thereto; or
c) a terpene synthase 3-8 gene having a polynucleotide sequence as set forth in SEQ ID No. 3, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto,
wherein the tobacco is processed by curing, fermenting, pasteurising or a combination thereof.

15. The processed tobacco leaf according to claim 13 wherein the processed tobacco leaf is a cut processed tobacco leaf.

16. A tobacco industry product prepared from a tobacco plant, part thereof, plant propagation material thereof, selected from a harvested leaf, processed tobacco leaf, cured tobacco material or a tobacco blend comprising said cured tobacco modified to achieve an increase in sucrose ester content in comparison to an unmodified tobacco plant or part thereof, wherein the modification is the inhibition of the activity or expression of a diterpene synthesis gene, wherein the diterpene synthesis gene is selected from:
a) a cyclase 2 gene (CYC2) having a polynucleotide sequence as set forth in SEQ ID No. 8 or SEQ ID No. 9, or a polynucleotide sequence with at least 90% sequence identity thereto, or having a polynucleotide sequence encoding a polypeptide comprising the amino acid sequence as set forth in SEQ ID No. 10 or a polynucleotide sequence with at least 90% sequence identity thereto;
b) a CBTol cyclase gene having a polynucleotide sequence as set forth in SEQ ID No. 1, or a polynucleotide sequence with at least 90% sequence identity thereto, or having a polynucleotide sequence encoding a polypeptide comprising the amino acid sequence as set forth in SEQ ID No. 2 or a polynucleotide sequence with at least 90% sequence identity thereto; or
c) a terpene synthase 3-8 gene having a polynucleotide sequence as set forth in SEQ ID No. 3, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto.

17. The tobacco industry product according to claim 16, wherein the tobacco product is selected from a combustible smoking article, a smokeless tobacco product, non-combustible aerosol provision system, a tobacco heating device, an aerosol-generating device, a tobacco cell culture, cured tobacco material or a tobacco blend comprising said cured tobacco material.

18. A method for producing a tobacco industry product or cured tobacco leaf which has increased sucrose ester content, the method comprising producing a tobacco plant, wherein said tobacco plant is modified to inhibit the activity or expression of a diterpene synthesis gene, wherein the sucrose ester content is increased in comparison to a tobacco plant or a tobacco cell culture which has not been modified to inhibit the activity or expression of a diterpene synthesis gene and wherein the diterpene synthesis gene is selected from:
a) a cyclase 2 gene (CYC2) having a polynucleotide sequence as set forth in SEQ ID No. 8 or SEQ ID No. 9, or a polynucleotide sequence with at least 90% sequence identity thereto, or having a polynucleotide sequence encoding a polypeptide comprising the amino acid sequence as set forth in SEQ ID No. 10 or a polynucleotide sequence with at least 90% sequence identity thereto;

b) a CBTol cyclase gene having a polynucleotide sequence as set forth in SEQ ID No. 1, or a polynucleotide sequence with at least 90% sequence identity thereto, or having a polynucleotide sequence encoding a polypeptide comprising the amino acid sequence as set forth in SEQ ID No. 2 or a polynucleotide sequence with at least 90% sequence identity thereto; or c) a terpene synthase 3-8 gene having a polynucleotide sequence as set forth in SEQ ID No. 3, or a functional fragment thereof, or a polynucleotide sequence with at least 90% sequence identity thereto, or having a polynucleotide sequence encoding a polypeptide comprising the amino acid sequence as set forth in SEQ ID No. 4 or a polynucleotide sequence with at least 90% sequence identity thereto;

further producing a tobacco industry product or cured tobacco leaf.

\* \* \* \* \*